(12) United States Patent
Deaton et al.

(10) Patent No.: US 11,471,183 B1
(45) Date of Patent: Oct. 18, 2022

(54) THROMBECTOMY METHODS

(71) Applicant: Boston Scientific Scimed, Inc., Maple Grove, MN (US)

(72) Inventors: David Deaton, Fremont, CA (US); Christopher K. Huynh, Fremont, CA (US); Michael Dotsey, Chester Springs, PA (US); Michael P. Wallace, Pleasanton, CA (US); Jayson Delos Santos, Fremont, CA (US); Gavin P. Wallace, Pleasanton, CA (US); Michael Hogendijk, Santa Rosa, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 17/519,539

(22) Filed: Nov. 4, 2021

Related U.S. Application Data

(60) Provisional application No. 63/249,561, filed on Sep. 28, 2021, provisional application No. 63/151,054, filed on Feb. 18, 2021.

(51) Int. Cl.
*A61B 17/3207* (2006.01)
*A61B 17/32* (2006.01)

(52) U.S. Cl.
CPC ............ *A61B 17/32075* (2013.01); *A61B 2017/320008* (2013.01); *A61B 2017/320741* (2013.01)

(58) Field of Classification Search
CPC ............ A61B 17/22; A61B 17/221; A61B 17/320725; A61B 2017/22079;
(Continued)

(56) References Cited

U.S. PATENT DOCUMENTS 5,192,268 A 3/1993 Shiber
5,836,868 A 11/1998 Ressemann et al.
(Continued)

FOREIGN PATENT DOCUMENTS

EP 2063791 B1 12/2016
EP 3539486 A1 9/2019
(Continued)

OTHER PUBLICATIONS

Deaton et al.; U.S. Appl. No. 17/519,533 entitled "Thrombectomy apparatuses," filed Nov. 4, 2021.
(Continued)

*Primary Examiner* — Kathleen S Holwerda
*Assistant Examiner* — Lauren Dubose
(74) *Attorney, Agent, or Firm* — Seager, Tufte & Wickhem, LLP

(57) ABSTRACT

Methods and apparatuses for removing material (e.g., clot) from within a body, including inverting thrombectomy apparatuses. These methods and apparatuses may include methods and apparatuses for reusing portion of the devices, method and apparatuses for loading and reloading the inverting thrombectomy apparatuses, and methods and apparatuses for improving and enhancing the ability of the inverting thrombectomy apparatuses to remove clot. In particular, described herein are expandable scraper devices that may be used in conjunction with the inverting thrombectomy apparatuses descried herein, or on their own.

29 Claims, 31 Drawing Sheets

(58) Field of Classification Search
CPC .......... A61B 17/3207; A61B 17/22031; A61B 2017/22094; A61B 2017/320716; A61B 2017/22001; A61B 2017/22084; A61B 2017/320775; A61B 17/3439; A61B 2017/0078; A61B 2017/22002; A61B 2017/320008; A61B 2017/22061; A61B 2017/320733; A61B 17/12109; A61M 25/104; A61M 2025/1052; A61M 2025/109; A61M 25/0043; A61M 25/0136; A61F 2/013; A61F 2/011; A61F 2002/016; A61F 2/01; A61F 2/06
See application file for complete search history.

(56) References Cited

U.S. PATENT DOCUMENTS

| | | | |
|---|---|---|---|
| 6,001,118 A * | 12/1999 | Daniel | A61B 17/22031 |
| | | | 606/200 |
| 6,135,991 A | 10/2000 | Muni et al. | |
| 6,391,044 B1 | 5/2002 | Yadav et al. | |
| 6,565,583 B1 | 5/2003 | Deaton et al. | |
| 6,605,074 B2 | 8/2003 | Azizi et al. | |
| 6,632,236 B2 | 10/2003 | Hogendijk | |
| 7,029,488 B2 | 4/2006 | Schönholz et al. | |
| 7,713,227 B2 | 5/2010 | Wholey et al. | |
| 7,989,207 B2 | 8/2011 | Soito et al. | |
| 8,052,640 B2 | 11/2011 | Fiorella et al. | |
| 8,118,827 B2 | 2/2012 | Duerig et al. | |
| 8,298,257 B2 | 10/2012 | Sepetka et al. | |
| 8,323,243 B2 | 12/2012 | Schneider et al. | |
| 8,465,509 B2 | 6/2013 | Shekalim | |
| 8,475,487 B2 | 7/2013 | Bonnette et al. | |
| 8,646,460 B2 | 2/2014 | Utley et al. | |
| 8,734,465 B2 | 5/2014 | Teague | |
| 8,795,305 B2 | 8/2014 | Martin et al. | |
| 8,795,322 B2 | 8/2014 | Cully et al. | |
| 8,801,748 B2 | 8/2014 | Martin | |
| 9,408,625 B2 | 8/2016 | Remmerswaal et al. | |
| 9,451,984 B2 | 9/2016 | Zhou et al. | |
| 9,463,035 B1 | 10/2016 | Greenhalgh et al. | |
| 9,622,762 B2 | 4/2017 | Dahm et al. | |
| 9,775,631 B2 | 10/2017 | Li et al. | |
| 9,826,995 B2 | 11/2017 | Dahm et al. | |
| 10,010,335 B2 | 7/2018 | Greenhalgh et al. | |
| 10,022,139 B2 | 7/2018 | Kobayashi et al. | |
| 10,028,759 B2 | 7/2018 | Wallace et al. | |
| 10,080,575 B2 | 9/2018 | Brady et al. | |
| 10,159,509 B2 | 12/2018 | Nishio et al. | |
| 10,252,036 B2 | 4/2019 | Aggerholm et al. | |
| 10,278,715 B2 | 5/2019 | Dahm et al. | |
| 10,300,256 B2 | 5/2019 | Aboytes | |
| 10,383,645 B2 | 8/2019 | Nishigishi | |
| 10,383,751 B2 | 8/2019 | Ferrera et al. | |
| 10,499,934 B2 | 12/2019 | Dahm et al. | |
| 10,653,433 B2 | 5/2020 | Masubuchi et al. | |
| 10,667,833 B2 | 6/2020 | Vale et al. | |
| 10,722,255 B2 | 7/2020 | Lenker et al. | |
| 10,743,907 B2 | 8/2020 | Bruzzi et al. | |
| 10,813,663 B2 | 10/2020 | Bruzzi et al. | |
| 10,874,410 B2 | 12/2020 | Scarpine et al. | |
| 10,925,624 B2 | 2/2021 | Diamant et al. | |
| 2002/0072730 A1* | 6/2002 | McGill | A61F 2/013 |
| | | | 604/525 |
| 2003/0176884 A1 | 9/2003 | Berrada et al. | |
| 2007/0060942 A2 | 3/2007 | Azizi | |
| 2014/0263032 A1 | 9/2014 | Liddy et al. | |
| 2015/0359549 A1* | 12/2015 | Lenker | A61B 17/12118 |
| | | | 600/585 |
| 2017/0035437 A1 | 2/2017 | Sarge et al. | |
| 2018/0042626 A1 | 2/2018 | Greenhalgh et al. | |
| 2019/0117214 A1 | 4/2019 | Harar et al. | |
| 2019/0133616 A1* | 5/2019 | Sachar | A61B 17/221 |
| 2020/0078045 A1 | 3/2020 | Wallace et al. | |
| 2020/0121336 A1 | 4/2020 | Tsukamoto et al. | |

FOREIGN PATENT DOCUMENTS

| | | |
|---|---|---|
| WO | WO2018/078563 A1 | 5/2018 |
| WO | WO2018/193597 A1 | 10/2018 |
| WO | WO2018/193598 A1 | 10/2018 |
| WO | WO2020/113957 A1 | 6/2020 |
| WO | WO2020/162724 A1 | 8/2020 |

OTHER PUBLICATIONS

Wallace et al.; U.S. Appl. No. 17/519,551 entitled "Thrombectomy apparatueses and methods," filed Nov. 4, 2021.

* cited by examiner

Braid heat set to collapsed, small diameter

.018 "Pull wire

Distal end of braid bonded to pullwire

Proximal end of braid is inverted & bonded blue catheter (OD ~38")

Proximal end of blue catheter (OD ~38")

Pull, .018 " wire to compress braid & form backstop push,018 "wire to elongate/collapse braid

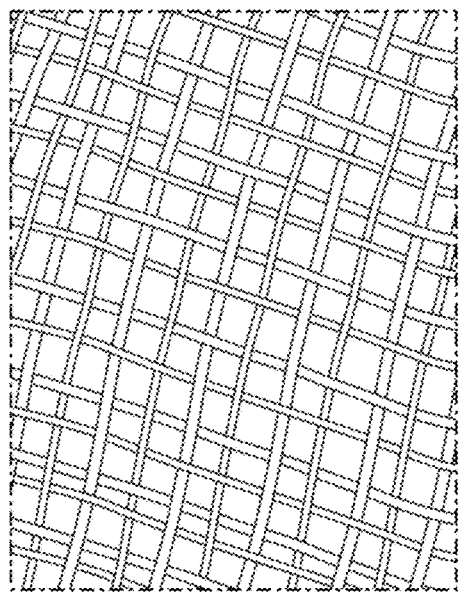 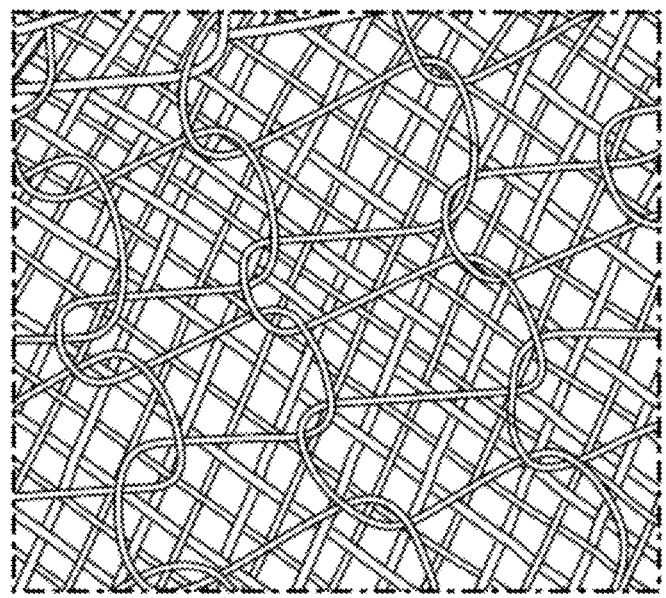
FIG. 14          FIG. 15
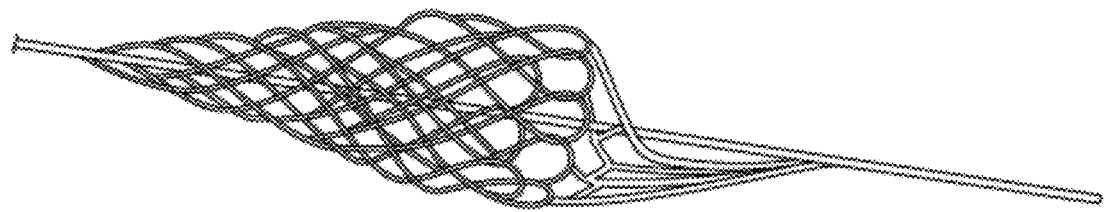
FIG. 16

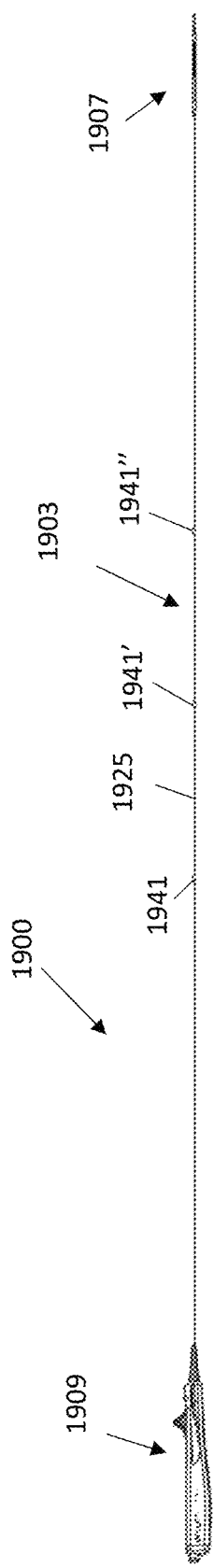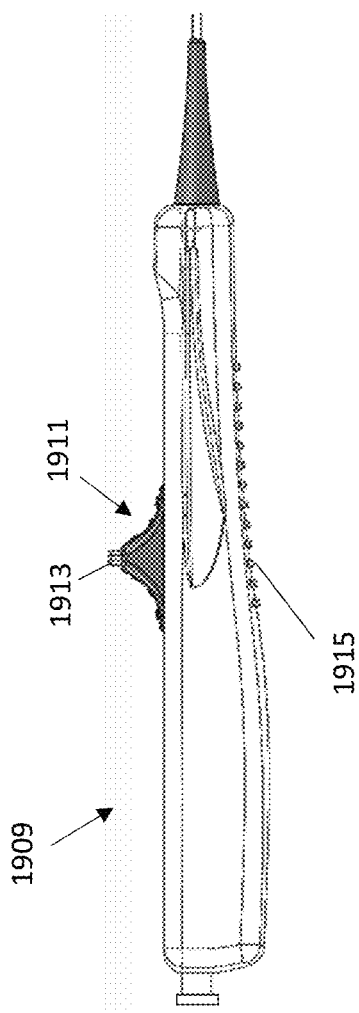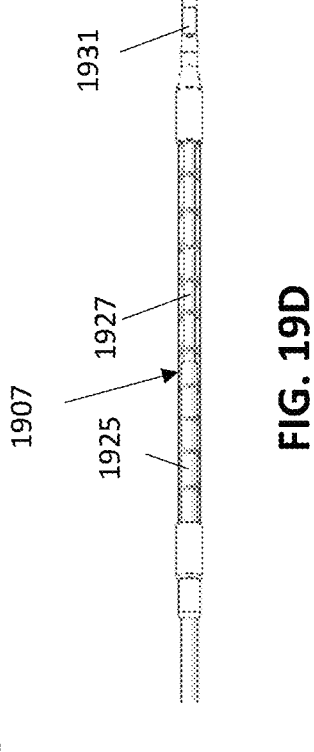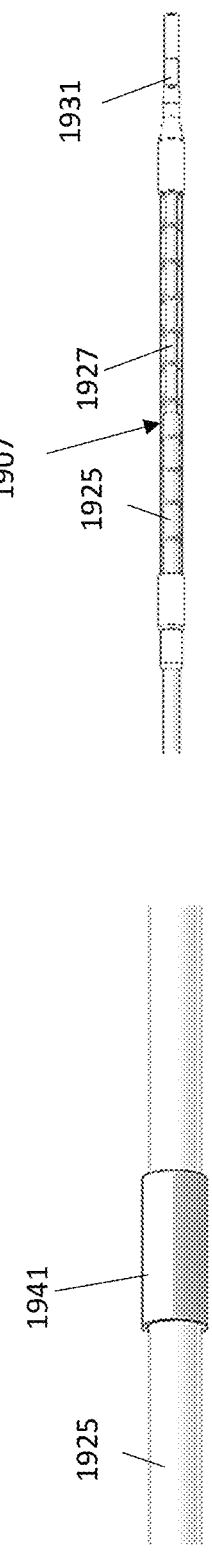
FIG. 19A
FIG. 19B
FIG. 19C
FIG. 19D

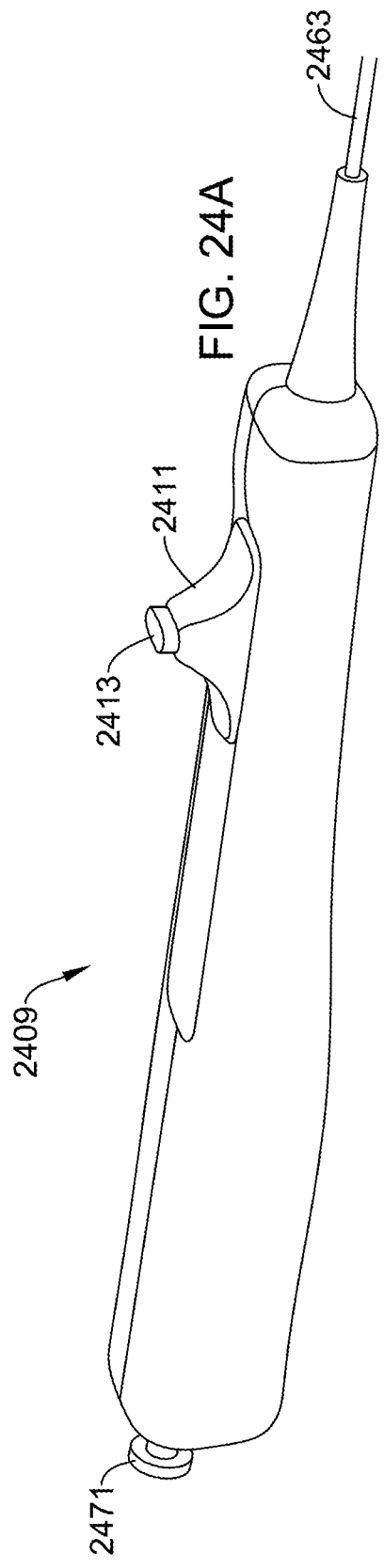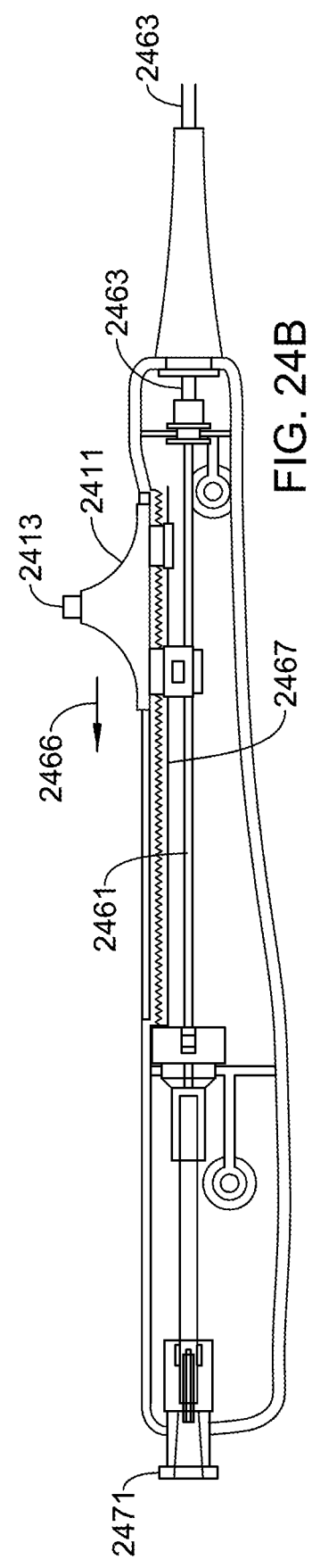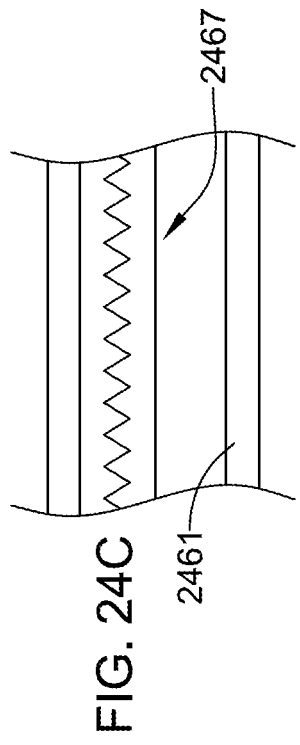

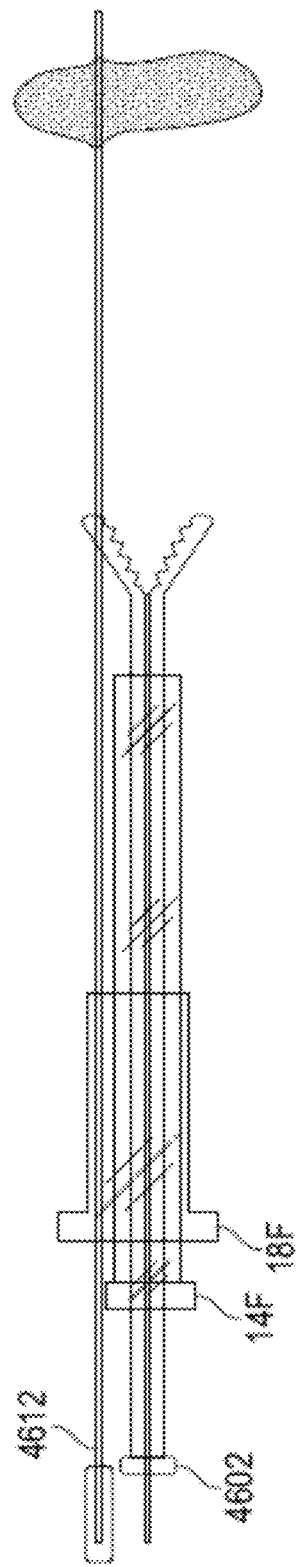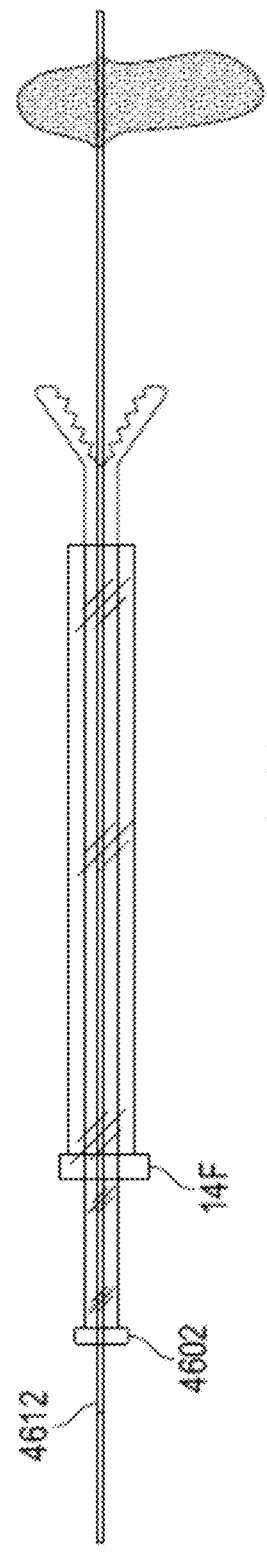

THROMBECTOMY METHODS

CROSS REFERENCE TO RELATED APPLICATIONS

This patent application claims priority to U.S. Provisional Patent Application No. 63/151,054, titled "THROMBECTOMY TOOLS AND APPARATUSES" and filed on Feb. 18, 2021, and to U.S. Provisional Patent Application No. 63/249,561, titled "THROMBECTOMY TOOLS AND APPARATUSES" and filed on Sep. 28, 2021, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Removal of material from within a vessel or chamber is often useful. For example, removal of tissue such as blood clots from within a vasculature may improve patient conditions and quality of life. Clot removal may be beneficial or even necessary to improve patient outcomes. For example, in the peripheral vasculature, interventions and procedures can reduce the need for an amputation by 80 percent. The ultimate goal of any technique to treat these conditions is to remove the blockage and to restore patency, quickly, safely, and cost effectively.

Devices for mechanically removing material, including thrombus material, from with a lumen of the vessel may include an inverting tube for removing material from a body lumen, such as for removing a clot from a blood vessel (e.g., thrombectomy devices), are disclosed and described in each of U.S. Pat. No. 10,271,864, as well as in each of U.S. Patent Application Publication Nos. 2019/0117214, 2018/0042626 and 2018/0042624, and in U.S. patent application Ser. No. 16/566,393. These apparatuses do an excellent job at removing material from within a blood vessel, but in some situations may face challenges when removing large amounts of material which may require multiple attempts to remove, and/or when removing softer clot material, which may be difficult to grip. In some cases, it may be difficult to completely remove clot material from against the wall of the vessel.

Thus, there is a need for devices, including thrombectomy devices, that can be remove tissue, and particularly large and/or soft materials, from within a body lumen. Described herein are apparatuses (devices, systems and kit) and methods of using them that may address the needs and problems discussed above.

SUMMARY OF THE DISCLOSURE

The methods and apparatuses (devices, systems, etc.) described herein relate to improvement in the operation, and in particular, the insertion and use of, materials for removing material from within a vessel.

Described herein are methods and apparatuses for assisting in removal of material (e.g., clot material), including removing clot material from the vessel wall(s). These methods and apparatuses may be used by themselves or in conjunction with (and as part of) a system for removing clot material, e.g., by suction and/or by inverting (rolling) a flexible tube into an inversion support catheter.

For example, described herein are methods of using a scraper or backstop to aid in removing clot material. For example, a method of removing clot material from within a vessel lumen may include: expanding distal expanding region of an expandable scraper from a compressed configuration into or adjacent to a clot; pulling the distal expanding region proximally towards an inverting thrombectomy apparatus so that the distal expanding region scrapes a wall of the lumen and drives the clot material proximally to a distal end of an inversion support catheter of the inverting thrombectomy apparatus; and inverting a flexible tube of the inverting thrombectomy apparatus from an outer surface of the inversion support catheter and into the lumen of the inversion support catheter to capture clot material by pulling a portion of the flexible tube within the inversion support catheter proximally.

Thus any of these apparatuses and methods may include or may use an inverting tube apparatus for removing material from within a body, including a body lumen; an inverting tube apparatus may generally include an inversion support, which may include a catheter ("inversion support catheter") and a flexible tube configured to move over the outside of the inversion support and invert into the inversion support. In some examples a puller attached to a first end of the inversion support for pulling the flexible tube into the inversion support. In some examples the inversion support includes a funnel region at its distal end that may be collapsible and expandable and may be biased to expand into an expanded funnel shape. The apparatuses described herein may be generally referred to as apparatuses for removing a material from a vessel and may be configured as mechanical thrombectomy apparatuses.

The methods and apparatuses described herein may provide improvements for introducing inverting tube apparatuses into the body, including in particular introduces for inserting inverting tube apparatuses including an expandable funnel at the distal end region of the apparatus.

The distal expanding region may be pulled proximally while inverting the flexible tube of the inverting thrombectomy apparatus. Any of these methods may include inserting the expandable scraper distally into and at least partially through the clot before expanding it from the compressed configuration. Any of these methods may include inserting the inverting thrombectomy apparatus over an elongate end of the expandable scraper.

Expanding the distal expanding region may comprise pulling a wire within the expandable scraper to expand the expandable scraper. Expanding the distal expanding region may comprise forming a funnel shape. Any of these methods may include collapsing the distal expanding region back to the compressed configuration and repositioning the distal expanding region distally into or adjacent to additional clot material.

Pulling a portion of the flexible tube within the inversion support catheter may comprise pulling a puller that is attached to the flexible tube.

Also described are methods of using apparatuses with integrated scrapers. For example a method of removing clot material from within a vessel lumen may include: expanding distal expanding region of an inverting thrombectomy apparatus from a compressed configuration into or adjacent to a clot; pushing the distal expanding region proximally so that the distal expanding region scrapes a wall of the lumen and drives the clot material to a distal end of an inversion support catheter of the inverting thrombectomy apparatus; and inverting a flexible tube of the inverting thrombectomy apparatus from an outer surface of the inversion support catheter and into the lumen of the inversion support catheter to capture clot material by pulling a portion of the flexible tube within the inversion support catheter proximally.

An apparatus for removing a material from within a body lumen (e.g., including an integrated scraper) may include: an inversion support catheter having an expandable region proximal to the distal end of the inversion support catheter; a pull-wire coupled to the expandable region configure to be pulled to expand the expandable region; a puller within and configured to freely slide with a lumen of the inversion support catheter; and a knitted or braided flexible tube extending from a distal end region of the puller, over a distal end opening of the distal end of the inversion support catheter and over an outer surface of the inversion support catheter, wherein pulling the puller proximally causes the flexible tube to roll and invert over the distal end opening of the inversion support catheter from the outer surface and into the inner lumen. Any of these apparatuses may include an expandable funnel-shaped distal end on the inversion support catheter, wherein the expandable region is proximal to the expandable funnel-shaped distal end.

Thus, as mentioned above, described herein are methods of using an expandable scraper device in parallel or combination with inverting thrombectomy apparatus (and in some examples, suction) to remove clot material. For example, described herein are methods of removing clot material from within a vessel lumen, the method comprising: expanding distal expanding region of an expandable scraper from a collapsed configuration into or adjacent to a clot; pulling the distal expanding region proximally so that the distal expanding region scrapes a wall of the lumen and drives the clot material proximally; and inverting a flexible tube of an inverting thrombectomy apparatus from an outer surface of a distal end region of an inversion support catheter over a distal end opening of the inversion support catheter and into a lumen of the inversion support catheter to capture clot material by pulling a portion of the flexible tube within the inversion support catheter proximally.

Any of the methods described herein may include applying suction while inverting the flexible tube. Alternatively or additionally, the methods described herein may include pulling the distal expanding region proximally while inverting the flexible tube of the inversion support catheter.

The methods described herein may include removing the expandable scraper from the vessel lumen before inverting the flexible tube. For example, the methods may include removing the expandable scraper from the vessel lumen and positioning a distal end of the inverting thrombectomy apparatus adjacent to the clot material before inverting the flexible tube.

Any of these methods may include repeating the steps of expanding the distal expansion region of the expandable scraper, pulling the distal expanding region proximally and inverting the flexible tube of the inverting thrombectomy apparatus to remove clot material. In some examples these steps may be alternated.

In some examples, the expandable scraper may be inserted distally into and at least partially through the clot before expanding it from the collapsed configuration.

The method may include inserting the inverting thrombectomy apparatus over an elongate end of the expandable scraper. In some examples, the method may include expanding the distal expanding region by pulling a wire within the expandable scraper to expand the expandable scraper. Expanding the distal expanding region may comprise forming a funnel shape. The methods described herein may include collapsing the distal expanding region back to the collapsed configuration and repositioning the distal expanding region distally into or adjacent to additional clot material. Pulling a portion of the flexible tube within the inversion support catheter may comprise pulling a puller that is attached to the flexible tube.

For example, a method of removing clot material from within a vessel lumen may include: expanding distal expanding region of an expandable scraper from a collapsed configuration into or adjacent to a clot; pulling the distal expanding region proximally towards an inverting thrombectomy apparatus so that the distal expanding region scrapes a wall of the lumen and drives the clot material proximally to a distal end of an inversion support catheter of the inverting thrombectomy apparatus; and inverting a flexible tube of the inverting thrombectomy apparatus from an outer surface of the inversion support catheter and into the lumen of the inversion support catheter to capture clot material by pulling a portion of the flexible tube within the inversion support catheter proximally.

For example, a method of removing clot material from within a vessel lumen may include: expanding distal expanding region of an inverting thrombectomy apparatus from a collapsed configuration into or adjacent to a clot; pulling or pushing the distal expanding region proximally so that the distal expanding region scrapes a wall of the lumen and drives the clot material to a distal end of an inversion support catheter of the inverting thrombectomy apparatus; and inverting a flexible tube of the inverting thrombectomy apparatus from an outer surface of the inversion support catheter and into the lumen of the inversion support catheter to capture clot material by pulling a portion of the flexible tube within the inversion support catheter proximally.

A method of removing clot material from within a vessel lumen may include: positioning a distal end region of an expandable scraper into or adjacent to a clot; expanding a distal expanding region of the expandable scraper from a collapsed configuration into an expanded configuration; positioning a distal end region of an inverting thrombectomy apparatus adjacent to the clot; pulling the distal expanding region proximally so that the distal expanding region scrapes a wall of the lumen and drives the clot material proximally; inverting a flexible tube of an inverting thrombectomy apparatus from an outer surface of a distal end region of an inversion support catheter over a distal end opening of the inversion support catheter and into a lumen of the inversion support catheter to capture clot material by pulling a portion of the flexible tube within the inversion support catheter proximally.

In any of these methods, positioning both the distal end region of the expandable scraper and the distal end region of the inverting thrombectomy apparatus may comprises positioning through the same sheath. Alternatively, positioning the distal end region of the expandable scraper may comprise inserting the expandable scraper through a first sheath and positioning the distal end region of the inverting thrombectomy apparatus comprises inserting the inverting thrombectomy apparatus through a second sheath. The first and second sheaths may be located at different regions of the vasculature. In some examples the expandable scraper may be inserted though the same sheath as the inverting thrombectomy apparatus, but the inverting thrombectomy apparatus may be inserted after removing the expandable scraper, or vice versa. For example, any of the methods described herein may include removing the expandable scraper before positioning the distal end region of the inverting thrombectomy apparatus.

Any of these methods may include pulling the distal expanding region proximally while inverting the flexible tube of the inverting thrombectomy apparatus.

As mentioned, in some examples, positioning the distal end region of the expandable scraper may comprise inserting the expandable scraper through a lumen of the inverting thrombectomy apparatus.

In general, the expandable scrapers described herein may have a pore size and pulling stiffness that are within predefined functional ranges that permit them to be operated without jamming within the vessel or without damaging the vessel wall. Apparatuses having pore sizes or pulling stiffnesses that are outside of this range typically do not work, or do not work without damaging the vessel wall.

For example, described herein are expandable scraper devices having: an elongate shaft comprising an inner elongate member slidably disposed within an outer elongate member; an expandable braided basket coupled at a proximal end to a distal end region of the outer elongate member and at a distal end to a distal end region of the inner elongate member, wherein the expandable braided basket is formed of wires having a diameter of 0.15 mm or more (e.g., 0.2 or more) braided into a pattern having a pore area of between 1.2 and 7.5 mm$^2$ when the expandable braided basket is expanded to between 5 and 15 mm in diameter and has a maximum diameter in an expanded configuration of between 20 and 40 mm; and a proximal handle comprising a control configured to slide the inner elongate member relative to the outer elongate member to expand the expandable braided basket from an unexpanded configuration, further wherein the expandable basket is configured to have a pull force of between 0.18 and 0.4 pounds of force within a vessel when expanded against the vessel wall with a pull force of between about 0.3 and 0.6 pounds.

As mentioned, the diameter of the wires forming the basket may be 0.15 mm or more (e.g., 0.2 mm or more), particularly when braided into a pore area of between 1.2 and 7.5 mm$^2$ when expanded to between 5 and 15 mm in diameter (for baskets having a maximum expanded diameter of between 20-40 mm). This range of pore sizes may be optimal for scraping the walls of the lumen without damaging them, while still removing clot material. Outside of this range the braided basket may not function to scrape and remove clot material as described. For example, smaller pore sizes are not sufficiently abrasive to remove clot material, while larger pore sizes may be overly aggressive. Thus, the pore size may be optimized as described herein.

As used herein the term "pore size" in reference to a braided basket refers to the openings or pores formed between the wires of the braided basket. These pores may be rectangular (square, diamond-shaped, etc.) and may change size as the basket it expanded or contracted (collapsed). The wires may slide relative to each other when the basket is expanded or contracted.

In addition, the apparatuses and methods described herein may optimize the stiffness of the basket. For wires having a diameter of greater than 0.15 mm (e.g., between 0.15 mm and 0.25 mm), the braiding pattern, including pore size, may also help determine the stiffness. Ideally, the stiffness is such that when the basket is expanded with an expansion force of between about 0.2 and about 0.35 pounds of force within a vessel (e.g., expanded against the vessel wall), the basket may be withdrawn proximally with a pull force of between about 0.18 and 0.4 pounds. This range of pull force, when used to withdraw a basked configured as mentioned above (e.g., including the range of pore sizes) may result in scraping without overly damaging the vessel wall, and without jamming within the vessel wall.

In general, these expandable worn baskets may be formed of a biocompatible material having sufficient flexibility that it can form the expandable/collapsible basket without breaking. For example, the expandable basket may be formed of a shape-memory alloy (e.g., a superelastic alloy) such as nickel titanium. The expandable basket may be formed of a stainless steel material. In some examples the expandable basket may be formed of a polymeric material. As mentioned, the diameter of the wires of the expandable braided basket may be 0.15 mm or greater, and in particular, may be between 0.15 mm and 0.25 mm.

The elongate shaft of the expandable scraper device may be any appropriate length, such as, for example, between 100 and 150 cm. The expandable braided basket may have a length of, e.g., between 3 and 10 cm in the unexpanded configuration. The expandable braided basket may be formed of between 10 and 60 wires (e.g., between 20 and 60 wires, between 24 and 58 wires, etc.).

In general, the expandable braided basket may be loosely braided, so that the basket is configured to deform about a long axis. For example, the basket may be displaced laterally (e.g., to the side) when at least partially expanded (e.g., expanded 25% or more, 30% or more, 35% or more, 40% or more, 45% or more, 50% or more, etc.). The wires forming the basket may easily slide over each other so that the basket may have region of larger or smaller pore size. Thus, when describing the pore sizes of any of the baskets described herein, the pore size expressed may be an average pore size for the basket. The pore size described may refer to the maximum pore size. The pore size may refer to the pore size of a predetermined percentage of the basket, including in particular the middle region of the basket (which contacts the vessel wall when expanded, such as the middle 40% or more, the middle 50% or more, the middle 60% or more the middle 70% or more, etc.).

The control on the proximal handle may be a slider coupled to the inner elongate member. For example, the control on the proximal handle may be a slider including a button to lock/unlock (e.g., disengage/engage) a ratcheting lock in the handle, axially securing the inner member relative to the outer member.

The expandable braided basket may have a diameter of less than 1.1 mm in the unexpanded configuration.

Also described herein are methods of using any of these expandable scraper devices. For example, a method of removing a clot may include: positioning an expandable scraper device within a lumen of a vessel so that an expandable braided basket of the expandable scraper device is positioned distal to or within the clot; expanding the expandable braided basket against the wall of the vessel lumen with a radial force of between about 0.25 and 0.6 pounds of force against the wall of the vessel lumen, so that the expandable braided basket forms a pattern of pores having a pore area of between 1.2 and 7.5 mm$^2$; and pulling the expandable braided basket proximally with a pull force of between about 0.18 and 0.4 pounds to scrape clot material from the wall of the vessel lumen without damaging the wall of the vessel lumen.

As mentioned, any of these methods may include applying suction to remove the clot material from the vessel lumen. Alternatively or additionally, the method may include removing clot material from the vessel lumen using an inverting thrombectomy apparatus. Positioning the expandable scraper device within the lumen of the vessel may comprise inserting the expandable scraper device through an inverting thrombectomy apparatus. In some examples, positioning the expandable scraper device within the lumen of the vessel comprises inserting the expandable scraper device adjacent to an inverting thrombectomy apparatus. Positioning the expandable scraper device within the lumen of the vessel comprises inserting the expandable scraper device from a first access region in the vasculature and inserting an inverting thrombectomy apparatus through a second access region in the vasculature.

Also described herein are expandable scrapers that are configured to deflect off-axis during expansion, which may be particularly beneficial for allowing coaxial use in the vessel. For example, the expandable scraper may be inserted alongside other devices such as suction catheters and/or inverting thrombectomy apparatuses. These devices may be configured for off-axis expansion in part because of the flexibility of the central shaft and the flexibility of the wires forming the basket. The basket may be configured to have variable pore sizes and may be formed of thin wires that are loosely braided, as mentioned above. Thus, in general, any of these expandable scraper devices may include an expandable basket that is configured to deform in the expanded configuration into an off-axis shape.

For example, described herein are expandable scraper devices comprising: an elongate shaft comprising a flexible inner elongate member slidably disposed within a flexible outer elongate member; an expandable braided basket coupled at a proximal end to a distal end region of the outer elongate member and at a distal end to a distal end region of the inner elongate member, wherein the expandable braided basket is configured to deform in an expanded configuration so that a portion of the inner elongate member within the expandable braided basket is non-concentric with the expandable braided basket; a proximal handle comprising a control configured to slide the inner elongate member relative to the outer elongate member to expand or collapse the expandable braided basket.

As mentioned, in some examples the expandable braided basket may comprises a superelastic alloy material. The diameter of the wires of the expandable braided basket may be between 0.15 mm and 0.25 mm. the elongate shaft is between 100 and 150 cm. The expandable braided basket may have a length of between 3 and 10 cm in the unexpanded configuration. The expandable braided basket may be formed of between 20 and 60 wires. The control on the proximal handle may be a slider coupled to the inner elongate member. The expandable braided basket may have a diameter of less than 1.1 mm in the unexpanded configuration.

A method of removing clot may include: positioning an expandable scraper device within a lumen of a vessel so that an expandable braided basket of the expandable scraper device is positioned distal to or within the clot; expanding the expandable braided basket against the wall of the vessel lumen so that an inner elongate member slidably disposed within a flexible outer elongate member within the expandable braided basket is positioned within the expandable braided basket offset from a midline of the expandable braided basket; and pulling the expandable braided basket proximally to scrape clot material from the wall of the vessel lumen without damaging the wall of the vessel lumen. Pulling may comprise pulling with a pull force of between about 0.18 and 0.4 pounds.

As mentioned, any of these methods may include applying suction to remove the clot material from the vessel lumen and/or removing clot material from the vessel lumen using an inverting thrombectomy apparatus. Positioning the expandable scraper device within the lumen of the vessel may include inserting the expandable scraper device adjacent to an inverting thrombectomy apparatus.

Also described herein are expandable scrapers with a projection on the elongate shaft, such as (but not limited to) locking ring (e.g., ferrule) that is configured to adjust the pull length of the elongate body. The projection (e.g., locking ring) may releasably lock onto an engagement region of the proximal handle of the scarper which may effectively and efficiently shorten the length of the elongate shaft to allow the user (e.g., physician, technician, nurse, etc.) to operate the expandable scraper device more easily, with two or even one hand, when pulling the device proximally to withdraw clot material.

For example, described herein are expandable scraper devices including: an elongate shaft comprising an inner elongate member slidably disposed within an outer elongate member; one or more projections on the elongate shaft, wherein at least one of the oner or more projections is positioned in a middle region of the elongate shaft; an expandable braided basket coupled at a proximal end to a distal end region of the outer elongate member and at a distal end to a distal end region of the inner elongate member; a proximal handle comprising a control configured to slide the inner elongate member relative to the outer elongate member to expand the expandable braided basket from an unexpanded configuration; and a lock on the proximal handle configured to receive one of the one or more projections from a proximal direction and to releasably lock onto the projection as it is pulled distally, to form a loop of the elongate shaft and to decrease the effective length of the elongate shaft.

The projections may be any appropriate projection that may releasably engage with the lock on the proximal handle. For example, the one or more projections may be a ring. In some examples the one or more projections comprises a plurality of projections space over the length of the elongate shaft. In general, the projections may be arranged along the length of the elongate shaft at intervals configured to allow the shaft to be looped around one or more times in predetermined (or user-selected) lengths to shorten the effective length of the shaft. For example, the one or more projections may comprise a plurality of projections spaced apparat from each other by more than 10 cm (e.g., more than 15 cm, more than 20 cm, more than 25 cm, etc.).

The lock may generally be configured to releasably engage with the projection(s). For example, the lock may comprise a tapered channel on an outer surface of the proximal handle. In some examples the lock comprises a laterally-open channel on an outer side surface of the proximal handle; a portion of the elongate shaft may be inserted into the laterally-open channel until it engages with the projection, which may hold it in place (e.g., by sliding it distally).

A method of removing clot using an expandable scraper device that includes a projection and lock on the handle as described above may include: positioning an expandable scraper device within a lumen of a vessel so that an expandable braided basket of the expandable scraper device is positioned distal to or within the clot; expanding the expandable braided basket against the wall of the vessel lumen; pulling the expandable braided basket proximally to scrape clot material from the wall of the vessel lumen without damaging the wall of the vessel lumen; forming a loop of a portion of a proximal end of an elongate shaft of the expandable scraper; securing a projection extending from the elongate shaft within a lock formed on a handle of the expandable scraper device, so that the effective length of the expandable scraper device is shortened; and pulling proximally on the handle to pull the clot material proximally.

In general, securing the projection may comprise engaging the projection into an open, tapered channel on an outer surface of the handle. For example, securing the projection may comprise engaging a ring on the elongate shaft of the expandable scraper within a laterally open channel on an outer surface of the handle. Any of these methods may include applying suction to remove the clot material from the vessel lumen. Any of these methods may include removing clot material from the vessel lumen using an inverting thrombectomy apparatus.

As mentioned above, positioning the expandable scraper device within the lumen of the vessel may include inserting the expandable scraper device through an inverting thrombectomy apparatus. Alternatively, positioning the expandable scraper device within the lumen of the vessel may include inserting the expandable scraper device adjacent to an inverting thrombectomy apparatus. In some examples, positioning the expandable scraper device within the lumen of the vessel comprises inserting the expandable scraper device from a first access region in the vasculature, and inserting an inverting thrombectomy apparatus through a second access region in the vasculature.

Also described herein are method of manually adjusting the diameter of the basket as it is pulled through a vessel (to remove clot) in a manner that maintains the force, e.g., the pull force or drag force, within the lumen of the vessel within a range. For example, any of these apparatuses may include a control on the handle, as mentioned above, which locks and/or unlocks the expansion of the expandable basket, by controlling axial (sliding) movement of the inner elongate member slidably relative to the outer elongate member. This control may include a button (e.g., a release) on the handle.

For example, described herein are methods of removing clot, the method comprising: positioning an expandable scraper device within a lumen of a vessel so that an expandable braided basket of the expandable scraper device is positioned distal to or within the clot; expanding the expandable braided basket against the wall of the vessel lumen with a radial force of between about 0.25 and 0.6 pounds of force against the wall of the vessel lumen; and pulling the expandable braided basket proximally while adjusting the pull force by operating a control on a handle of the expandable scraper device to expand or contract the expandable braided basket to maintain the pull force between about 0.2 and 0.8 pounds (e.g., between about 0.18 and 0.4 pounds) of force to scrape clot material from the wall of the vessel lumen without damaging the wall of the vessel lumen.

In general, pulling the expandable braided basket proximally may include maintaining the pull force at an approximately constant level. Operating the control on the handle of the expandable scraper device may include releasing a ratcheting lock on the handle to expand and contract the expandable scraper device.

Any of these methods may include applying suction to remove the clot material from the vessel lumen and/or removing clot material from the vessel lumen using an inverting thrombectomy apparatus. Positioning the expandable scraper device within the lumen of the vessel may comprise inserting the expandable scraper device through an inverting thrombectomy apparatus or inserting the expandable scraper device adjacent to an inverting thrombectomy apparatus. Positioning the expandable scraper device within the lumen of the vessel may comprise inserting the expandable scraper device from a first access region in the vasculature and inserting an inverting thrombectomy apparatus through a second access region in the vasculature.

Any of the scraper devices described herein may be configured as an off-axis scraper. For example, an expandable scraper device may include: an elongate shaft comprising a flexible inner elongate member slidably disposed within a flexible outer elongate member; an expandable braided basket coupled at a proximal end to a distal end region of the flexible outer elongate member and at a distal end to a distal end region of the flexible inner elongate member, wherein the expandable braided basket is configured to deform from an unexpanded configuration of wires into an expanded configuration so that a portion of the flexible inner elongate member within the expandable braided basket is non-concentric with the expandable braided basket; and a proximal handle comprising a control configured to slide the flexible inner elongate member relative to the flexible outer elongate member to expand the expandable braided basket. In general, an off-axis scraper may include an expandable basket (scraper) in which an elongate shaft passing through the expandable basket, and typically to which one of the ends of the braided basket are attached to allow control of expansion/collapse, not in line with long axis (distal-to-proximal) midline through the expandable basket. In many of the off-axis scrapers described herein, the elongate shaft (e.g., an inner shaft) is radially offset, e.g., by more than about 50% of the radius of the expandable basket, when expanded (e.g., by more than 55% by more than 60%, by more than 70%, by more than 75%, etc.).

Such off-axis scrapers may have many advantages as compared with other scrapers in which the expandable basket include a on-axis (concentrically arranged) inner elongate member. For example, off-axis scrapers may allow adjacent proximal deployment of a second tool, such as a suction catheter or inverting tube apparatus.

For example, described herein are expandable scraper devices, the device comprising: an elongate shaft comprising a flexible inner elongate member slidably disposed within a flexible outer elongate member; an expandable braided basket coupled at a proximal end to a distal end region of the flexible outer elongate member and at a distal end to a distal end region of the flexible inner elongate member having a length of between 3 and 10 cm in an unexpanded configuration, wherein the expandable braided basket is formed of between 20 and 60 nickel titanium wires each having a diameter of between 0.15 mm and 0.35 mm, and is configured to deform from the unexpanded configuration into an expanded configuration so that a portion of the flexible inner elongate member within the expandable braided basket is non-concentric with the expandable braided basket, further wherein the expandable braided basket is shape set to return to the unexpanded configuration in an unconstrained state; and a proximal handle comprising a control configured to slide the flexile inner elongate member relative to the outer flexible elongate member to expand the expandable braided basket.

Also described herein are methods of removing clot using any of these devices. For example, a method may include: positioning an expandable scraper device within a lumen of a vessel so that an expandable braided basket of the expandable scraper device is positioned distal to or within the clot; expanding the expandable braided basket against a wall of the vessel lumen by adjusting a control on a proximal handle of the expandable scraper device, so that an inner elongate member that is slidably disposed within a flexible outer elongate member and within the expandable braided basket is positioned within the expandable braided basket offset from a midline of the expandable braided basket; and pulling the expandable braided basket proximally to scrape clot material from the wall of the vessel lumen without damaging the wall of the vessel lumen.

In some examples the method may include adjusting (e.g., manually, automatically or semi-automatically) the diameter of the basket as it is pulled to maintain force within a range. For example, a method of removing clot may include: positioning an expandable scraper device within a lumen of a vessel in an unexpanded configuration so that an expandable braided basket of the expandable scraper device is positioned distal to or within the clot; expanding the expandable braided basket to an expanded configuration against a wall of the vessel lumen where the expandable braided basket is configured to apply a maximum scraping force against the wall of the vessel lumen of 1.5 pounds of force or less; and pulling the expandable braided basket proximally while adjusting a pull force by operating a control on a handle of the expandable scraper device to expand or contract the expandable braided basket to maintain the pull force between about 0.2 and 1.5 pounds of force to scrape clot material from the wall of the vessel lumen without damaging the wall of the vessel lumen.

The expandable braided basket comprises expanding the expandable braided basket against a bias force configured to return to the expandable braided basket to the unexpanded configuration in an unconstrained state. Expanding the expandable braided basket may include expanding the expandable braided basket from a length of between 3 and 10 cm in the unexpanded configuration. In some examples, expanding the expandable braided basket comprises expanding a braid of between 20 and 60 nickel titanium wires each having a diameter of between 0.15 mm and 0.35 mm into the expanded configuration. For example, expanding may comprise expanding the expandable braided basket so that an inner elongate member which extends between a distal end of the expandable braided basket and a proximal end of the expandable braided basket is positioned within the expandable braided basket offset from a midline of the expandable braided basket.

Adjusting the pull force by operating the control on the handle of the expandable scraper device may include operating a finger slider to manually adjust expansion of the expandable braided basket to maintain the pull force between about 0.2 and 1.5 pounds of force. In some examples adjusting the pull force by operating the control on the handle of the expandable scraper device comprises operating both a release button and a finger slider to manually adjust expansion of the expandable braided basket to maintain the pull force between about 0.2 and 1.5 pounds of force. Adjusting the pull force by operating the control on the handle of the expandable scraper device may include releasing a ratcheting lock on the handle to expand or contract the expandable braided basket.

Any of these methods may include providing feedback of the pull force applied (e.g., visual, tactile and/or audible feedback). For example, the apparatus may include a force sensor and may provide visible feedback such as a display and/or one or more LED lights). In some examples, the apparatus may display when the force being applied is between the target range (e.g., between 0.2 and 1.5 pounds). In any of these examples the apparatus may be configured to limit the applied force to prevent it from exceeding the maximum force, such as 1.5 pounds.

Any of these methods may include applying suction to remove clot material from the vessel lumen. For example, any of these methods may include pulling the expandable braided basket proximally comprises maintaining the pull force at an approximately constant level. For example, any of these methods may include positioning the expandable scraper device within the lumen of the vessel comprises inserting the expandable scraper device through a catheter and pulling the expandable braided basket with clot to a distal tip of the catheter and aspirating clot through the catheter.

The methods described herein may include repeatedly positioning the expandable scraper device within the lumen of the vessel to scrape a same location of the vessel by advancing the expandable scraper over a guidewire in the collapsed configuration, expanding the expandable scraper, and pulling the expandable braided basket proximally while adjusting a pull force.

Pulling the expandable braided basket proximally may include adjusting the pull force by operating a control on a handle of the expandable scraper device to expand or contract the expandable braided basket to maintain the pull force between about 0.2 and 1.5 pounds of force to scrape clot material from the wall of the vessel lumen without damaging the wall of the vessel lumen as a diameter of vessel walls change along a length of the vessel walls.

For example, a method of removing clot may include: positioning an expandable scraper device within a lumen of a vessel in an unexpanded configuration so that an expandable braided basket of the expandable scraper device is positioned distal to or within the clot; expanding the expandable braided basket against a wall of the vessel lumen where the expandable braided basket is configured to apply a maximum scraping force against the wall of the vessel lumen of 1.5 pounds of force or less, further wherein the expandable braided basket is biased to return to the unexpanded configuration in an unconstrained state, and wherein the expandable braided basket has a length of between 3 and 10 cm in the unexpanded configuration, wherein the expandable braided basket is formed of between 20 and 60 nickel titanium wires each having a diameter of between 0.15 mm and 0.35 mm; and pulling the expandable braided basket proximally while adjusting a pull force by operating a control on a handle of the expandable scraper device to expand or contract the expandable braided basket to maintain the pull force between about 0.2 and 1.5 pounds of force to scrape clot material from the wall of the vessel lumen without damaging the wall of the vessel lumen.

For example, a method of removing clot may include: positioning an expandable scraper device within a lumen of a vessel in an unexpanded configuration so that an expandable braided basket of the expandable scraper device is positioned distal to or within the clot; expanding the expandable braided basket against a wall of the vessel lumen where the expandable braided basket is configured to apply a maximum scraping force against the wall of the vessel lumen of 1.5 pounds of force or less, further wherein the expandable braided basket expanded against a bias force configured to return to the expandable braided basket to the unexpanded configuration in an unconstrained state; and pulling the expandable braided basket proximally while adjusting a pull force by operating a control on a handle of the expandable scraper device to expand or contract the expandable braided basket to maintain the pull force between about 0.2 and 1.5 pounds of force to scrape clot material from the wall of the vessel lumen without damaging the wall of the vessel lumen, wherein adjusting the pull force by operating the control on the handle of the expandable scraper device comprises releasing a ratcheting lock on the handle and sliding a slider to expand or contract the expandable braided basket.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative examples, and the accompanying drawings of which:

FIG. 14 shows one example of a braided material that may be used to form a distal expanding (scraper) region of an expandable scraper (or backstop) as described herein. In FIG. 14, the braid is made up of a combination of flat and rounded wires.

FIG. 15 shows an example of a braided material that may be used to form a distal expanding (scraper) region of an expandable scraper (or backstop) as described herein. In FIG. 15, the braid is made up of a combination of flat and rounded wires and a knit cover, which may provide a texture to the surface.

FIG. 16 is another example of a region that may be used as a distal expanding (scraper) region of an expandable scraper device as described herein.

FIG. 19A-19D illustrate one example of an expandable scraper device as described herein. FIG. 19A shows a side perspective view. FIG. 19B shows a view of the proximal handle of the expandable scraper device of FIG. 19A. FIG. 19C shows region of the elongate shaft of the expandable scraper device of FIG. 19A. FIG. 19D shows the expandable basket at the distal end of the expandable scraper device of FIG. 19A.

FIG. 20A shows the basket in a collapsed (non-expanded) configuration. FIG. 20B shows the basket in an expanded configuration. FIG. 20C shows the distal end region of the expandable scraper device.

FIGS. 24A-24E illustrate details of one example of a proximal handle of an expandable scraper device as described herein. FIG. 24A shows a perspective view of the handle. FIG. 24B shows a partially transparent view into the handle of FIG. 24A. FIG. 24C shows an enlarged view of the ratcheting lock portion of the handle of FIGS. 24A-24B. FIG. 24D shows an enlarged view of the proximal end region of the handle of FIG. 24A. FIG. 24E shows an enlarged view of the controls controlling expansion/contraction of the expandable scraper device.

FIG. 27A shows a perspective view of the handle. FIG. 27B shows an enlarged side view of the engagement region. FIG. 27C illustrates the use of the engagement region to shorten (by forming a loop) the elongate shaft of the expandable scraper device.

FIGS. 29A-29E illustrate methods of delivering the devices described herein into the target region of the vasculature.

In FIG. 30A, the assembled apparatus is shown in a side view, showing an inversion support catheter and a flexible outer tube. FIG. 30B shows the inverting tube apparatus of FIG. 30A in a vessel, proximal to a clot.

FIG. 30C illustrates the removal of a clot from the vessel using the apparatus of FIG. 30A, by pulling the flexible tube on the outside of the inversion support catheter proximally so that it rolls over the distal end of the inversion support catheter and into the inversion support catheter, drawing the clot with it; the apparatus may be advanced distally.

DETAILED DESCRIPTION

The methods and apparatuses described herein may also relate to removal of clot material, and in particular, to scraping apparatuses for assisting in removing clot material from within the walls of a vessel. The apparatuses and method described herein may be used with any apparatus for removing clot material, including suction (e.g., suction catheters) and inverting tube apparatuses for removing material from within a body.

Any of the features, components and techniques described herein may be used separately or in combination.

For example, described herein are expandable scrapers that may assist in removing material (e.g., clot material) from within a lumen so that it may be captured for removal, e.g., by any appropriate clot removal/capture device or technique. In particular, these devices may be used with suction (e.g., suction catheters) and/or with an inverting thrombectomy apparatus. For example, any of these methods and apparatuses may include passing an expandable scraper distally into (or just distal to) a clot or portion of a clot, and expanding the expandable scraper, and pulling it proximally to remove or dislodge the clot material from the vessel wall so that it may be captured and removed. These steps may be repeated using the apparatuses described herein.

For examples, scraping the vessel wall with an expandable scraper and/or securing it in place with an expandable backstop may be used before or during use with a suction tube and/or with an inverting thrombectomy apparatus. In some examples the scraper and/or backstop may be integrated into the inverting thrombectomy apparatus and/or method. For example, an expandable scraper and/or backstop may help gather clot material for capture by the inverting thrombectomy apparatus. The expandable scraper and/or backstop may detach or dislodge material, including thrombus material, from the wall of the vessel.

Figure 1:
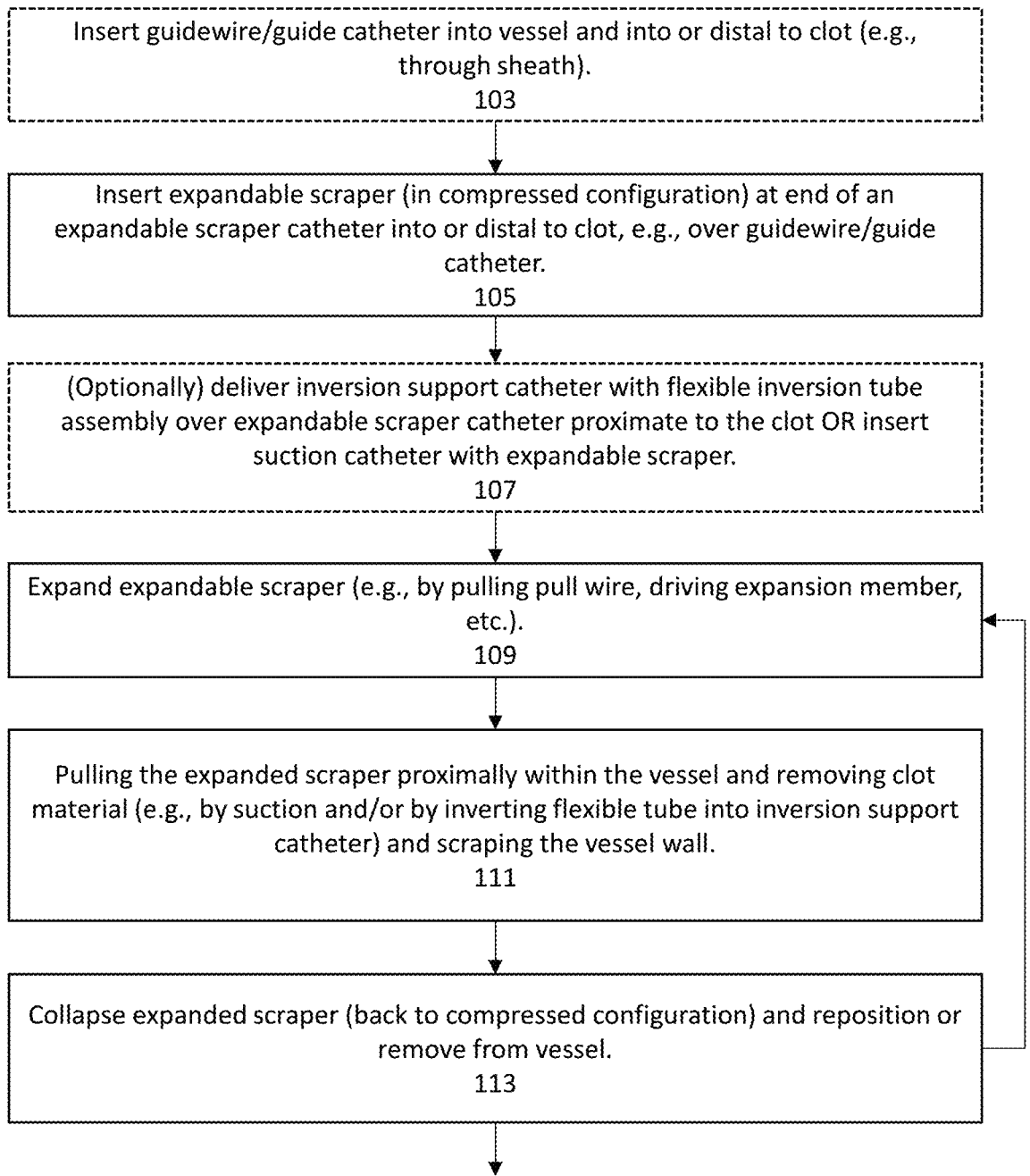
FIG. 1 schematically illustrates one example of a method of using an expandable scraper and/or backstop as described herein.

In general, a method of using a scraper may include positioning the expandable scraper, in a compressed, undeployed configuration, in position within a vessel, preferably near the clot material to be removed (e.g., distal to it, where distal is further from the insertion direction, and proximal is towards the insertion direction). FIG. 1 illustrates one example of a method of using a scraper with an inverting thrombectomy apparatus. In some cases, it may be desirable to optionally insert a guidewire (or guide catheter) into the vessel to be treated, and into or distal to a clot material before inserting the expandable scraper 103. Alternatively, the expandable scraper may itself act as the guidewire or guide catheter. The expandable scraper may include a distal expanding (scraping) region and a proximal elongate body (e.g., wire, catheter, etc.). The expandable scraper may be inserted, e.g., through a sheath hub, into the body vessel in a compressed (undeployed) configuration so that the distal end of the expandable scraper is into or distal to clot 105. In some examples the inverting thrombectomy apparatus (including an inversion support catheter with a flexible tube, as described above) may be inserted over the elongate body of the expandable scraper so that the distal end of the inversion support catheter is proximate to the proximal end of the clot, with clot material between the distal expanding (scraping) region of the expandable scraper and the distal end of the inversion support catheter 107.

The distal expanding (scraping) region of the expandable scraper may be expanded into or behind the clot 109, for example, by releasing a self-expanding distal expanding (scraping) region or by actively expanding the distal expanding (scraping) region, e.g., by pulling on an actuator (e.g., pull wire, tendon, driving expansion member, etc.) 109. In examples in which the expandable scraper is used with the inverting thrombectomy apparatus, the distal expanding (scraping) region may be expanded either before and/or during delivery of the inverting thrombectomy apparatus.

The expanded distal expanding region may then be pulled proximally within the vessel so that clot material is removed from the walls of the vessel 111. In some examples, clot material may be removed by actuating the inverting thrombectomy apparatus, e.g., by pulling proximally on the puller to invert and roll the flexible tube into the inversion support catheter, as described above. In some examples the inverting thrombectomy apparatus may be actuated concurrently with the expandable scraper. For example, the proximal end of the puller and the expandable scraper may be moved concurrently (and may be coupled together); the distal end of the inversion support catheter may also be advanced distally at the same time. Alternatively, the distal end of the inversion support catheter may be held in position and the expandable scraper may be pulled proximally to drive clot material into the actuated inverting thrombectomy apparatus. Alternatively or additionally, clot material may be removed by suction. Thus, the expandable scraper may scrape the vessel wall. In some examples the expandable scraper may be collapsed again (e.g., by actuating, e.g., pulling proximally) the actuator and may be advanced again distally into or beyond additional clot material, repeating the process. The inverting thrombectomy apparatus may be removed over the expandable scraper and reloaded or reset, as described above, then repositioned over the expandable scraper. In some examples the expandable basket forming the scraper may be shape-set in a collapsed configuration, and force may be applied to expand the basket, as described herein; this may make resetting and repeating the process possible.

In some examples the expandable device may be an expandable backstop, rather than an expandable scraper may be configured as a backstop that prevents the clot from moving away from the distal end of the inverting thrombectomy apparatus as it is advanced. In this example, the expandable backstop may be held in a relatively static position relative to the vessel while the inverting thrombectomy apparatus is advanced distally.

In some examples the expandable device may operate as both an expandable backstop and an expandable scraper. For convenience, the same device may be referred to as an expandable scraper herein.

The expandable scraper (or expandable backstop) may be removed from the vessel before, during or after use with an inverting thrombectomy apparatus. For example, the expandable scraper may be collapsed from the expanded, deployed configuration back to the compressed (un-deployed) configuration and repositioned or removed from the vessel, as mentioned above 113.

Figure 2:
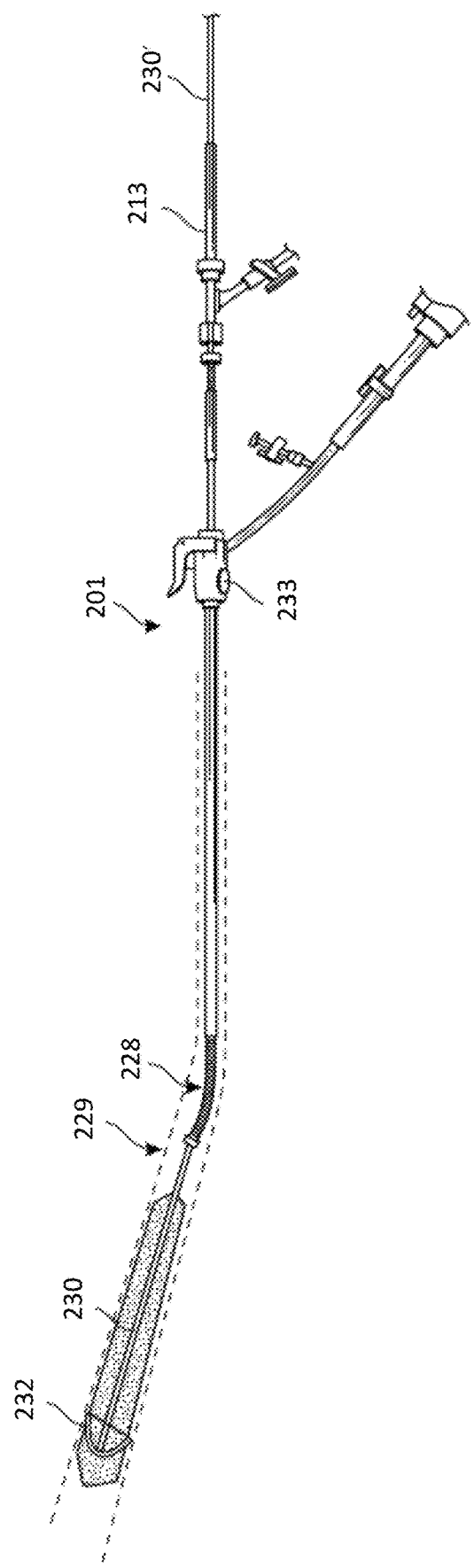
FIG. 2 illustrates an example of a system including an expandable scraper device and an inverting tube apparatus as described herein.

FIG. 2 illustrates one example of a system including both an inverting thrombectomy apparatus and an expandable scraper, as described herein. In FIG. 2, the inverting thrombectomy apparatus 201 is shown deployed within a vessel proximate to a clot 230. An expandable scraper 220 is shown deployed through the inverting thrombectomy apparatus and into the clot, and expanded within the clot, as described above. The inverting thrombectomy apparatus generally includes any of the features discussed above, including an inversion support catheter, a flexible (e.g., knitted) tube 228 inverted over the distal end 229 of the inversion support catheter, and a puller 213. The expandable scraper 230 is deployed through the inverting thrombectomy apparatus (e.g., through the flexible tube and inversion support catheter) and includes a distal expanding (scraping) region ("distal expanding region") 232. The inverting thrombectomy apparatus and expandable scraper may be deployed through a sheath hub 233.

FIGS. 3A-3D, 4A-4D, 5A-5C, 6, 7, 8, 9A-9C, 16 and 17 all illustrate examples of expandable scrapers as described herein. Features of any of these devices may be recombined with each other and/or combined with one or more of the inverting thrombectomy apparatuses described herein.

Figure 3A:
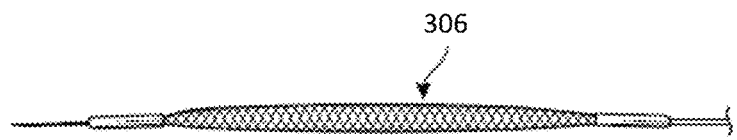
FIGS. 3A-3D illustrate an example of an expandable scraper device as described herein.
Figure 3B:
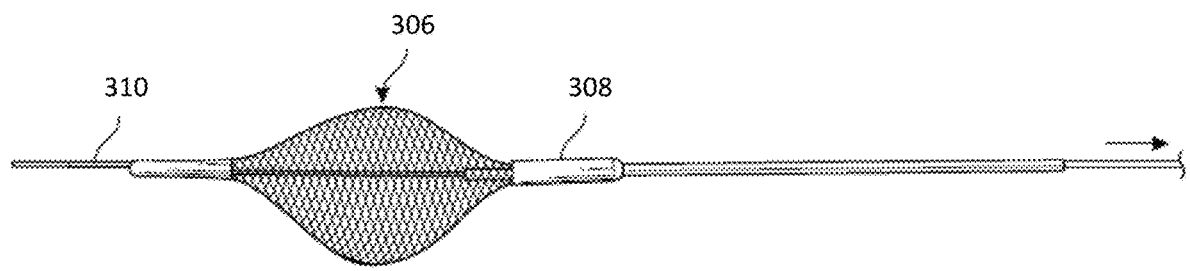
Figure 3C:
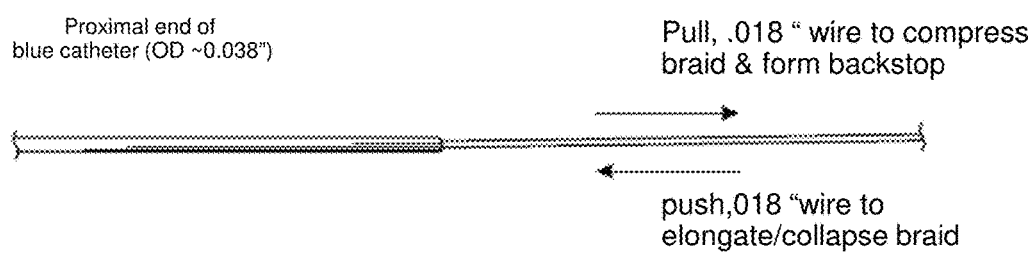

For example, FIGS. 3A-3B illustrate examples of an expandable scraper (which may also be an expandable backstop). In this example, the expandable scraper includes a distal expanding (scraping) region 306 formed of a knitted, braided or braided material that is attached to the wire (or catheter) 310 at the distal end and to a proximal catheter 308 that is slidably positioned over the wire (or catheter) at the proximal end. As shown in FIG. 3B, the device may be deployed from the collapsed delivery configuration shown in FIG. 3A by pushing the proximal catheter distally, expanding the distal expanding (scraping) region. The distal expanding (scraping) region may be preset (biased) to expand or to be in the collapsed configuration. FIG. 3C illustrates actuating of the distal expanding (scraping) region from the proximal region. The proximal catheter may have an OD of less than 0.38". The device may be actuated by either pushing the inner (wire) or pulling the outer proximal catheter to expand the distal expanding (scraping) region.

Figure 3D:
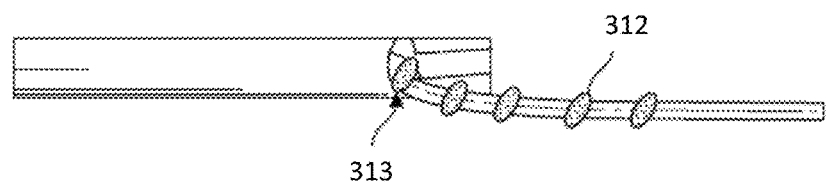

In some examples, the expandable scraper may be locked in the expanded and/or collapsed configuration. For example, FIG. 3D illustrates one example of a locking mechanism for an expandable scraper in which the scraper is biased (e.g., by shape setting) to be in an un-expanded configuration. The inner wire may be pulled relative to the proximal catheter to expand and may be held in the expanded (with the distal expanding region expanded) by engaging a locking protrusion 312 into a matching catch 313 on the catheter, as shown.

For example, in operation the expandable scraper may be delivered to the region of the clot and through the clot through a sheath hub in the collapsed configuration. In some examples the inverting atherectomy apparatus may be introduced over the expandable scraper. Before, during or after introducing the inverting atherectomy apparatus over the expandable scraper, the expandable scraper may be deployed, e.g., by pulling the wire as described in FIG. 3D.

Figure 4A:
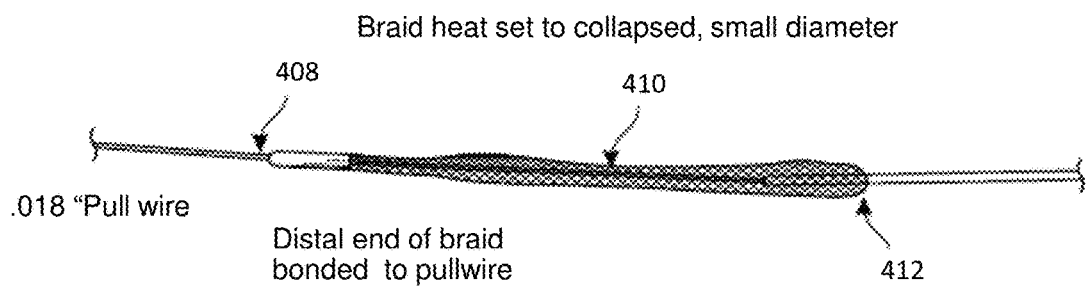
FIGS. 4A-4D illustrate an example of an expandable scraper device as described herein.
Figure 4B:
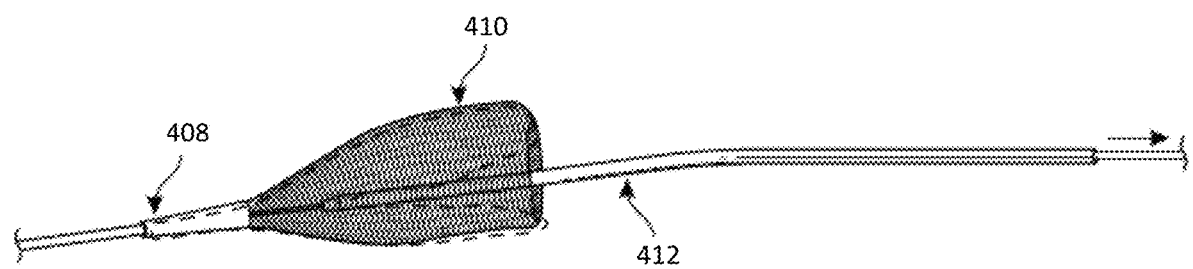
Figure 4C:
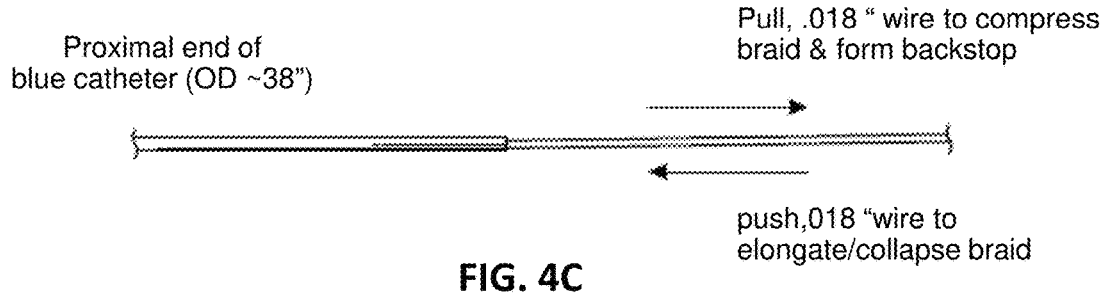
Figure 4D:
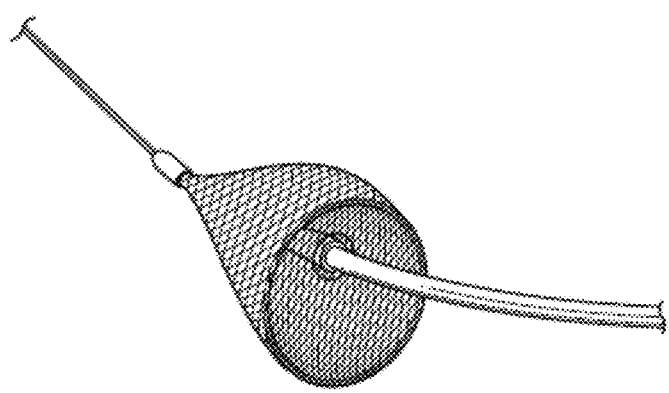
Figure 5A:
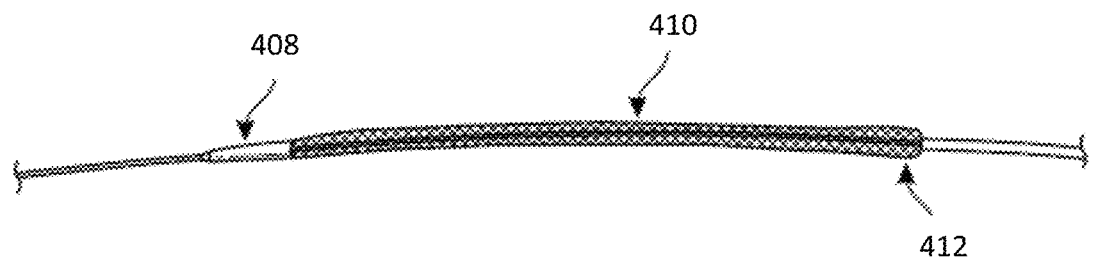
FIGS. 5A-5C illustrate an example of an expandable scraper device as described herein.
Figure 5B:
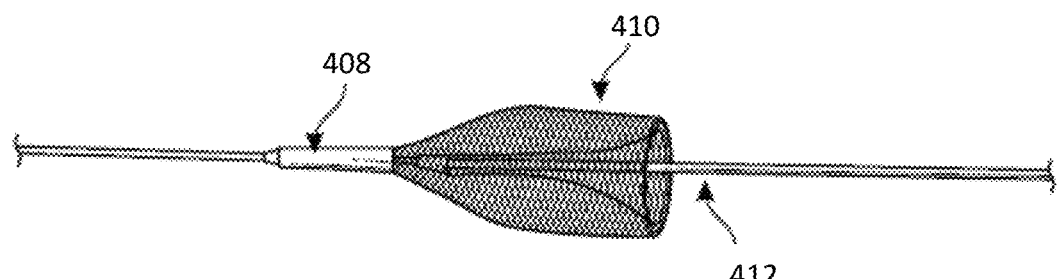
Figure 5C:
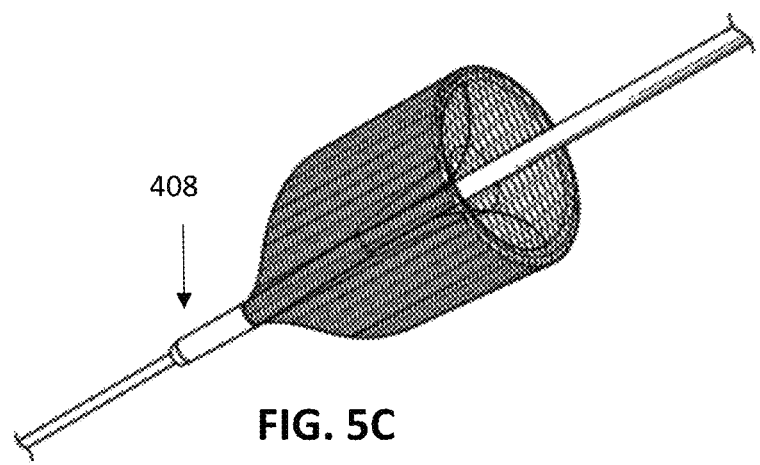

FIGS. 4A-4D illustrate another example in which the distal expanding (scraping) region is configured to assume a funnel shape. FIG. 4A shows the device in an un-deployed configuration, collapsed for insertion into the body. The distal end of the distal expanding (scraping) region is attached distally to a pull wire (e.g., a 0.018" pull wire) 408, and the distal expanding (scraping) region 410 is formed of a heat-set braid or braided material having a small collapsed diameter. The proximal end of the distal expanding (scraping) region is inverted and coupled to a catheter 412 (e.g., a catheter having an outer diameter of 0.038"). FIG. 4B illustrates actuation and expansion of the distal expanding (scraping) region of the device of FIG. 4A. By pulling the inner pull-wire 408 proximally relative to the outer catheter 412, the funnel shape is formed. This is shown in FIG. 4D fully deployed. FIG. 4C illustrates actuation of the proximal end. FIGS. 5A-5B illustrate another example similar to that shown in FIGS. 4A-4D. FIG. 5A shows the device in a collapsed configuration, while FIGS. 5B and 5C show the expanded configuration in which the scraper is inverted back into itself. The proximal end (couped to the catheter 412) is within the inverted basket. The basked may be deployed either by pushing the proximal end distally relative to the distal end, or by pulling the distal end proximally relative to the proximal end.

Figure 6:
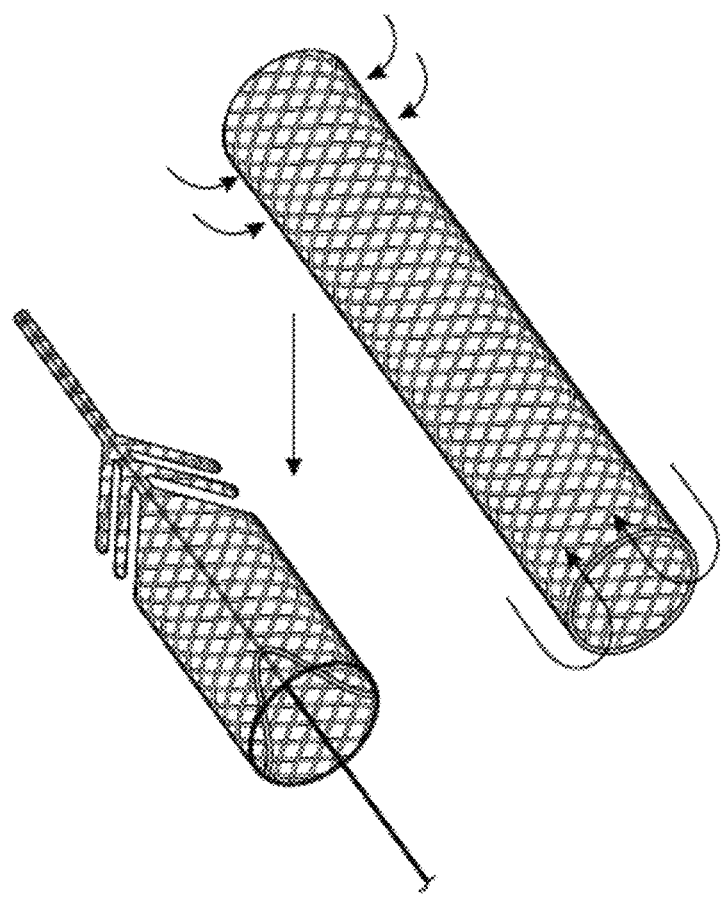
FIG. 6 shows schematics of an example of an expandable scraper device as described herein.
Figure 7:
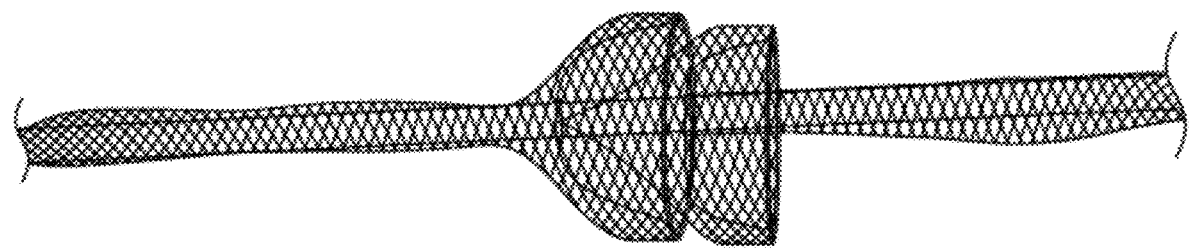
FIG. 7 is an example of an expandable scraper device as described herein.
Figure 8:
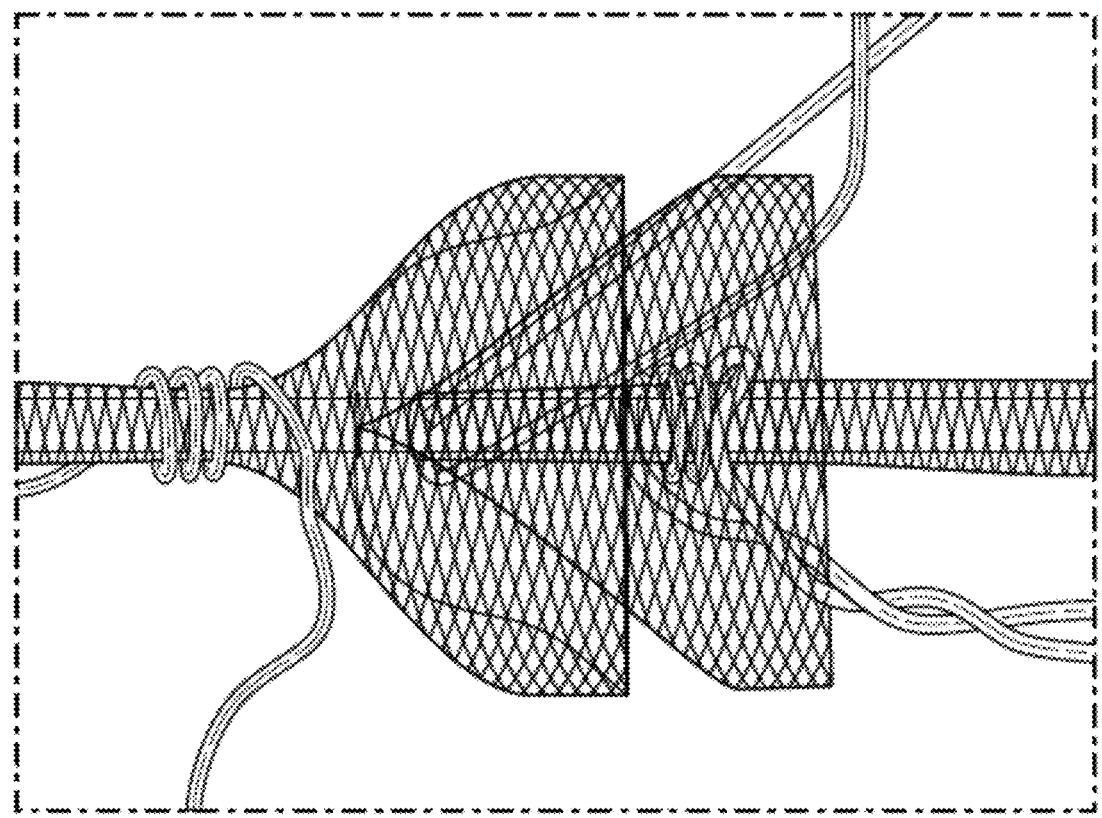
FIG. 8 is an example of an expandable scraper device as described herein.

FIG. 6 schematically illustrates examples of expandable scrapers having multiple (e.g., 2, 3, 4, 5, etc.) collapsible funnels forming the distal expanding (scraping) region. In FIG. 6, three funnel regions are formed similar to that shown in FIGS. 4A-4D and 5A-5C. FIGS. 7 and 8 illustrate examples of dual funnel distal expanding (scraping) regions.

Figure 9A:
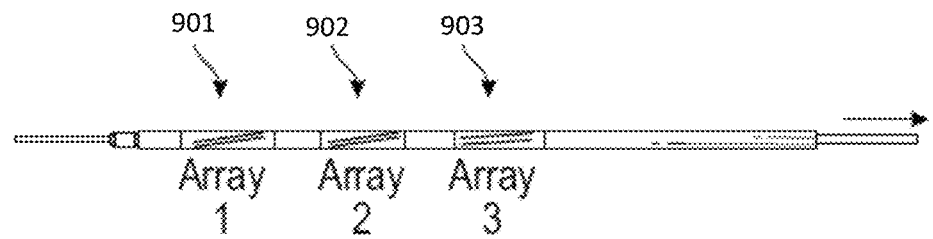
FIGS. 9A-9C illustrates another example of an expandable scraper device as described herein.
Figure 9B:
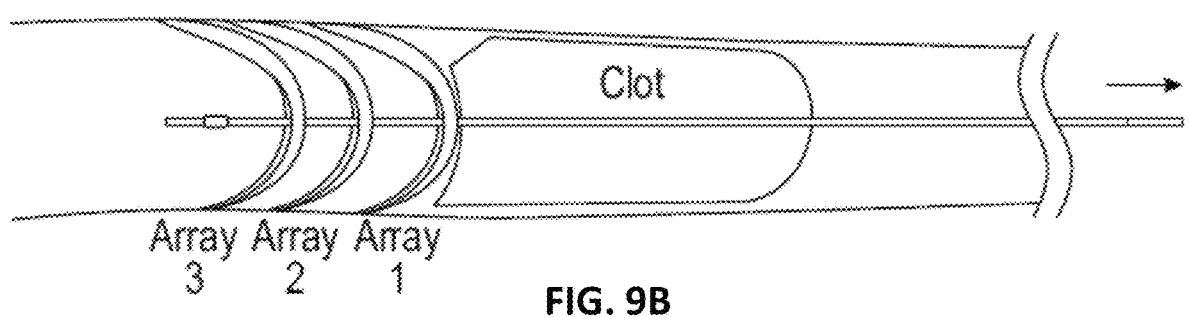
Figure 9C:
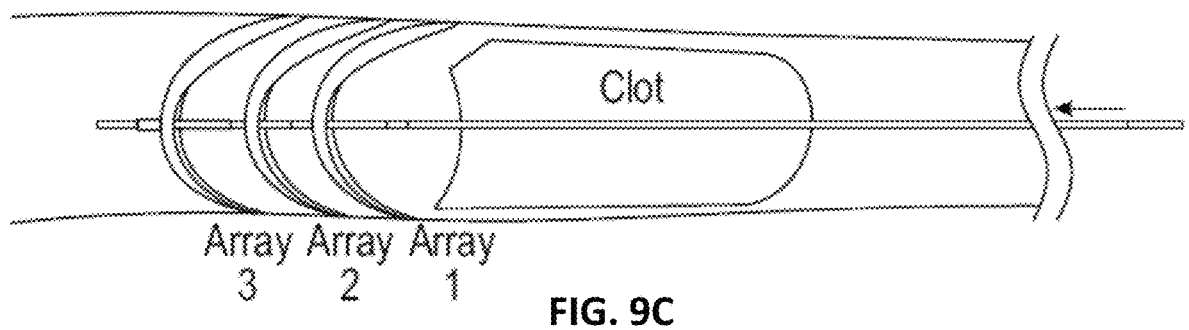

FIGS. 9A-9C illustrate an example of an expandable scraper having three distal expanding regions 901, 902, 903. These regions maybe expanded for more or less aggressive scraping based on the direction in which they are expanded. For example, FIG. 9B shows expansion in which the distal expanding members are concave facing away from the proximal direction (in some examples, away from the inverting thrombectomy apparatus, e.g., by pulling the pull wire of the device proximally and pinning the proximal catheter. In contrast, FIG. 9C shows an example in which the distal expanding members are concave facing towards the proximal direction (in some examples, towards the inverting thrombectomy apparatus, e.g., by pulling the catheter of the device proximally and pinning the pull wire.

Figure 17A:
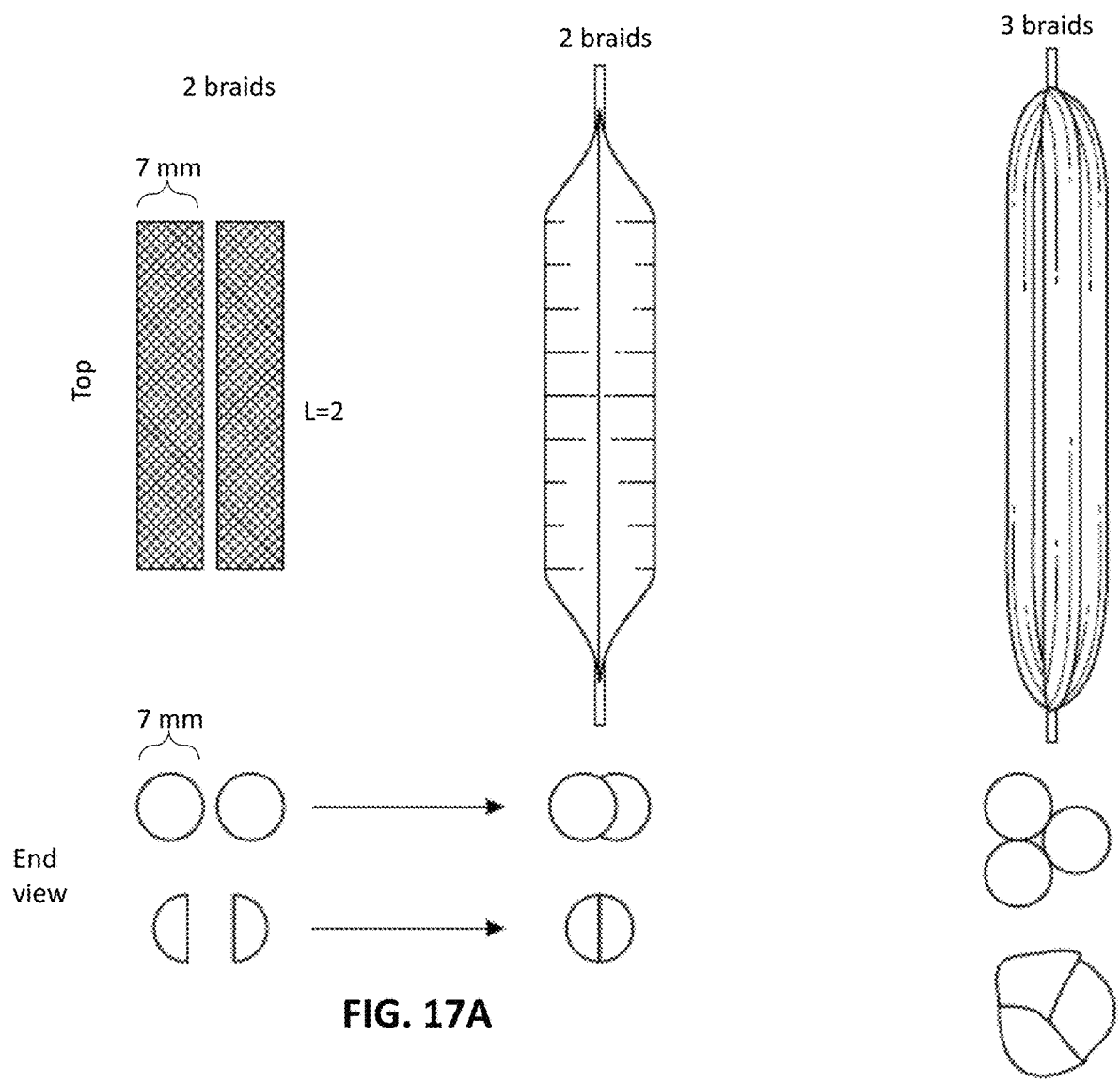
FIGS. 17A-17C illustrate various concepts that may be used for distal expanding regions of an expandable scraper device as described herein.
Figure 17B:
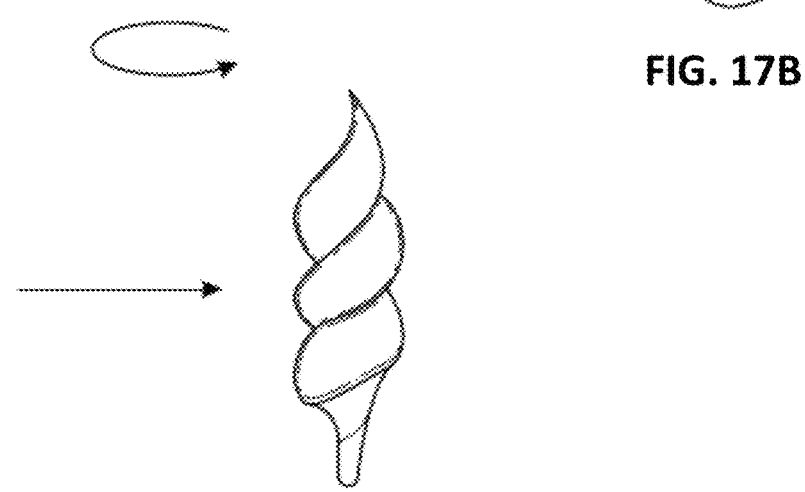
Figure 17C:
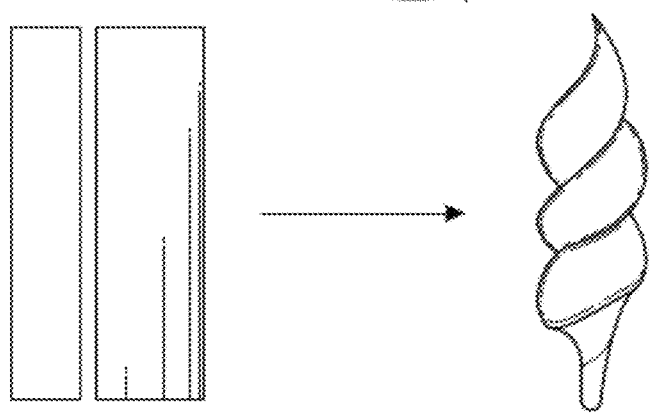

FIG. 16 shows another example of a structure (having a basket-like configuration, that may be used as a distal expanding (scraper) region of a scraper as described herein. FIGS. 17A-17C illustrates various features that may be included as a scraper of a distal expanding (scraper) region, including tubes (e.g., cylinders) divided longitudinally into two (FIG. 17A) or three (FIG. 17B) portions or regions, and/or twisted (FIG. 17C).

FIGS. 10A-10B, 11A-11B, 12A-12B, and 13A-13B all illustrate examples of expandable backstops as described herein. Features of any of these expandable backstop devices may be recombined with each other, with any features of the expandable scrapers, and/or combined with one or more of the inverting thrombectomy apparatuses described herein.

Figure 10A:
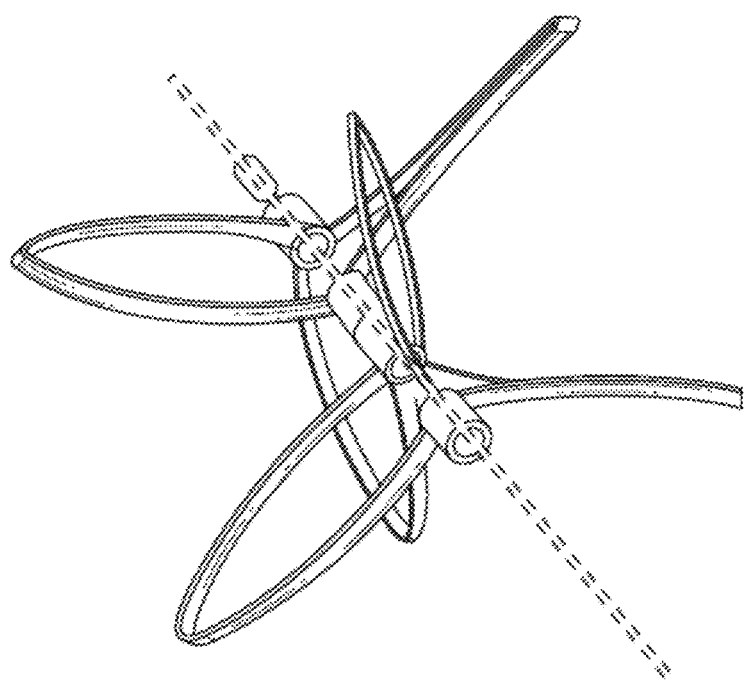
FIGS. 10A-10B show one example of an expandable backstop device as described herein.
Figure 10B:
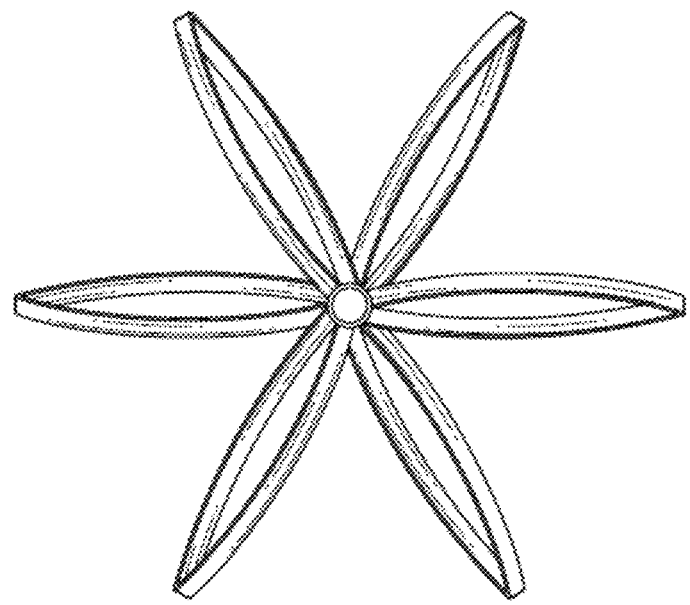

FIG. 10A shows an example of an expandable backstop that includes two pairs of three legs that may controllably expand outwards, as shown in the end-on view of FIG. 10B. The legs that expand outwards may be formed from a laser-cut hypotube. The distal expanding region may be actuated by pulling on a pull wire within the hypotube. In some examples the device is configured to return to the collapsed configuration when tension is released from the pull wire.

Figure 11A:
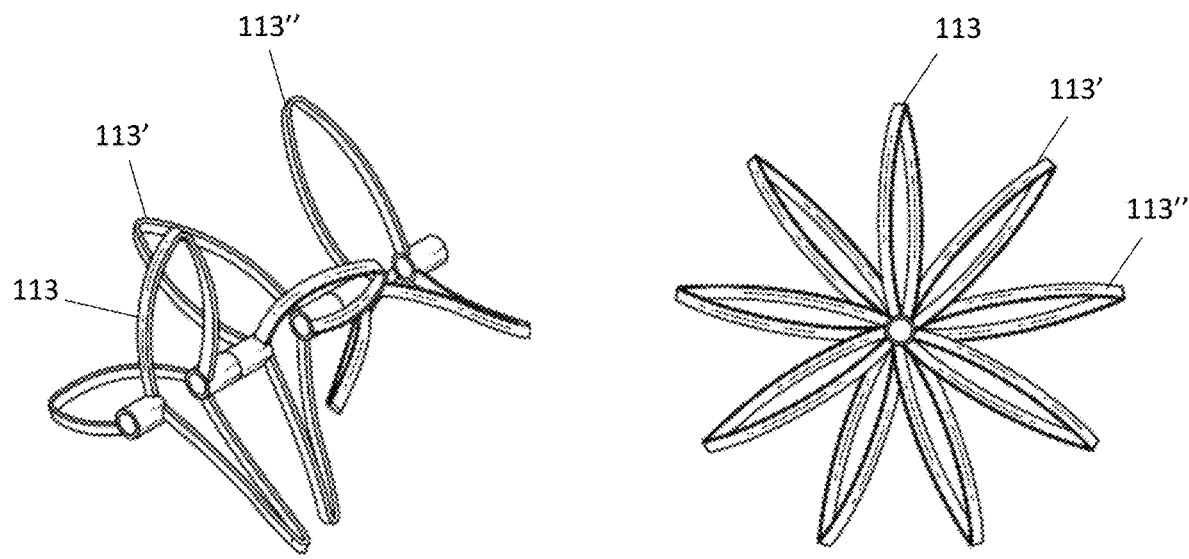
FIGS. 11A-11B illustrate an example of an expandable backstop device as described herein.
Figure 11B:
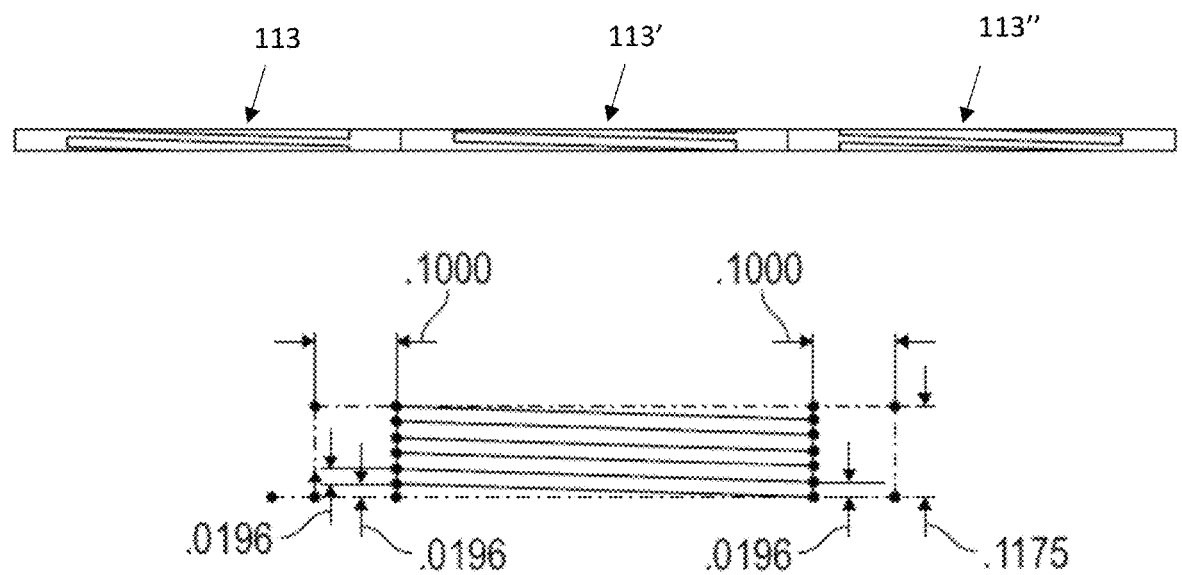

FIGS. 11A and 11B shows another example of an expandable backstop that includes three adjacent regions of three expandable "legs" each. The expanded diameter may be approximately 14 mm when maximally expanded. FIG. 11B shows the expandable backstop in an un-deployed configuration. The thin struts (legs 113, 113', 113") (e.g., approximately 0.019") may be helically arranged with three sections cut into a tube (e.g., OD 0.0374" with 0.00595" wall and inner diameter of 0.0255"). The dimensions show an example only, and other dimension may be used (e.g., +/−5%, 10%, 25%, 50%, 70%, 100%, etc. of the dimensions shown). In FIG. 11B the second section including struts 113' is rotated 40 degrees counter-clockwise in reference to the first section including struts 113, and the third section including struts 113" is rotated 80 degrees counter-clockwise in reference to the first section including struts 113.

Figure 12A:
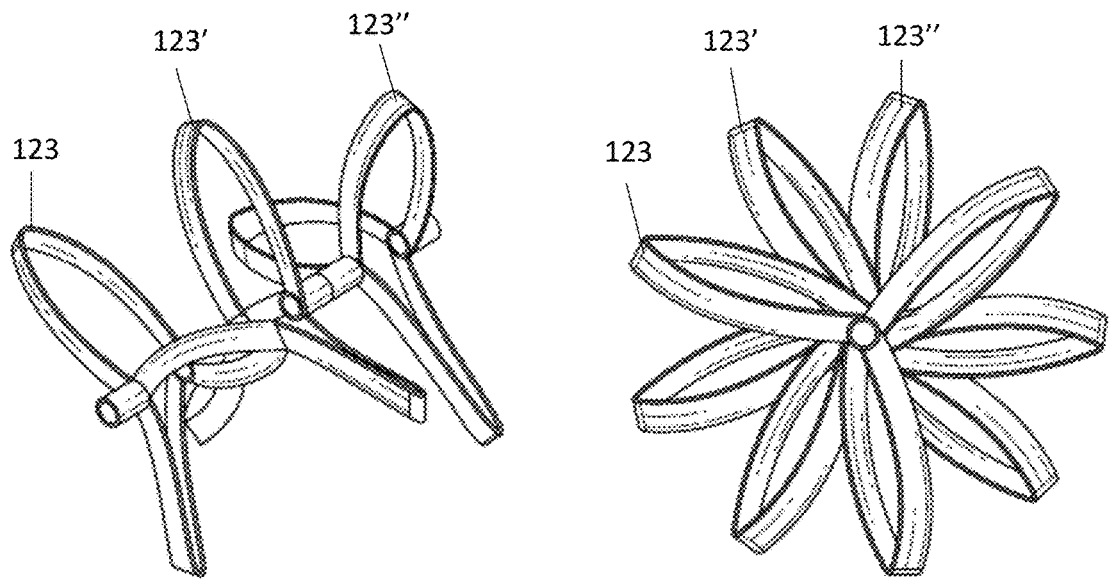
FIGS. 12A-12B illustrate an example of an expandable backstop device as described herein.
Figure 12B:
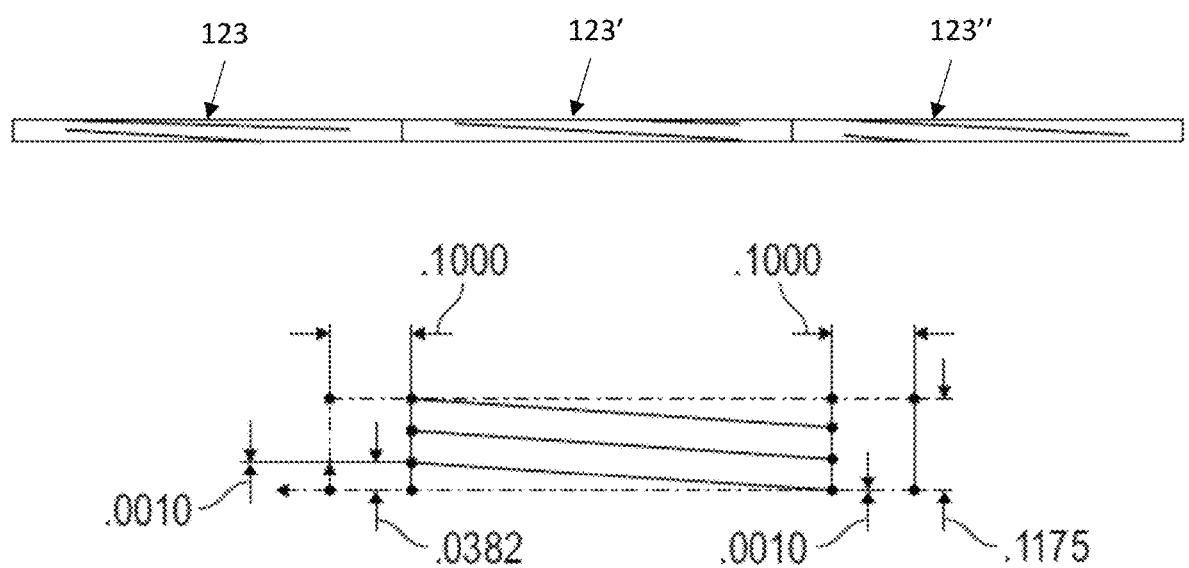

FIGS. 12A-12B show a distal expanding (scraper) region of a similar expandable backstop as in FIGS. 11A-11B, but with wider (e.g., approximately 0.038") helical struts 123, 123', 123", in three total sections (tube OD 0.0374", with 0.00595" wall, ID 0.0255"). FIG. 11 shows the expanded configuration while FIG. 11B shows the collapsed (non-expanded) configuration. The dimensions show in FIGS. 12A-12B an example only, and other dimension may be used (e.g., +/−5%, 10%, 25%, 50%, 70%, 100%, etc. of the dimensions shown). In FIG. 12B, the second section including struts 123' is rotated 40 degrees counter-clockwise in reference to the first section including struts 123, and the third section including struts 123" is rotated 80 degrees counter-clockwise in reference to the first section including struts 123.

Figure 13A:
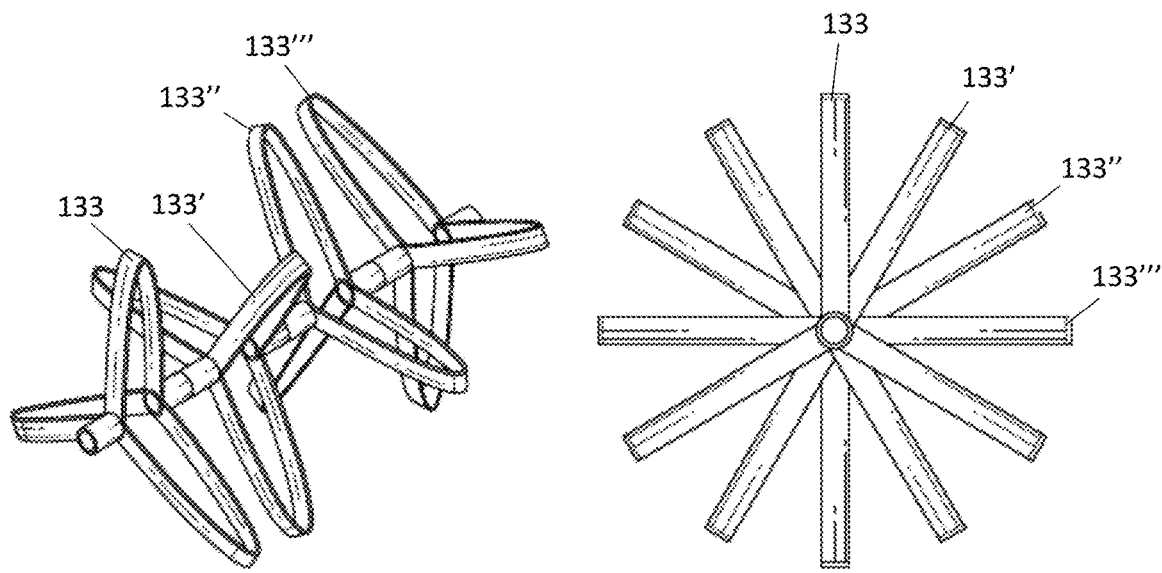
FIGS. 13A-13B illustrate and example of an expandable backstop device as described herein.
Figure 13B:
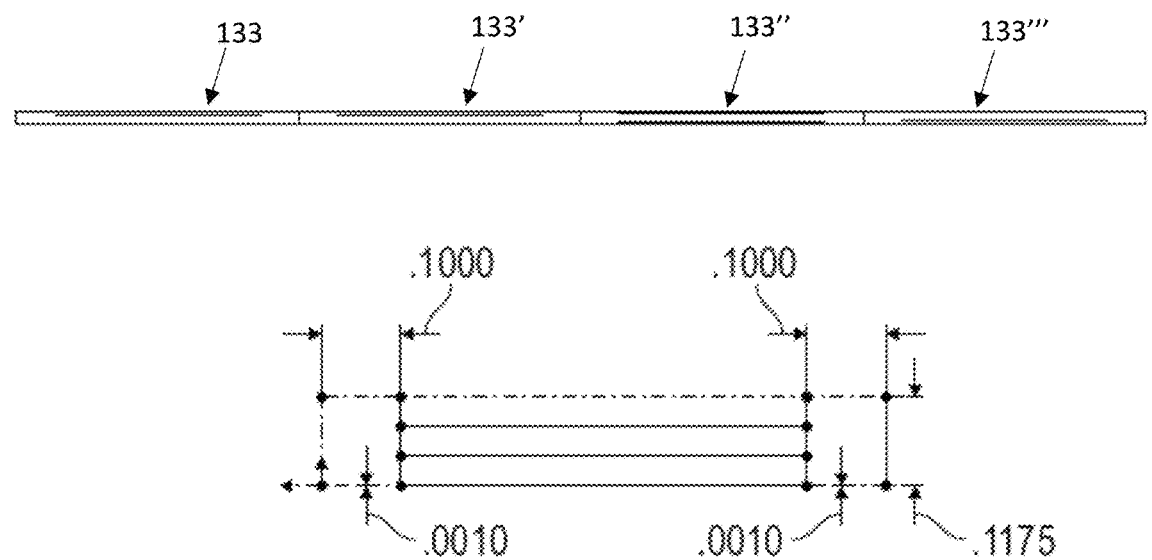

FIGS. 13A-13B show another example of a distal expanding (scraper) region of an expandable backstop having wide helical struts (e.g., legs), (approximately 0.038"), non-offset struts 133, 133', 133", 133''', 4 total sections (tube OD 0.0374", with 0.00595" wall, ID 0.0255"). FIG. 13B shows the device of FIG. 13A in the un-expanded configuration. In any of these examples the distal expanding (scraper) region may be preset into an expanded or a collapsed configuration. The dimensions show in FIGS. 13A-13B an example only, and other dimension may be used (e.g., +/−5%, 10%, 25%, 50%, 70%, 100%, etc. of the dimensions shown). In FIG. 13, the second section including struts 133' is rotated 30 degrees counter-clockwise in reference to the first section including struts 133, and the third section including struts 133" is rotated 60 degrees counter-clockwise in reference to the first section including struts 133, and the fourth section including struts 133''' is rotated 90 degrees in reference to the first section including struts 133.

Figure 18A:
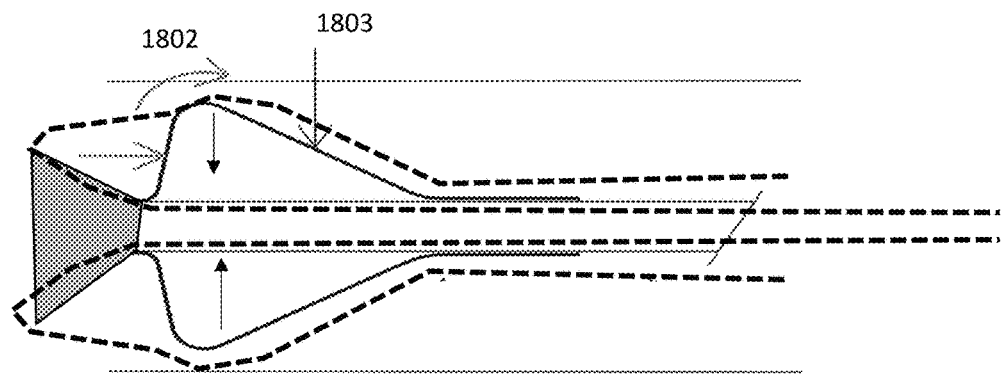
FIGS. 18A-18B illustrate an example of an inverting thrombectomy apparatus including an integrated expandable backstop/scraper.
Figure 18B:
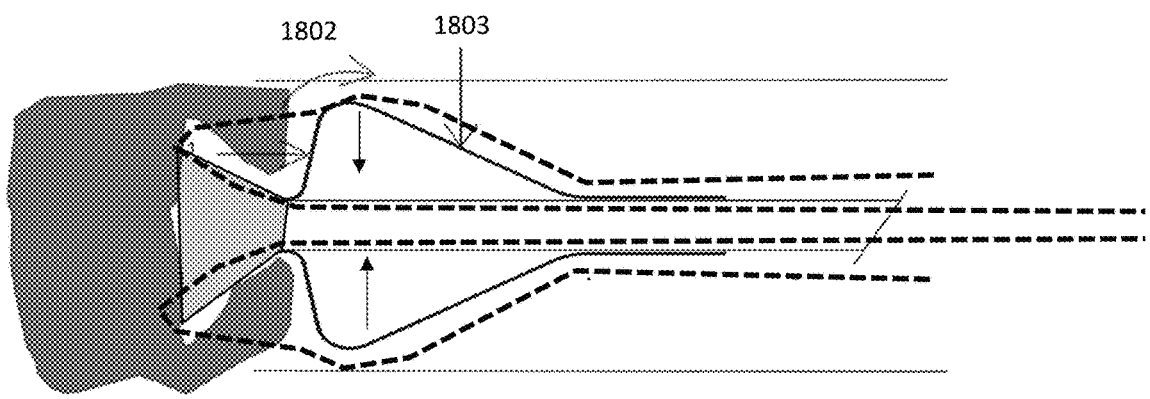

FIGS. 18A-18B illustrate an example of an inverting thrombectomy apparatuses including an integrated expandable backstop/scraper 1803 (shown in this example as integrated into the inversion support catheter proximal to the distal end region). The inverting tube 1802 may slide over the scraper 1803 as the inverting tube is pulled into the device. Features of any of the expandable scraper and/or expandable backstop devices described herein may be recombined with each other and/or combined with one or more of the inverting thrombectomy apparatuses described herein.

For example, in FIG. 18A the inversion support catheter of the inverting thrombectomy apparatuses includes an expandable scraper/backstop region that may be integrated with the device and may assist in removing clot material from on or around the walls of the vessel lumen, as shown in FIG. 18B. The flexible tube may be pulled over the distal end and into the device, as shown. In the example of FIGS. 18A and 18B both the distal funnel region and the more proximal distal expanding (scraper) region may be collapsed in the delivery configuration and may be expanded once the device is positions near the clot. The device may be advanced distally while drawing the puller proximally and therefor pulling the flexible tube over the end of the inversion support catheter and into the lumen of the inversion support catheter. In this example, the funnel and the more proximal expanding scraper/backstop region may be controllable expanded when deploying or collapsed when removing the apparatus from the vessel.

In general, the expandable scraper devices described herein may be configured as braided expandable scraper devices that are configured to remove clot material from within a vessel without damaging the walls of the vessel, including the intima, and/or the intima and media. In general, the expandable portion may be an expandable basket that is formed of a plurality of braided wires or fibers. The material and arrangement forming the basket may be specifically configured to optimize scarping and removal of clot material, while preventing jamming of the device within the vessel and also while preventing damage to the vessel wall during operation.

For example, the braided baskets forming the expandable region may form pores (spaces between the braided wires or fibers). The pore size of the basket as well as the pulling stiffness of the basket may be within functional ranges that allow it to be operated without jamming and without damaging the vessel wall; outside of these ranges the expandable scraper device may otherwise jam and/or may damage the vessel.

FIGS. 19A-19D illustrate one example of an expandable scraper device 1900. In this case, the device includes an elongate shaft 1903 that extend from the distal end to the proximal end of the device. The elongate shaft includes an inner elongate member 1927 (visible in FIG. 19D) that is slidably disposed within an outer elongate member 1925. The overall elongate shaft is flexible, so that it can navigate through tortious vessels within the body. The overall length of the device may be, e.g., between 30 cm and 200 cm (e.g., between 50 cm and 180, between 100 cm and 150 cm, etc.). For example, the length of the device shown in FIG. 19A is approximately 134 cm±5 cm and has an effective length of about 115 cm±5 cm. The length of the elongate shaft may be, e.g., between 20 cm and 180 cm (or longer), such as between 40 cm and 180 cm, between 50 cm and 150 cm, etc. In some cases, the shaft may have an inner diameter that is, e.g., between 0.5 mm (+/−0.025 mm) to 1.5 mm (+/−0.025 mm), such as about 1.0 mm. The outer diameter may be, e.g., between about 2.2 mm and about 3.0 mm (e.g., between about 2.5 mm and about 2.85 mm), +/−0.025 mm.

The elongate shaft may be formed of any appropriate material, including in particular, a polymeric material such as styrenic block copolymers (e.g., Kraton®), functionalized thermoplastic olefins, thermoplastic elastomeric alloys, thermoplastic polyurethanes (e.g., Estane®, Pellethane®), polyamide-based thermoplastic elastomers (e.g., Pebax®), polyester-based thermoplastic elastomers (e.g. Hytrel®), ionomeric thermoplastic elastomers (e.g., Surlyn®), and any combinations thereof.

The expandable braided basket device in FIG. 19A also includes an expandable braided basket 1907 at a proximal end of the device. In this example, the expandable braided basket ("basket") is coupled at a first end to a distal end region of the outer elongate member, and at a second (e.g., distal) end to a distal end region of the inner elongate member. This is illustrated in more detail in FIG. 19D, showing the basket in a collapsed (non-expended) configuration. In general the expandable braided basket may be formed of wires or filaments. It is beneficial to use wires or filaments having a diameter of about 0.15 mm or more (e.g., 0.18 mm or more, 0.20 mm or more, etc.). This size wire/filament may provide a basket having a surface texture that, when braided as described herein, may remove plaque material without damage to the vessel walls. In any of these devices the basket may also include a marker, e.g., a radioopaque (RO) marker 1931, shown at the distal end region of the basket.

The expandable braided basket device may also include a handle 1909, which is shown in more detail in FIG. 19B. The handle is coupled to the elongate member at the proximal end, and may include one or more controls 1911, 1913 for operating the expandable basket, e.g., expanding/contracting the expandable basket, and/or locking the expandable basket in a particular expansion position. The controls shown in FIG. 19B include a slider 1311 that may extend or retract the inner elongate member 1927 relative to the outer elongate member to expand or contract the basket. The control is configured to slide the inner elongate member relative to the outer elongate member to expand the expandable braided basket from an unexpanded configuration. The handle also includes a lock control 1913, shown as a button that releases a ratcheting lock to allow the slider to move or, when released, locks the slider (and thus the expansion of the basket) in place. In FIG. 19B the handle includes a grip region 1915 that is configured to be held by the user, e.g., doctor, nurse, technician, etc.

The device shown in FIGS. 19A-19D also includes a plurality of protrusions 1941, one of which is shown in greater detail in FIG. 19C. In this example the protrusion is an annual ring (or ferrule). Three protrusions 1941, 1941', 1941" are shown. These protrusions are configured to engage with a lock on the handle 1943 that may receive a projection and may releasably lock onto the projection as it is pulled distally, to form a loop of the elongate shaft and to decrease the effective length of the elongate shaft. This is described in greater detail below in reference to FIGS. 27A-27B.

Figure 20A:
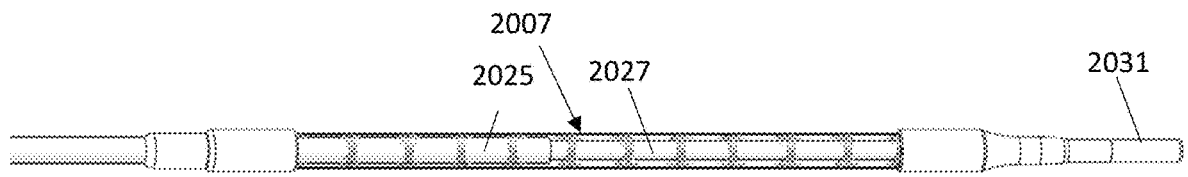
FIGS. 20A-20C illustrate an enlarged view of one example of an expandable basket of an expandable scraper device.
Figure 20B:
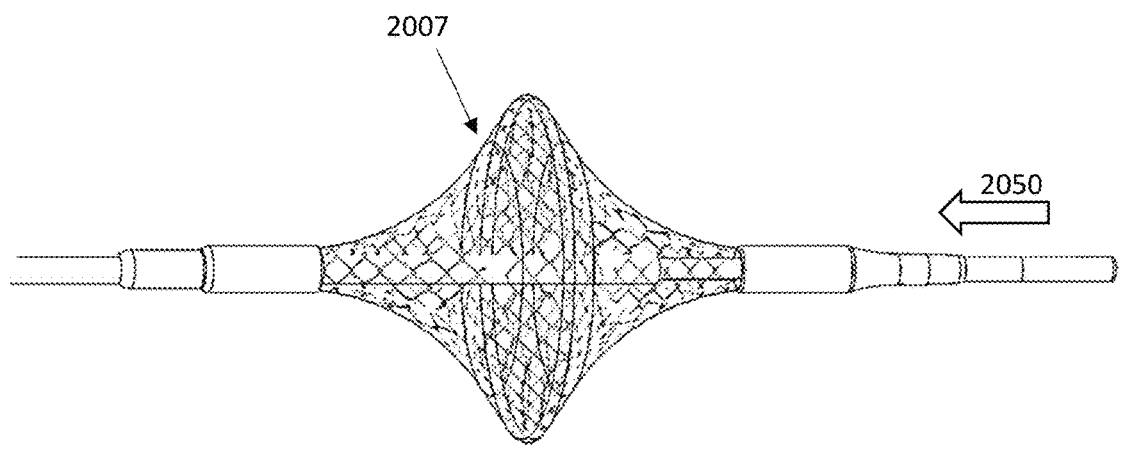

FIGS. 20A and 20B illustrate one example a distal end of a device similar to that shown in FIG. 19A-19D, including the basket 2007, an inner elongate member 2027 and an outer elongate member 2025. The basket in this example is formed of a plurality of wires that are braided loosely together. FIG. 20A shows the basket in the collapsed, fully un-expanded configuration. FIG. 20B shows the basket 2007 in a fully deployed, expanded configuration. In this example, the braided wires are Nitinol wires that are configured to expand outwards to a maximum expansion diameter of, e.g., between 10 mm and 40 mm (e.g., 20 mm, 30 mm, etc.). The basket region may have an unexpanded length of between 3 and 14 cm, such as, e.g., 5 cm (+/−0.2 cm), 7 cm (+/−0.2 cm), etc.

As shown in FIG. 20B, the basket may be expanded by pulling the distal end of the basket (wires) proximally 2050, relative to the proximal end of the basket, so that the basket expands outwards. Alternatively in some examples the basket may be expanded outwards by driving the proximal end distally. The basket may be expanded partially or fully. In some examples the basket may be locked in one or more (or any/continuous) intermediate positions.

Figure 20C:
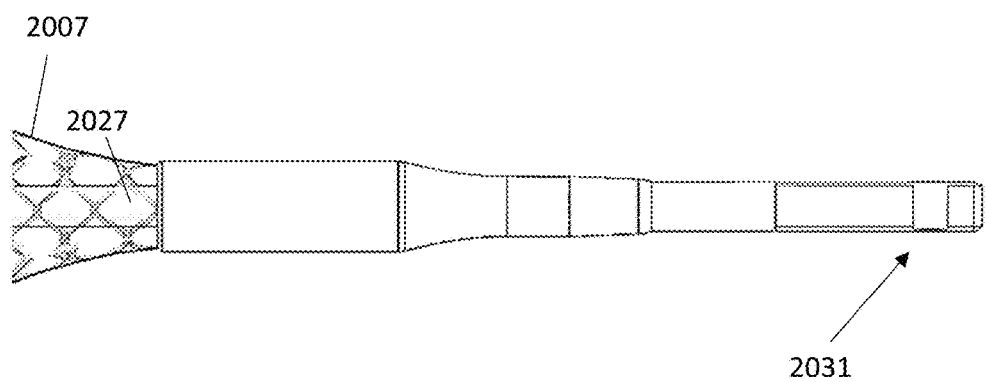

In FIG. 20C, the distal end region of the device is shown, showing the attachment of the distal end of the basket to the inner elongate member. In FIG. 20C, the distal end of the device also includes a RO maker 2031. In an of these expandable scraper devices, the device may include a lumen through which a guidewire or other elongate member may pass, such as a lumen through the inner elongate member 2027.

Figure 21A:
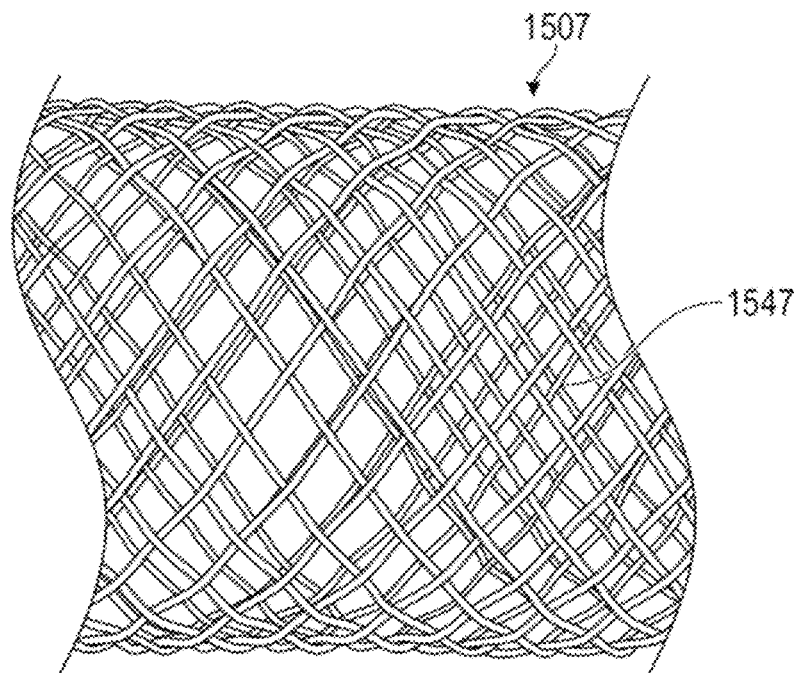
FIGS. 21A and 21B illustrate examples of basket regions of an expandable scraper device.
Figure 21B:
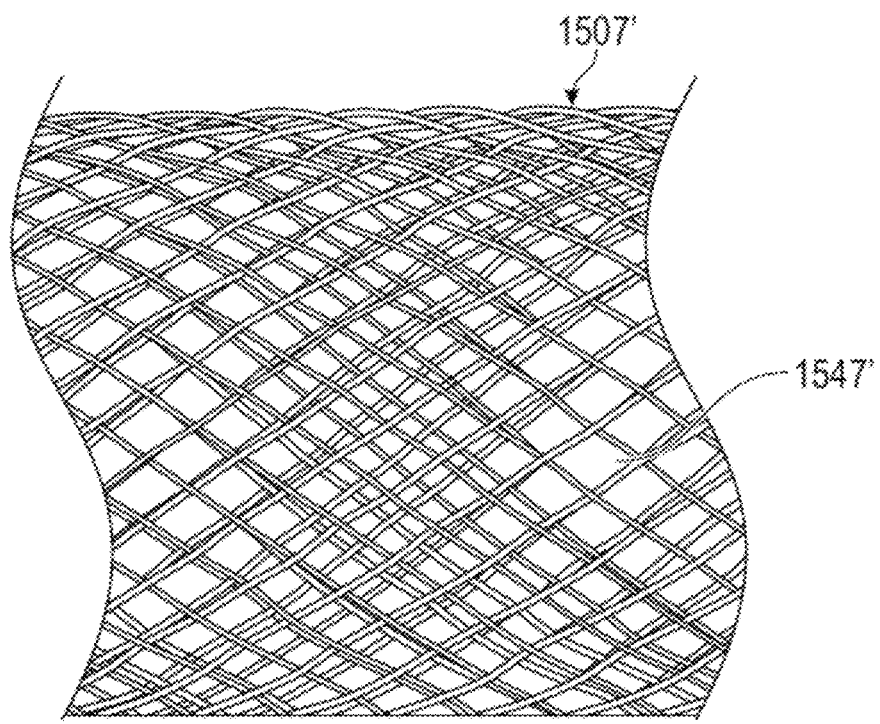

In this example the basket may be formed of a plurality of wires of a superelastic alloy (e.g., a nickel titanium alloy, such as Nitinol), which is superelastic and may be repeatedly bent without breaking. Other materials (stainless steel, polymers, etc.) may be used in some examples. The basket may be braided into a pattern. For example FIGS. 21A-21B illustrate examples of braided baskets shown in an expended configuration. In FIG. 21A, the basket 1507 is braided into a pattern of diamond-shaped pores 1547 each having a pore area. The pore area may change as the device is expanded or contracted but is consistent for a particular expansion diameter. For example, in FIG. 21A, the pore size is between 1.2 and 7.5 mm$^2$ (e.g., may have a pore size of between 1.2 and 5 mm$^2$) when the expandable braided basket is expanded to between 5 and 15 mm in diameter; in this example, the basket has a maximum diameter in the expanded configuration of 20 mm.

In FIG. 21A, the basket is formed of a braided Nitinol material (from 0.2 mm diameter wire). This example includes 32 wires (32 ends) and forms a pattern that is referred to as a half load diamond pattern (1 over 1 under 1). The basket has a 40 pitch per inch. FIG. 21B shows a similar basket, also formed of a braided Nitinol material (0.2 mm diameter wire). In this example, the basket is formed of 48 end (48 wires) and is braided into a full load regular pattern (1 over 2 under 2), with a 50 pitch per inch. The basket 1507' shown in FIG. 21B has a maximum open diameter of 30 mm. The pore size 1547' is also between 1.2 and 7.5 mm$^2$ when the expandable braided basket is expanded to between 5 and 15 mm in diameter.

The applicants have found that, for a given diameter of wire or filament greater than 0.15 mm diameter (e.g., 0.2 mm or greater, between 0.15 and 0.5 mm, between 0.15 and 0.4 mm, between 0.15 and 0.3 mm, etc.) forming the baskets described herein (e.g., having a maximum outer diameter of between 15 and 40 mm), there is an optimal pore area that provides a surface texture that is sufficient to scrape clot without damaging the intima of the vessel, while also preventing jamming within the vessel. Specifically, when the wires or filaments forming the basket have a diameter of 0.15 mm or more and are braided into a pattern having a pore area of between 1.2 and 7.5 mm$^2$ (or 1.2 and 5 mm$^2$) when the expandable braided basket is expanded to between 5 and 15 mm in diameter (and have a maximum diameter in an expanded configuration of between 15 and 40 mm), the resulting basket is sufficiently rough textured to remove clot material from the vessel wall, while preventing jamming within the vessel. In some examples the basked may be configured to expand in an off-axis manner, as will be described in greater detail below. The configuring the basket so that it assumes an off-axis shape when expanded has surprisingly been found to provide scraping without damaging the vessel wall; without being bound by theory, this may be due at least in part, to the ability of the wires or filaments forming the basket to move relative to each other and to allow the basket to collapse. The off-axis shape has been found to limit the pull force, when the basket it expended in an off-axis shape, to a maximum scraping force of about 1.5 pounds of force against the wall of the vessel lumen.

In operation the apparatuses described herein may be configured to have a pull force of between 0.18 and 1.5 pounds of force within a vessel when expanded against the vessel wall with a radial force of, e.g., between about 0.25 and 0.6 pounds. Outside of these ranges for the pore size and for the applied pull forces, the baskets may jam or may damage the vessel. Table 1 illustrates examples of baskets having a verity of ranges of pore sizes that do not jam within the vessel.

TABLE 1

| Maximum open diameter | Pore size Area | Scrape/Jam? |
|---|---|---|
| 20 mm basket | 2.7 mm × 0.5 mm (1.35 mm$^2$) at 5 mm expansion | NO |
| 20 mm basket | 3.1 mm × 1.0 mm (3.1 mm$^2$) at 10 mm expansion | NO |
| 20 mm basket | 2.5 mm × 2.6 mm (6.5 mm$^2$) at 15 mm expansion | NO |

TABLE 1-continued

| Maximum open diameter | Pore size Area | Scrape/Jam? |
|---|---|---|
| 30 mm basket | 2.9 mm × 0.4 mm (1.16 mm$^2$) at 5 mm expansion | NO |
| 30 mm basket | 3.3 mm × 1.1 mm (3.63 mm$^2$) at 5 mm expansion | NO |
| 30 mm basket | 3.1 mm × 1.4 mm (4.34 mm$^2$) at 5 mm expansion | NO |

As mentioned, for larger pore sizes, which would result in bigger holes through the basket, although the texture may be greater, the texture may be overly aggressive and may damage the intima, leading to bleeding, and tearing of the vessel wall. Further, if the pores are too large (e.g., greater than about 8 mm$^2$), the clot material may instead pass into the basket without sufficient scraping. The ranges described above may balance the pore size for preferred scraping texture (using a wire of diameter greater than or equal to about 0.006", e.g., about 0.008") and the ability to pull with a predetermine pull force without damaging the vessel, which may also be described as the stiffness of the basket.

In general, the basket must be sufficiently stiff while in the vessel so that it scrapes the vessel walls when expanded, however it should not be overly stiff, or it may damage the vessel walls. The expandable basked may therefore be configured so that it may be expanded against the vessel walls with a radial expansion force that is sufficient to load the walls of the vessel, and once loaded against the walls of the vessel within a predetermined range of radial force, may apply a force against the vessel walls when being pulled (or pushed) along the vessel that is within a predetermined range. This force, which is applied by pulling (or pushing) the at least partially expanded basked of the expandable scraper device, may be referred to herein as the pull force. The pull force may be a function of the stiffness of the basket. In general, expanded baskets having a pull force of between of between about 0.18 and 0.4 pounds when expanded within the lumen with a radial force (against the lumen wall) of between about 0.25 and 0.6 pounds of force against the wall of the vessel lumen may correspond to a specific range within which the device may remove clot material effectively while avoiding damage to the vessel wall. Outside of this range of pull force (e.g., outside of between about 0.18 and 0.4 lbf, or between about 0.2 and 0.35 lbf, or between about 0.2 and about 0.33 lbf, when the basket is expanded to apply a radial force of between about 0.25 and 0.6 lbf against the wall), the basket may either lock up or may damage the vessel wall, if greater than the upper limit of this range (e.g., greater than 0.4 lbf), while if the pull force is less than the lower limit of this range (e.g., less than 0.18 lbf) the basket will not effectively scrape clot material. Without being bound by theory, it is possible that the configurations in which the basket is expanded off-axis may provide non-uniform radial force within eh vessel lumen, which may, surprisingly, allow more gentle and effective scraping and removal of clot material. Non-uniform force applied by the off-axis baskets described herein may the device to more efficiently track through the vessels.

Examples of various load (expanded) force and pull forces are provided for illustration herein, however, these forces are not intended as limits, but merely examples. For example, a "20 mm basket" (or 20 mm scraper), which may refer to a basket having a maximum expanded diameter of about 20 mm, may be within the effective range when approximately 0.32 lbf of force (radial force) is used to load the vessel wall and approximately 0.26 pounds of force (pull force) is used to slide the basket in a 6 mm vessel or when approximately 0.31 lbf of force (radial force) is used to load the vessel wall and approximately 0.22 lbf (pull force) is used to slide the basket in a 12 mm vessel, or when approximately 0.46 lbf (radial force) is used to load the vessel wall and approximately 0.28 lbf (pull force) is used to slide the basked in a 16 mm vessel. Similarly, a 32 mm basket, which may refer to a basket having a maximum expanded diameter of about 32 mm, is within the effective range when approximately 0.49 lbf (radial force) is used to load the vessel wall and approximately 0.24 lbf (pull force) is used to slide the basked in a 16 mm vessel, or when approximately 0.45 lbf of force (radial force) is used to load a vessel wall and approximately 0.30 lbf (pull force) is used to slide the basked within a 20 mm vessel, or when approximately 0.49 lbf (radial force) is used to load a wall and approximately 0.30 lbf (pull force) is used to slide the basket in a 28 mm vessel. As mentioned above, the radial force may be non-uniformly applied around the diameter of the backet against the wall of the vessel lumen, particularly in off-axis baskets.

Thus, any of the expandable scraper devices described herein may be configured so that the expandable basket assumes a non-radially symmetrical configuration ("off-axis"), so that the central shaft of the expandable basket is off axis. As mentioned, configuring the basket to assume this shape has been found to be surprisingly effective. This may be beneficial because it permits the basket to contact and scrape the walls of the vessel while the elongate shaft (in some examples comprising the inner and outer shafts) may be positioned out of the midline of the vessel with the basket expanded within the vessel. This off-axis configuration may also allow the expandable scraper device to be positioned in the vessel in tandem with another device; for example, an expandable scraper device may be laterally displaced (proximal to the expanded basket), providing room for an adjacent device (e.g., suction) in this proximal region within the vessel while still being able to expand and scrape the vessel walls.

FIGS. 20A-20C illustrate a radially-symmetric example of a scarper. As illustrated above in reference to FIGS. 20A-20C, in some examples the expandable scraper includes a longitudinal shaft (a portion of the elongate shaft) about which the scraper expands outward. Alternatively, the longitudinal shaft within the basket may be configured to deflect during expansion of the basket. Thus, the basket may be configured for off-axis expansion (deforming away from the longitudinal midline) in part because of the flexibility of the longitudinal shaft and also because of the configuration and flexibility of the wires forming the basket. Thus, in general, the expandable basket may be configured to deform in the expanded configuration into an off-axis shape.

Figure 22A:
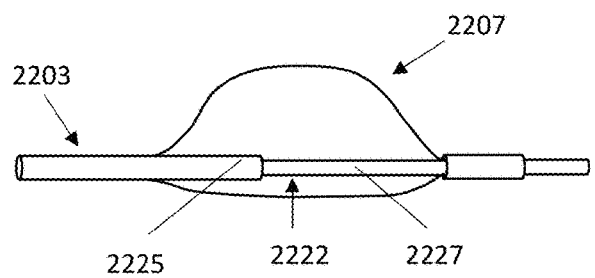
FIG. 22A shows a side view and FIG. 22B shows an end view of one example of a basket of an expandable scraper device, in which the basket is configured to deform to expand off-axis of a longitudinal shaft of the expandable scraper device.
Figure 22B:
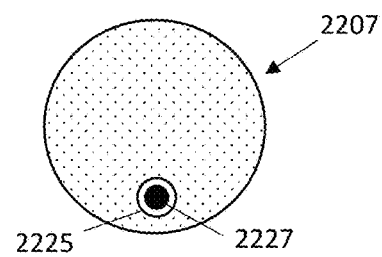

This is illustrated in FIGS. 22A-22B and FIGS. 23A-23F. In FIG. 22A, the basket region 2207 of an expandable scraper device is shown at least partially expanded. The basket 2207 (shown schematically, pores not visible) is expanded and a longitudinal shaft portion 2223 of the elongate shaft 2203, including a flexible inner elongate member 2227 that is slidably disposed within a flexible outer elongate member 2225 is shown. This longitudinal shaft portion 2222 may be flexible (bendable). As shown in FIG. 22B, which illustrates a distal end view of the basket 2207 and elongate shaft 2203, the longitudinal shaft is off-axis (away from the midline of the basket) but may expand to contact, and therefore scrape, the wall of the lumen.

Figure 23A:
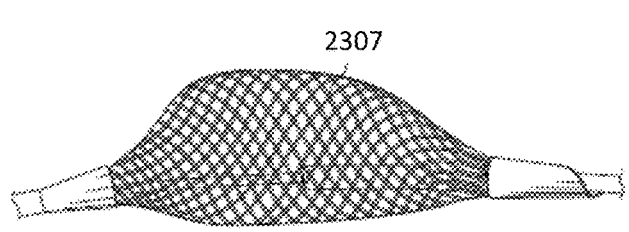
FIGS. 23A-23F illustrate examples of expandable baskets similar to that shown in FIGS. 22A-22B.
Figure 23B:
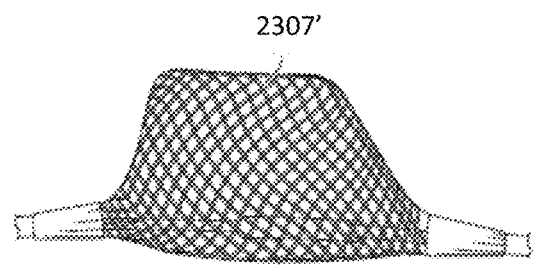
Figure 23C:
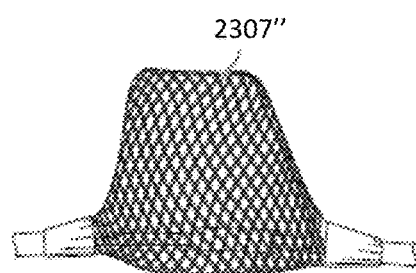
Figure 23D:
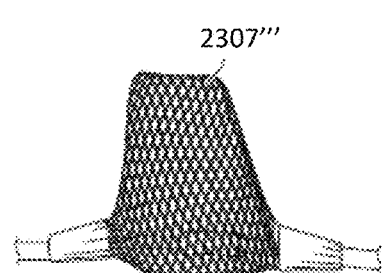

FIGS. 23A-23F illustrate examples of baskets expanded so that the longitudinal shaft is radially offset from the midline of the expanded basket. In FIG. 23A the basket 2307 is at least partially expanded within a lumen of a vessel having a diameter of about 8 mm. In FIG. 23B the basket 2307' is at least partially expanded within a lumen of a vessel having a diameter of about 10 mm. In FIG. 23C, the basket 2307" is at least partially expanded within a lumen of a vessel having a diameter of about 12 mm. in FIG. 23D, the basket 2307''' is at least partially expanded within a lumen of a vessel having a diameter of about 14 mm. In each of these examples the basket is a braided basket that expands as shown. The devices may be driven (pulled or pushed) within the vessel lumen to scrape the walls of the vessel.

Thus, an expandable scraper device may include an elongate shaft and an expandable braided basket coupled to the elongate shaft (with the elongate shaft extending within the basket), wherein the expandable braided basket is configured to deform in an expanded configuration so that a portion of the elongate member within the expandable braided basket is non-concentric with the expandable braided basket, as shown. Any of these expandable scrapers may also include a proximal handle as described above.

Thus, any of the apparatuses (e.g., device, system, etc., including expandable scraper devices) may be configured as off-axis scrapers. These expandable scraper devices may include a central shaft about which the scraper expands in non-radially uniform matter, so that the basket deflects off-axis during expansion. The apparatus may be configured for off-axis expansion by selecting the number, size and/or material properties of the wires (filaments) used, as well as the manner in which the wires/filaments are braided. The flexibility of the central shaft and the flexibility of the wires forming the basket, including their relative flexibility, may result in the off-axis configurations described herein. In some examples the basket may therefore be configured to have variable pore size. The expandable basket may be configured to deform in the expanded configuration into an off-axis shape, as shown in FIGS. 22A-22B and 23A-23F.

Figure 23E:
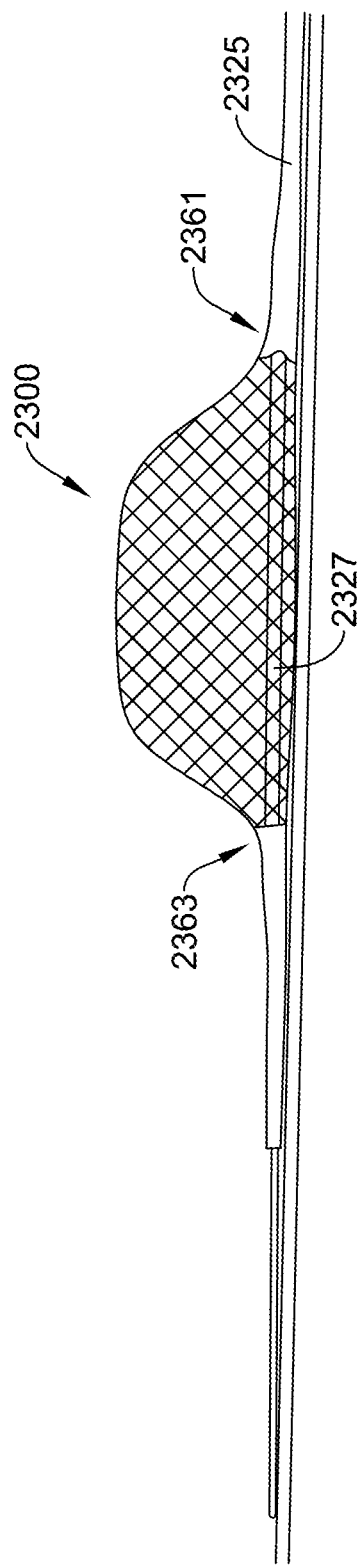
Figure 23F:
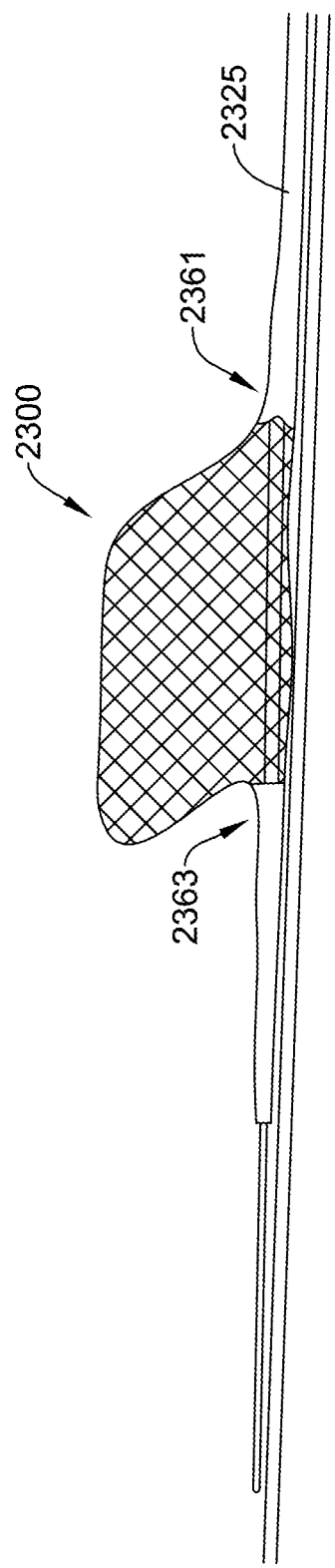

For example, FIGS. 23E and 23F show an example of an expandable scraper device 2300, comprising: an elongate shaft comprising a flexible inner elongate member 2327 slidably disposed within a flexible outer elongate member 2325. The inner elongate member may be a shaft, cannula (e.g., including a lumen such as a guidewire lumen), a rod, a wire, or the like. The outer elongate member may be a cannula and may include a lubricious inner layer. The device also includes an expandable braided basket 2300 coupled at a proximal end 2361 to a distal end region of the flexible outer elongate member and at a distal end 2363 to a distal end region of the flexible inner elongate member, wherein the expandable braided basket 2300 is configured to deform from an unexpanded configuration of wires into an expanded configuration so that a portion of the flexible inner elongate member within the expandable braided basket is non-concentric with the expandable braided basket, as shown.

In FIGS. 23E and 23F the inner elongate member 2327 is radially offset from the midline of the basket and is shown displaced on one side of the basket. The basket expands outwards within the vessel lumen (in this example, the vessel lumen is modeled as a clear polymeric tube.

The apparatus may also include a proximal handle (not shown in FIGS. 23A-23F) but described and shown in greater detail below in reference to FIGS. 24A-27C. As will be described in greater detail below, the handle may include a control configured to slide the flexible inner elongate member relative to the flexible outer elongate member to expand the expandable braided basket. The control on the proximal handle may be a slider coupled to the flexible inner elongate member.

In general, the expandable braided basket may be configured to be opened into an off-axis configuration as described above and shown in FIGS. 23A-23F. In some examples the apparatus may be formed of a superelastic alloy material (e.g., a nickel titanium alloy material). The basket may be formed of between about 10-60 filaments (e.g., between 20-60, etc.), and may be shape set so that the basket is collapsed (un-expanded). Thus, when the basket region is unconstrained, it may collapse into the un-expanded configuration. For example, the superelastic alloy may be shape-set to return to the unexpanded configuration. Any appropriate wires may be used, but in particular, the basket may be formed of wires having a diameter of between about 0.15 mm and 0.35 mm.

The length of the elongate shaft of the device may be, e.g., between 50 and 180 cm. The expandable braided basket may have a length of between about 3 and 10 cm in the unexpanded configuration. The expandable braided basket may be loosely braided, so that the expandable braided basket is configured to deform about a long axis. The expandable braided basket may have a diameter of less than 3.3 mm in the unexpanded configuration. For example, described herein are expandable scraper devices including: an elongate shaft comprising a flexible inner elongate member slidably disposed within a flexible outer elongate member; an expandable braided basket coupled at a proximal end to a distal end region of the flexible outer elongate member and at a distal end to a distal end region of the flexible inner elongate member having a length of between 3 and 10 cm in an unexpanded configuration, wherein the expandable braided basket is formed of between 20 and 60 nickel titanium wires each having a diameter of between 0.15 mm and 0.35 mm, and is configured to deform from the unexpanded configuration into an expanded configuration so that a portion of the flexible inner elongate member within the expandable braided basket is non-concentric with the expandable braided basket, further wherein the expandable braided basket is shape set to return to the unexpanded configuration in an unconstrained state; and a proximal handle comprising a control configured to slide the flexile inner elongate member relative to the outer flexible elongate member to expand the expandable braided basket.

In use, the expandable scraper device may be used to remove clot. For example, the expandable scraper may be positioned within a lumen of a vessel so that an expandable braided basket of the expandable scraper device is positioned distal to or within the clot. The expandable braided basket may then be expended against the wall of the vessel lumen so that an inner elongate member slidably disposed within a flexible outer elongate member within the expandable braided basket is positioned within the expandable braided basket offset from a midline of the expandable braided basket (as shown above). The expandable braided basket may then be pulled proximally to scrape clot material from the wall of the vessel lumen without damaging the wall of the vessel lumen.

For example, also described herein are method of removing clot using any of these apparatuses, such as the off-axis baskets described above. Such a method may include: positioning an expandable scraper device within a lumen of a vessel so that an expandable braided basket of the expandable scraper device is positioned distal to or within the clot; expanding the expandable braided basket against a wall of the vessel lumen by adjusting a control on a proximal handle of the expandable scraper device, so that an inner elongate member that is slidably disposed within a flexible outer elongate member and within the expandable braided basket is positioned within the expandable braided basket offset from a midline of the expandable braided basket; and pulling the expandable braided basket proximally to scrape clot material from the wall of the vessel lumen without damaging the wall of the vessel lumen.

Pulling may comprise pulling with a pull force of between about 0.2 and 1.5 pounds. Any of these methods may include applying suction to remove a clot material from the vessel lumen. Any of these apparatuses may be used with a mechanical thrombectomy apparatus. For example, any of these methods may include using an inverting thrombectomy apparatus.

Positioning the expandable scraper device within the lumen of the vessel may comprises inserting the expandable scraper device adjacent to an inverting thrombectomy apparatus. The scraper may be used as described here, including pulling it proximally so that clot material is dragged and/or removed from the lumen.

Figure 24D:
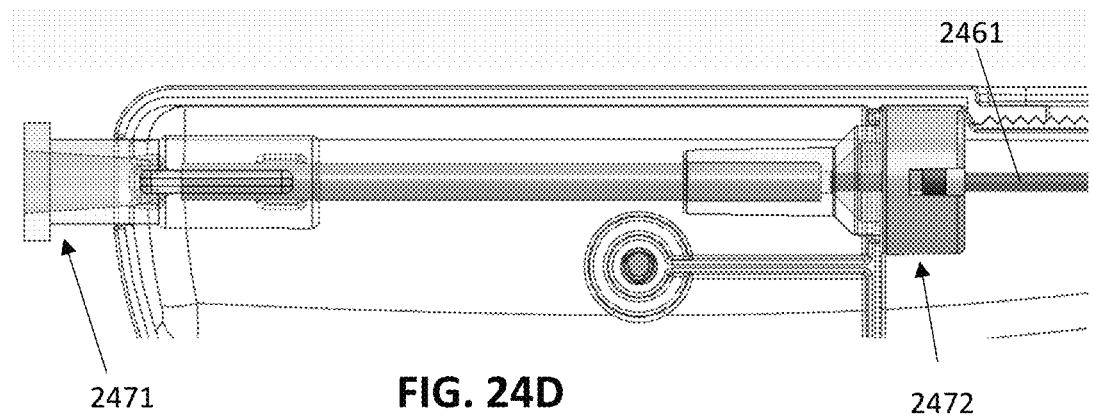

FIGS. 24A-24E illustrate one example of handle 2409 as described above. These handles may be used with any of the devices described herein. In general, the handle 2409 may be configured to be gripped and held in one hand. As mentioned above, the handle may include one or more controls 2411, 2413 for controlling expanding/collapsing the basket as mentioned above. In FIG. 24A the handle includes slider control 2411 that may be slid distally to proximally to expand the basket. For example, as shown in FIG. 24B, the slider may be coupled to the inner elongate member 2461 that is slidably disposed within an outer elongate member 2463. Thus driving the slider proximally (see arrow 2466) may shorten the basket and expand it. The inner elongate member may include a passage (lumen), which may pass a guidewire and/or may be used for passing a fluid (e.g., for flushing). For example, in FIG. 24D, the flush luer 2471 (or port) is shown in a transparent view, couped to the inner elongate member through a flush hub and seal 2472. Thus, the port 2471 may provide access into the lumen. In some examples the apparatus may also include a locking feature for locking the expansion state of the basket.

Figure 24E:
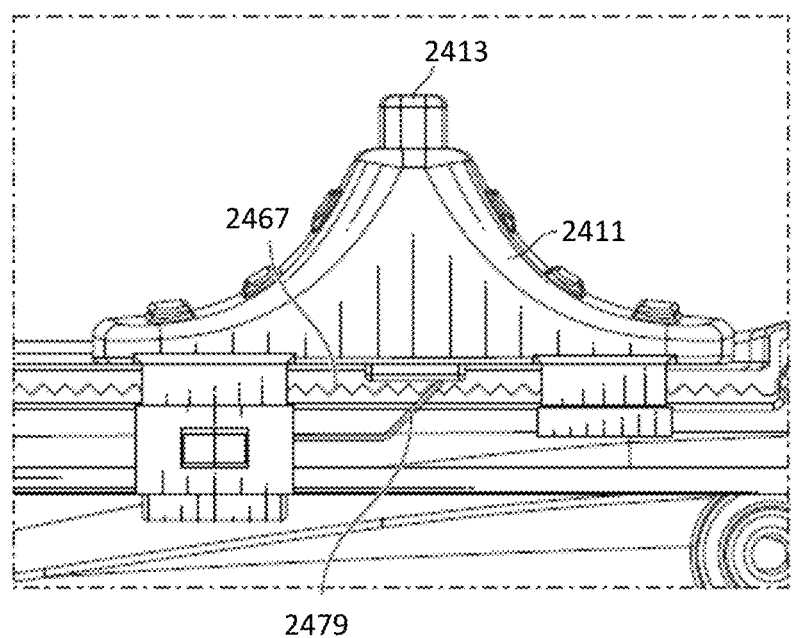

In FIGS. 24B and 24C, a ratcheting lock is shown. In this example the locking feature is configured as a ratcheting lock that includes a toothed surface 2467 into which the locking control 2413 engages to secure the elongate inner member position, preventing it from being moved proximally or distally to further expand or contract the basket. This is illustrated in FIG. 24E, showing the lock control that drives displacement of a pawl or spring element 2479 that engages with the teeth of the toothed surface 2467. Thus, pushing down on the lock control 2413 disengages the pawl element 2479 from the teeth 2467, allowing the slider 2411 to be driven proximally or distally, opening or closing the basket. Once a desired position is achieved, which may be based on the sensed force acting on the basket, as described in more detail below, the lock control may be released, allowing the pawl to engage the teeth and lock the basket position.

Figure 25A:
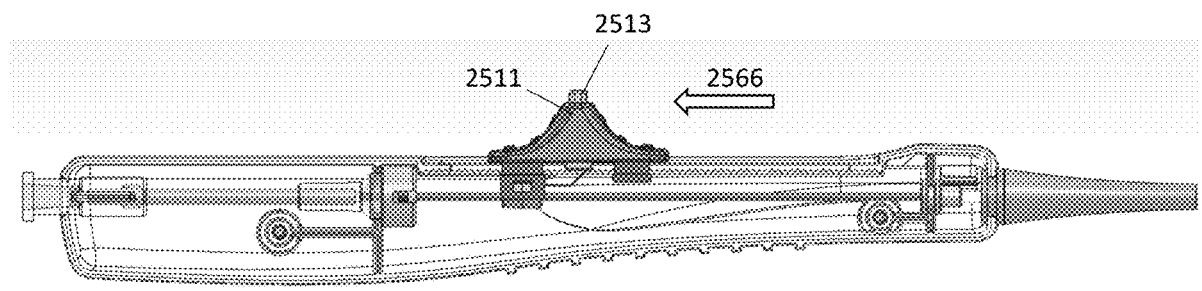
FIGS. 25A-25C illustrate one example of expansion of the basket of an expandable scraper device as described herein.
Figure 25B:
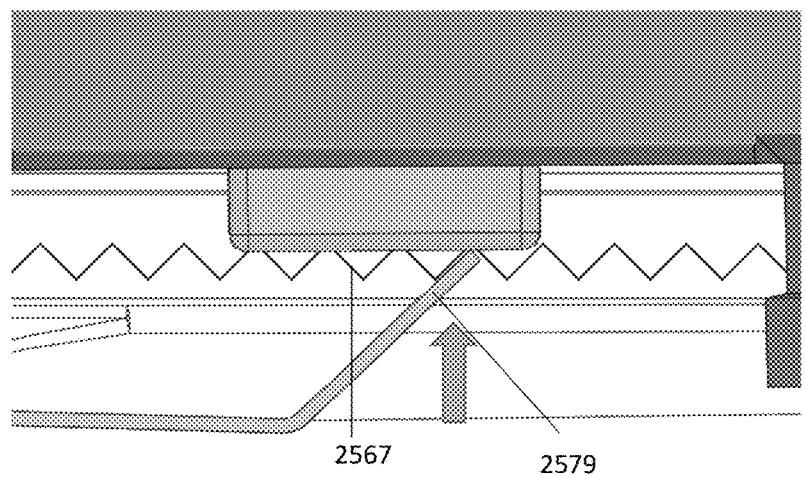
Figure 25C:
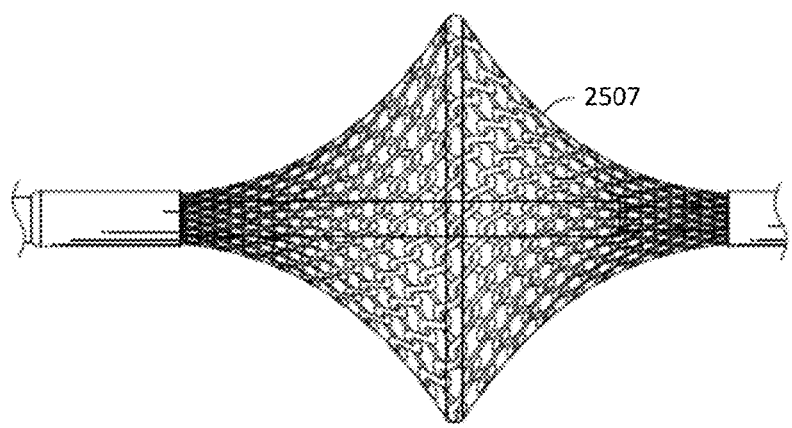
Figure 26A:
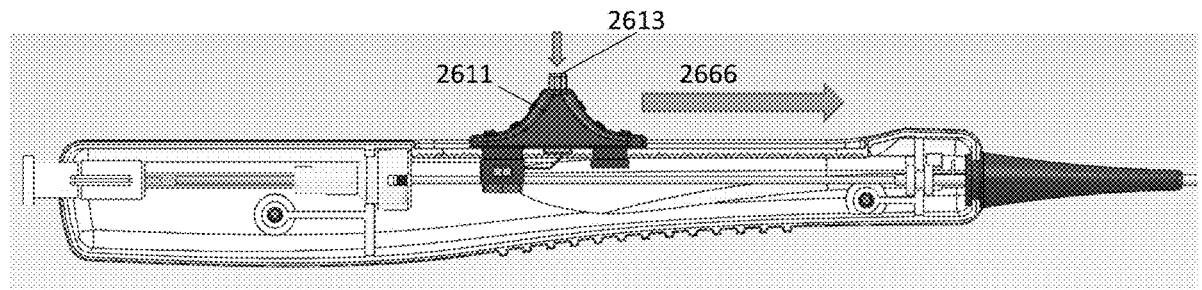
FIGS. 26A-26C illustrate one example of collapse of the basket of an expandable scraper device as described herein.
Figure 26B:
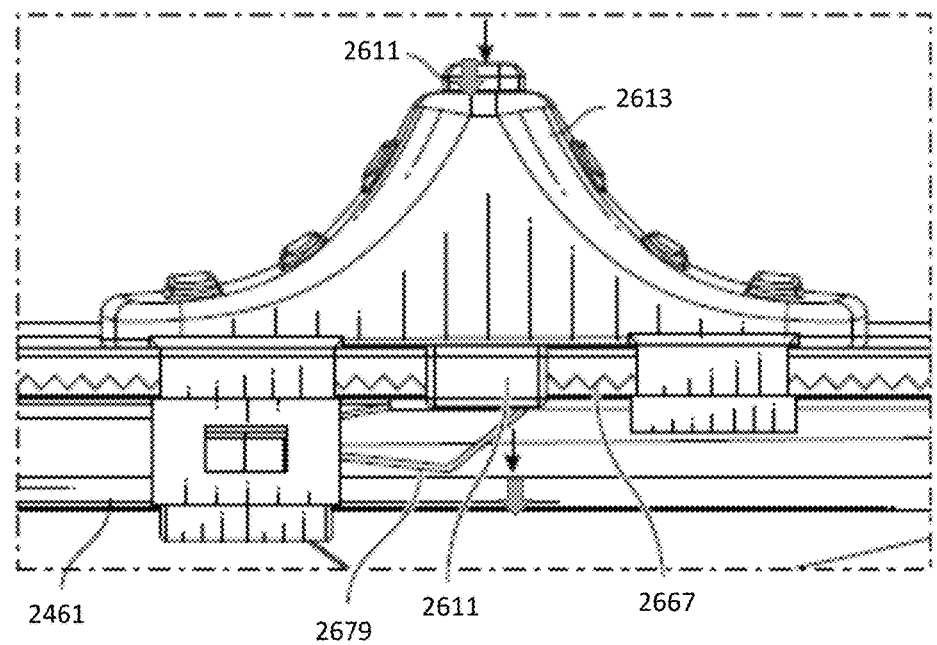
Figure 26C:
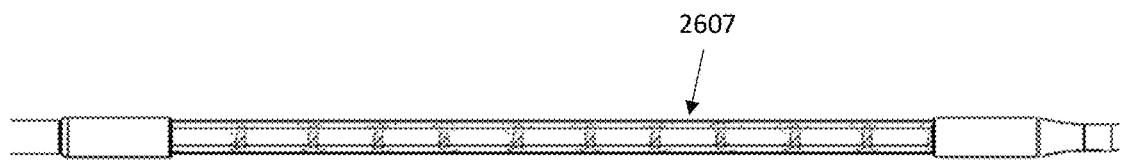

This operation is illustrated in FIGS. 25A-25C and 26A-26C. For example, in FIGS. 25A-25C the basket may be expanded by driving the slider proximally 2566 after releasing the lock by depressing the lock control 2513 to release the pawl 2579 from the teeth 2567 (shown engaged and locking in FIG. 25B). Once the pawl (leaf spring 2579) is disengaged, the slider may be driven proximally, opening/expanding the basket 2507, as shown in FIG. 25C. In FIGS. 26A-26C, the basket may be closed/retracted by again depressing the lock control 2613 to release the pawl (leaf spring) 2679 from the teeth 2667 as shown in FIG. 26B. Thus slider 2611 may then be slid distally 2666 to drive the inner elongate member distally and collapse the basket 2607, as shown in FIG. 26C.

Any of these expandable scraper devices may also include a may also include a lock or gathering feature ("gather") on the handle that may engage with the elongate shaft, and in particular with one or more projections on the shaft to shorten the shaft so that the device may be more easily manipulated by one or two hands, even where the elongate flexible shaft is very long. The projections may releasably engage with the gather (also referred to herein as a lock or stay) on the handle to that the effective length of the elongate shaft is shortened. This is illustrated in FIGS. 27A-27C.

Figure 27A:
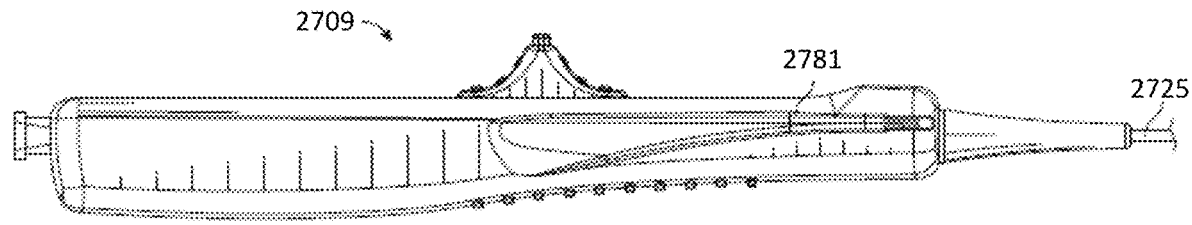
FIGS. 27A-27C illustrate the shortening of the elongate shaft of an expandable scraper device using one or more protrusion on the shaft, in conjunction with an engagement region on the handle of the expandable scraper device.
Figure 27B:
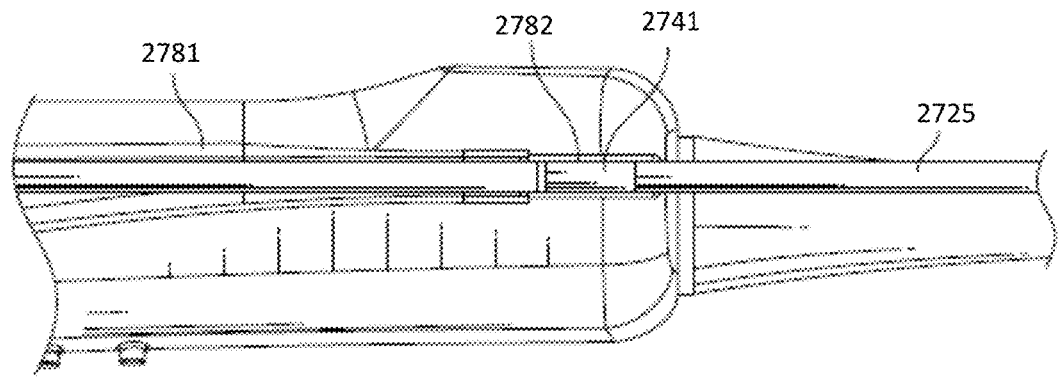
Figure 27C:
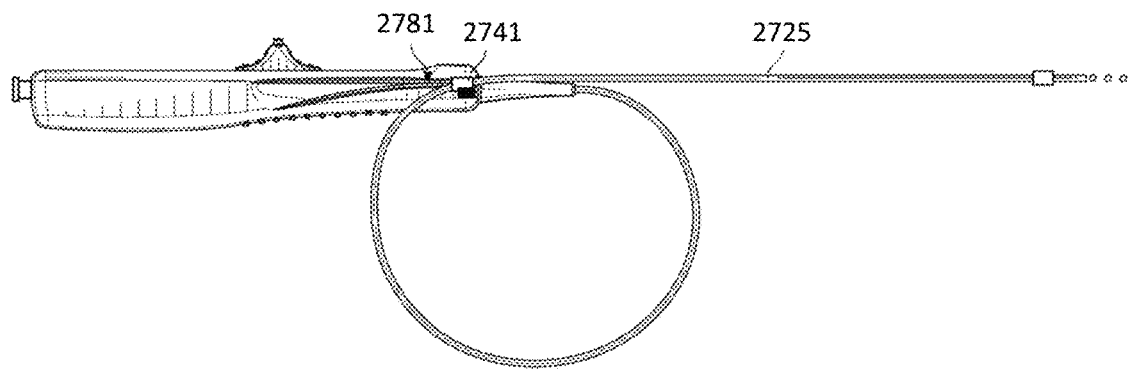

FIGS. 27A-27C illustrate an expandable scraper device including a handle 2709 with one or more projections 2741 (e.g., a locking ring or ferrule) on the elongate flexible shaft to adjust the pull length of the elongate body; the projection 2741 releasably locks onto an engagement region 2781 of the proximal handle of the scarper. The engagement region 2781 includes a tapering channel formed in the side (e.g., in the housing) of the handle and is configured so that the elongate shaft 2725 may be inserted into the engagement region channel and pulled distally until the projection engages with the clamping region 2782 of the engagement region channel, as shown in FIGS. 27B and 27C. In practice a loop of the long and flexible elongate shaft of the device may be formed by sliding the elongate shaft into the engagement region until a projection engages the clamping region of the engagement region; thereafter the handle, and therefore the elongate flexible shaft, may be pulled proximally, e.g., to pull clot material proximally. In some examples the elongate shaft may include more than one (e.g., two, three, four, five, six, etc.) projections that may each engage with the handle at predetermine positions. In some examples the projection may be movably positioned on the shaft, allowing a variable-sized loop to be formed. For example, the projection may be an elastic material that may be rolled or slid along the outer surface of the shaft.

Thus, an expandable scraper device may include an elongate shaft and one or more projections on the elongate shaft, wherein at least one of the oner or more projections is positioned in a middle region of the elongate shaft. The device may also include an expandable braided basket and a proximal handle comprising a control configured to slide the inner elongate member relative to the outer elongate member to expand the expandable braided basket from an unexpanded configuration, and a lock on the proximal handle configured to receive one of the one or more projections from a proximal direction and to releasably lock onto the projection as it is pulled distally, to form a loop of the elongate shaft and to decrease the effective length of the elongate shaft.

Any of the apparatuses described herein may include a handle and wire management features as described herein. For example, any of these apparatuses may include one or more projections on the elongate shaft, wherein at least one of the one or more projections is positioned in a middle region of the elongate shaft. Any of these apparatuses may include a lock on the proximal handle configured to receive one of the one or more projections from a proximal direction and to releasably lock onto the one of the one or more projections as it is pulled distally, to form a loop of the elongate shaft and to decrease an effective length of the elongate shaft. For example, the lock may include a tapered channel on an outer surface of the proximal handle. The one or more projections may include a plurality of projections spaced apart from each other by more than 10 cm.

In general, also described herein are method of manually adjusting the diameter of the basket as it is pulled to maintain force within a range. Device configured to allow this by having button (release) on the handle.

Also described herein are methods of removing clot using the devices described herein. For example, clot may be removed by positioning an expandable scraper device within a lumen of a vessel in an unexpanded configuration so that an expandable braided basket of the expandable scraper device is positioned distal to or within the clot; expanding the expandable braided basket to an expanded configuration against a wall of the vessel lumen where the expandable braided basket is configured to apply a maximum scraping force against the wall of the vessel lumen of 1.5 pounds of force or less; and pulling the expandable braided basket proximally while adjusting a pull force by operating a control on a handle of the expandable scraper device to expand or contract the expandable braided basket to maintain the pull force between about 0.2 and 1.5 pounds of force to scrape clot material from the wall of the vessel lumen without damaging the wall of the vessel lumen.

In any of these methods, the expanding the expandable braided basket comprises expanding the expandable braided basket against a bias force configured to return to the expandable braided basket to the unexpanded configuration in an unconstrained state. Expanding the expandable braided basket may comprise expanding the expandable braided basket from a length of between 3 and 10 cm in the unexpanded configuration. In some examples, expanding the expandable braided basket comprises expanding a braid of between 20 and 60 nickel titanium wires each having a diameter of between 0.15 mm and 0.35 mm into the expanded configuration. For example, expanding the expandable braided basket may include expanding it so that an inner elongate member which extends between a distal end of the expandable braided basket and a proximal end of the expandable braided basket is positioned within the expandable braided basket offset from a midline of the expandable braided basket.

In some examples, adjusting the pull force by operating the control on the handle of the expandable scraper device comprises operating a finger slider to manually adjust expansion of the expandable braided basket to maintain the pull force between about 0.2 and 1.5 pounds of force.

Adjusting the pull force by operating the control on the handle of the expandable scraper device may include operating both a release button and a finger slider to manually adjust expansion of the expandable braided basket to maintain the pull force between about 0.2 and 1.5 pounds of force, as described above in FIGS. 26A-26C.

Any of these methods may include repeatedly positioning the expandable scraper device within the lumen of the vessel to scrape a same location of the vessel by advancing the expandable scraper over a guidewire in the collapsed configuration, expanding the expandable scraper, and pulling the expandable braided basket proximally while adjusting a pull force. Thus, the scraper may be repositioned (e.g., using a guidewire) to repeatedly scrape the same regions of the vessel.

In general, these methods may be used to adjust the pull force applied even as the diameter of the vessel lumen changes (narrows or broadens) along its length. The methods described herein may also include pulling the expandable braided basket proximally and adjusting the pull force by operating a control on a handle of the expandable scraper device to expand or contract the expandable braided basket to maintain the pull force between about 0.2 and 1.5 pounds of force to scrape clot material from the wall of the vessel lumen without damaging the wall of the vessel lumen even while a diameter of vessel walls change along a length of the vessel walls.

In any of these apparatuses and methods of performing them, the pull force may be adjusted by operating the control on the handle of the expandable scraper device; the control may include releasing a ratcheting lock on the handle to expand or contract the expandable braided basket.

Any of these methods may include providing feedback of the pull force applied. As mentioned above, these methods of using the apparatus may include applying suction to remove clot material from the vessel lumen. Pulling the expandable braided basket proximally may include maintaining the pull force at an approximately constant level.

Positioning the expandable scraper device within the lumen of the vessel may include comprises inserting the expandable scraper device through a catheter and pulling the expandable braided basket with clot to a distal tip of the catheter and aspirating clot through the catheter.

For example, a method of removing clot (e.g., clot material) may include: positioning an expandable scraper device within a lumen of a vessel in an unexpanded configuration so that an expandable braided basket of the expandable scraper device is positioned distal to or within the clot; expanding the expandable braided basket against a wall of the vessel lumen where the expandable braided basket is configured to apply a maximum scraping force against the wall of the vessel lumen of 1.5 pounds of force or less, further wherein the expandable braided basket is biased to return to the unexpanded configuration in an unconstrained state, and wherein the expandable braided basket has a length of between 3 and 10 cm in the unexpanded configuration, wherein the expandable braided basket is formed of between 20 and 60 nickel titanium wires each having a diameter of between 0.15 mm and 0.35 mm; and pulling the expandable braided basket proximally while adjusting a pull force by operating a control on a handle of the expandable scraper device to expand or contract the expandable braided basket to maintain the pull force between about 0.2 and 1.5 pounds of force to scrape clot material from the wall of the vessel lumen without damaging the wall of the vessel lumen. Expanding may comprise expanding the expandable braided basket so that an inner elongate member which extends between a distal end of the expandable braided basket and a proximal end of the expandable braided basket is positioned within the expandable braided basket offset from a midline of the expandable braided basket.

A method of removing clot may include: positioning an expandable scraper device within a lumen of a vessel in an unexpanded configuration so that an expandable braided basket of the expandable scraper device is positioned distal to or within the clot; expanding the expandable braided basket against a wall of the vessel lumen where the expandable braided basket is configured to apply a maximum scraping force against the wall of the vessel lumen of 1.5 pounds of force or less, further wherein the expandable braided basket expanded against a bias force configured to return to the expandable braided basket to the unexpanded configuration in an unconstrained state; and pulling the expandable braided basket proximally while adjusting a pull force by operating a control on a handle of the expandable scraper device to expand or contract the expandable braided basket to maintain the pull force between about 0.2 and 1.5 pounds of force to scrape clot material from the wall of the vessel lumen without damaging the wall of the vessel lumen, wherein adjusting the pull force by operating the control on the handle of the expandable scraper device comprises releasing a ratcheting lock on the handle and sliding a slider to expand or contract the expandable braided basket.

In operation, the device may remove clot by positioning the expandable scraper device within a lumen of a vessel so that an expandable braided basket of the expandable scraper device is positioned distal to or within the clot. The method may include forming a loop of a portion of a proximal end of an elongate shaft of the expandable scraper and securing a projection extending from the elongate shaft within a lock formed on a handle of the expandable scraper device, so that the effective length of the expandable scraper device is shortened. The expandable braided basket may be expanded against the wall of the vessel lumen either before or after shortening the elongate shaft by forming the loop, or it may be expanded against the wall after forming the loop. The device (e.g., the expandable braided basket) may then be pulled proximally to scrape clot material from the wall of the vessel lumen without damaging the wall of the vessel lumen, e.g., by pulling on the handle.

In general, the device may be operated by adjusting diameter of the basket during operation (e.g., when pulling or pushing the basket to scrape clot material) in order to maintain the pull force on the basket relatively constant (or within a predetermined range) to prevent jamming and/or damage to the vessel wall. For example, the expansion of the basket may be manually or automatically adjusted. In some examples the expansion of the basket may be adjusted by manually adjusting the diameter of the basket as it is pulled to maintain force within a range. The basket diameter may be adjusted as described above, e.g., by acting a control (e.g., button) to release the ratcheting lock on the handle, then sliding the slider distally or proximally.

For example, a method of removing clot may include positioning an expandable scraper device within a lumen of a vessel so that an expandable braided basket of the expandable scraper device is positioned distal to or within the clot; expanding the expandable braided basket against the wall of the vessel lumen with a radial force of between about 0.25 and 0.6 pounds of force against the wall of the vessel lumen, and pulling the expandable braided basket proximally while adjusting the pull force by operating one or more controls on a handle of the expandable scraper device to expand or contract the expandable braided basket to maintain the pull force between about 0.18 and 0.4 pounds of force to scrape clot material from the wall of the vessel lumen without damaging the wall of the vessel lumen.

Thus a pull (or pushing) force may be maintained within this target range of between 0.18 and 0.4 lbf (referred to as "constant force" or a force within this target range) by reducing or expanding basket diameter, e.g., during removal. As mentioned, this may be done manually by a user managing the one or more controls (e.g., lock release control and slider control).

Figure 28B:
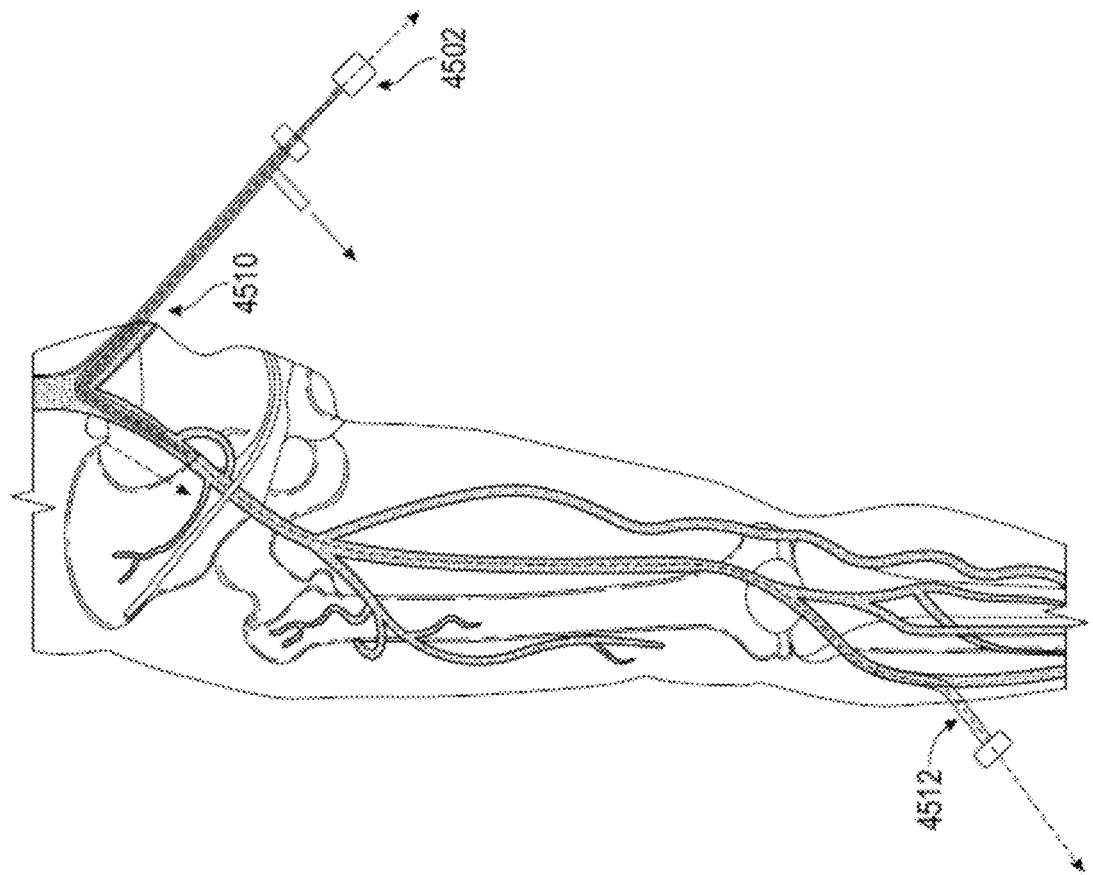
FIGS. 28A-28C illustrate access method for the devices descried herein.

Any of the methods and apparatuses described herein may include insertion of the expandable scraper device into the same vascular region as a clot removal device such as an aspirating lumen and/or an inverting thrombectomy apparatus as described above. For example, FIGS. 28A-28C illustrate different insertion sites into the vasculature with different combination of techniques for inserting the expandable scraper device and an inverting thrombectomy apparatus.

Figure 28A:
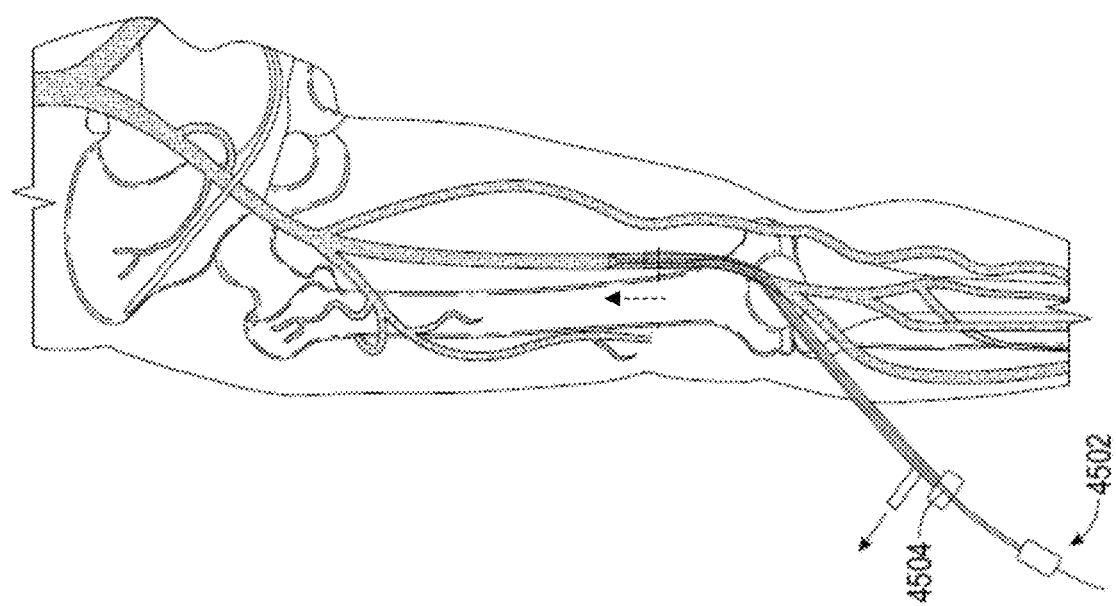
Figure 28C:
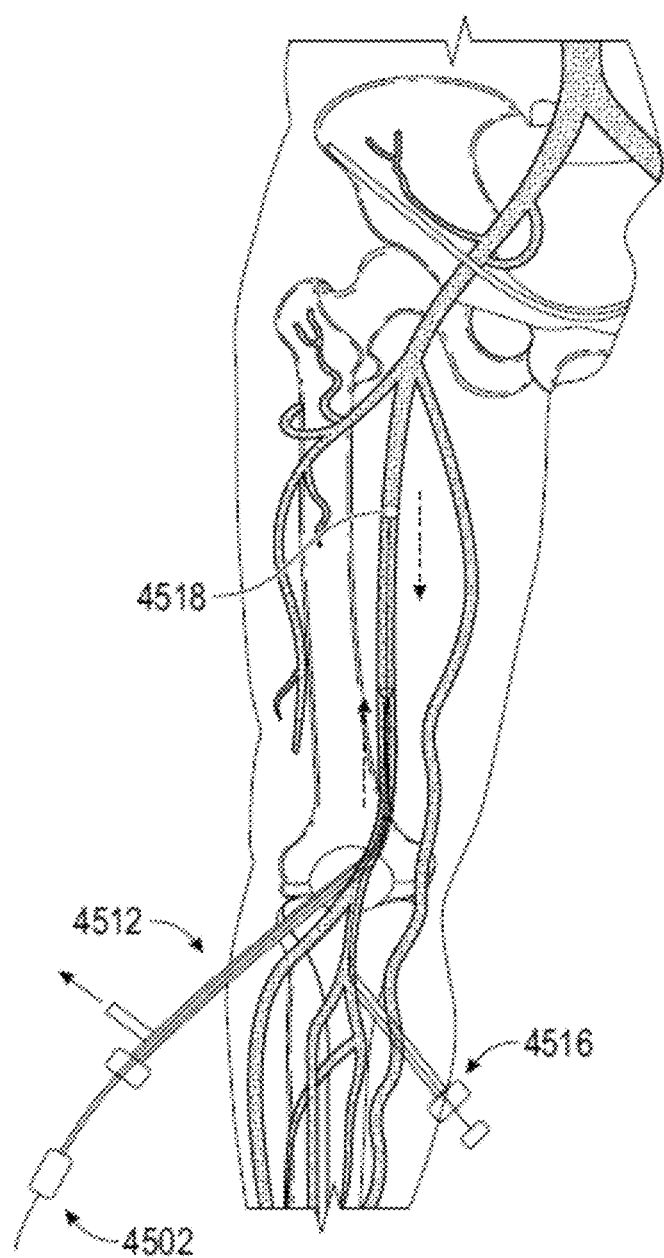

For example, FIG. 28A illustrates a single vascular entry (e.g., "single stick") in which both the expandable scraper device and the inverting thrombectomy apparatus is inserted anterograde from the popliteal region. In FIG. 28A the inverting thrombectomy apparatus 4502 is inserted through a sheath 4504 (shown as a 14F sheath with aspiration). The same sheath may be used to separately insert an expandable scraper device (not shown). Thus, the two devices may be alternately inserted to the target region; aspiration may be applied after the expandable scraper device is used and/or the inverting thrombectomy apparatus may be used.

FIG. 28B illustrates an alternative method in which two separate vascular access regions are used. In FIG. 28B, one of the devices (e.g., the inverting thrombectomy apparatus) is inserted from a contra femoral location 4510 (retrograde) while the second device (e.g., an expandable scraper device) is inserted from the popliteal region or an anterior tibial vein 4512. Alternatively, FIG. 28C illustrates another example of a method in which two access sites are used; in this example, the popliteal region 4512 is used for inserting the inverting thrombectomy apparatus 4502 and/or the expandable scraper device, and a second side, at the saphenous vein may be used for inserting another device (e.g., the expandable scraper device) and/or a balloon 4518, as shown.

FIGS. 29A-29E illustrate additional examples of method of accessing the vasculature using the devices described herein. For example, in FIG. 29A, the apparatus includes a single introducer sheath (e.g., an 18F introducer sheath) into which the expandable scraper device 4612 may be inserted in parallel with the inverting thrombectomy apparatus 4602. In this example the sheath may be inserted into the popliteal region as shown above in FIG. 28A.

FIG. 29B shows an alternative access method for the expandable scraper device 4612 to be inserted in parallel with the inverting thrombectomy apparatus 4602, in which the expandable scraper device is inserted through the inverting thrombectomy apparatus, as shown. In some examples this may be done without an introducer sheath (as shown).

Figure 29C:
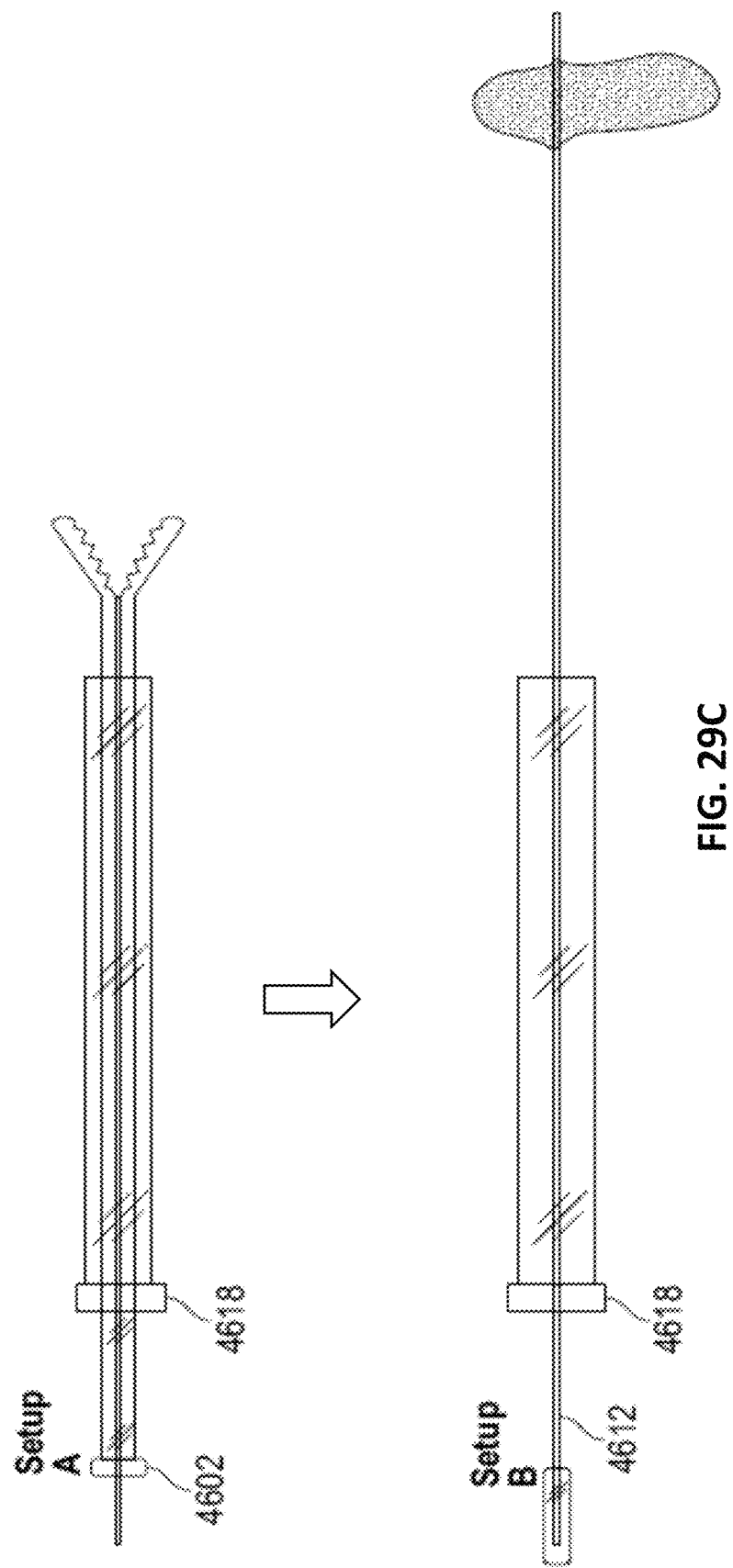

FIG. 29C illustrates another example, similar to FIG. 28A, in which the inverting thrombectomy apparatus 4602 and the expandable scraper device 4612 are inserted through the same access region (e.g., the popliteal region) and through the same sheath 4618. The two devices may be used in an alternating manner. For example, the expandable scraper device may be used between passes with the inverting thrombectomy apparatus.

In any of these methods, a guidewire may be used to guide the two devices to the target region for clot removal. The guidewire may remain in place or may be removed during the procedure.

Figure 29D:
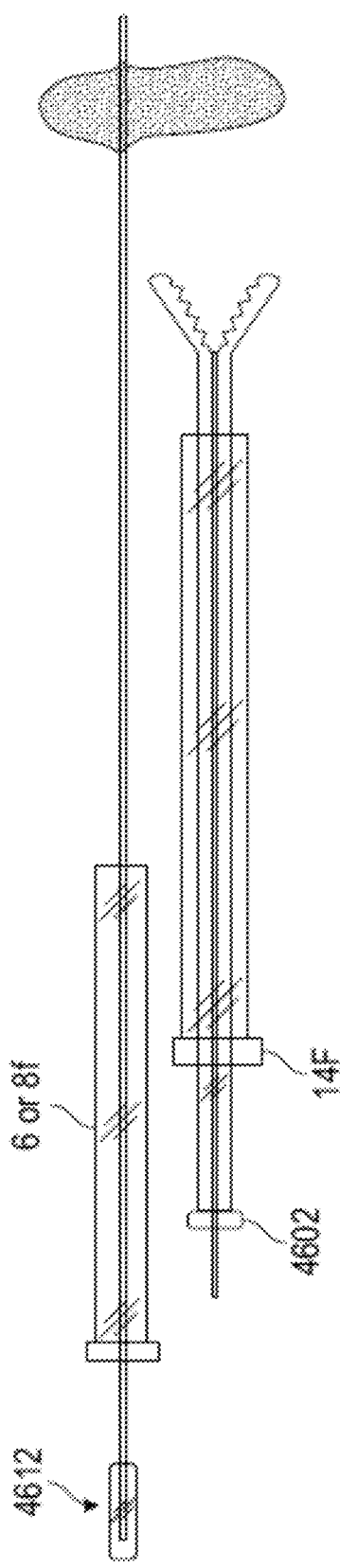
Figure 29E:
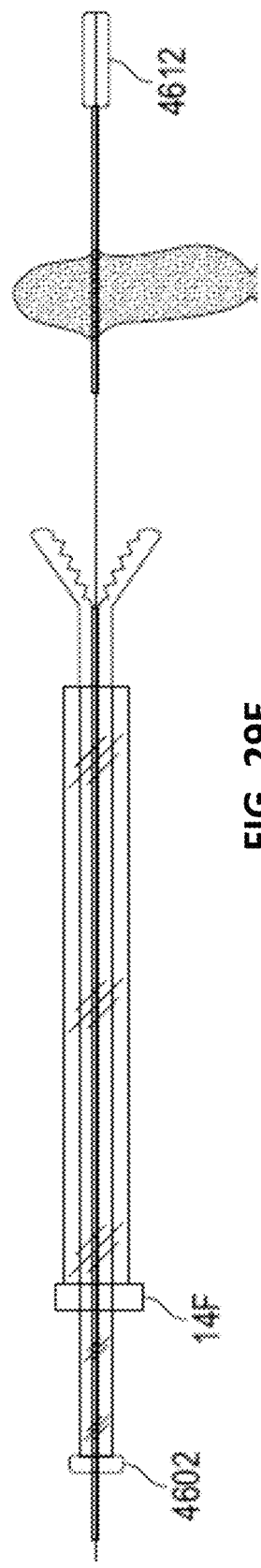

FIGS. 29D and 29E illustrate examples of multiple access locations similar to that shown in FIGS. 28B and 28C. In FIG. 28D, the expandable scraper device 4612 is inserted from the access point of the lower popliteal region, using a sheath, and the inverting thrombectomy apparatus 4602 is inserted from a higher popliteal vein region, using a second sheath. Both devices may be steered to converge on the treatment region, as shown.

In FIG. 29E the expandable scraper device 4612 is inserted from the access point of the popliteal (posterior tibial) region and the inverting thrombectomy apparatus 4602 is inserted from a femoral vein region. Both devices converge on the treatment region, but from different directions, as shown.

Inverting Tube Apparatuses

Figure 30A:
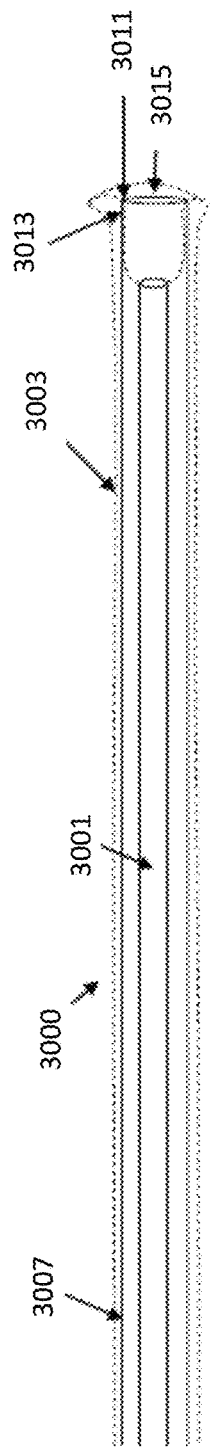
FIGS. 30A-30C illustrate an example of an inverting tube (e.g., thrombectomy) apparatus that may be used to remove material from a vessel.
Figure 30B:
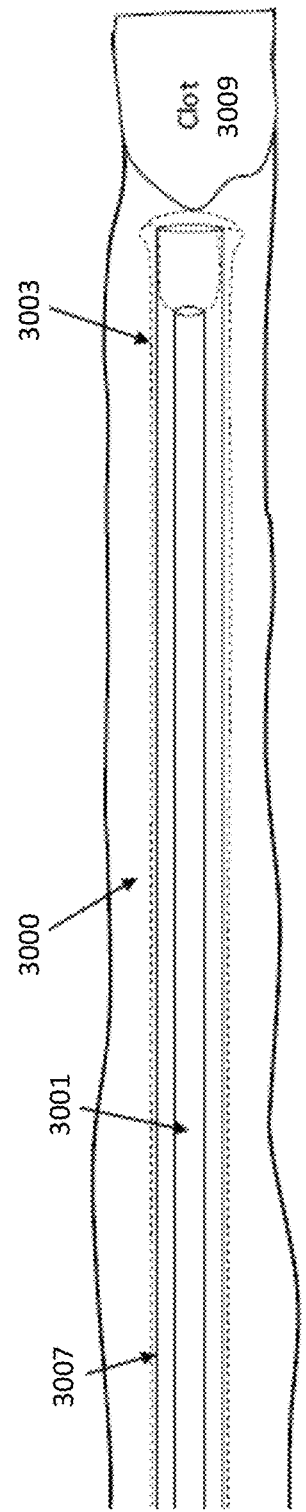
Figure 30C:
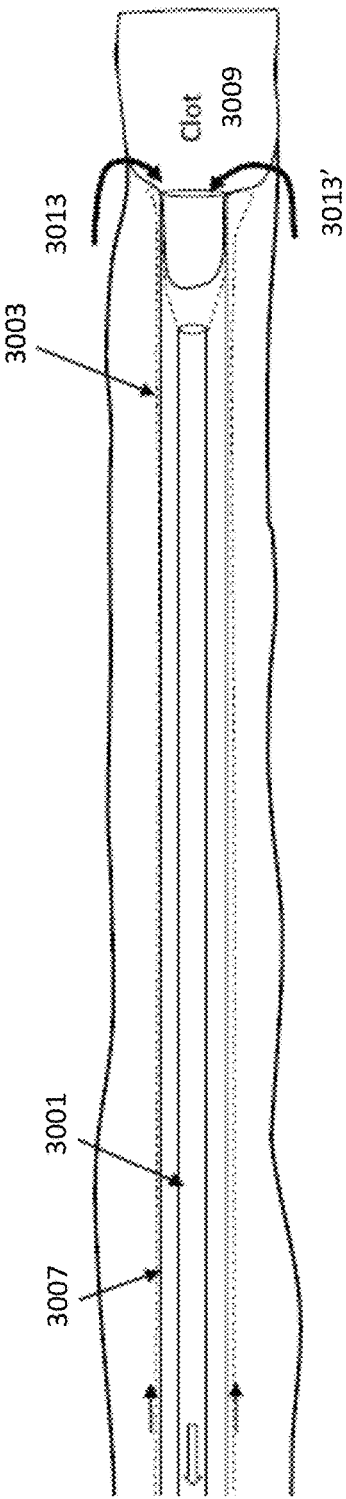

In general, an inverting tube apparatus (also referred to herein as "mechanical thrombectomy apparatus" or "inverting thrombectomy apparatus") may be configured to remove material, such as clot, using a length of inverting tube, as shown in FIGS. 30A-30C. The apparatuses and methods of using them described herein may be used within the vasculature, including the neurovasculature and the peripheral vasculature.

For example, FIG. 30A illustrates an example of an inverting thrombectomy apparatus 3000, such as described in U.S. patent application Ser. No. 15/496,570, and in U.S. Pat. No. 9,463,035. The apparatus includes an inversion support catheter 3007 and a flexible tube 3003 that extends over the outer surface of the inversion catheter. The flexible tube may be referred to as a tractor tube (or flexible tractor tube) and may be attached at one end region to a puller 3001, which may be pull wire or pull tube (e.g., catheter), e.g., at the distal end region of the puller. In some examples the flexible tube may be attached proximal to the distal end of the puller (e.g. between 1 mm and 50 mm from the distal end, between 1 mm and 40 mm, between 1 mm and 30 mm, greater than 5 mm, greater than 10 mm, greater than 20 mm, greater than 30 mm, etc. from the distal end of the puller). Pulling the puller proximally inverts the flexible tube over the distal end opening 3011 of the inversion support catheter to capture and remove a material (such as a clot) in the vessel lumen, as shown in FIGS. 30B and 30C. In operation, the amount of the material that may be captured corresponds to the length of the flexible tube.

In FIG. 30B the inverting tractor mechanical thrombectomy apparatus 3000 is shown deployed near a clot 3009. In the deployed configuration the puller 3001 (shown here as a puller micro catheter, alternatively the puller may be a wire) is held within an elongate inversion support catheter 3007 so that the flexile tractor tube 3003 extends from the end of the puller 3001 and expands toward the inner radius of the elongate inversion support catheter 3007; at the distal end opening 3011 of the elongate inversion support catheter the tractor tube inverts over itself and extends proximally in an inverted configuration over the distal end of the elongate inversion support catheter. As shown in FIG. 30C, by pulling the puller proximally, the tractor tube rolls 3013, 3013' and everts over the distal end opening of the elongate inversion support catheter, drawing the adjacent clot into the elongate inversion support catheter, as shown.

FIG. 30A the elongate inversion support catheter is an elongate tube having a distal end that has the same size inner diameter as the proximal length of the inversion support catheter. In some examples the distal end of the inversion support catheter may be funnel-shaped (or configured to expand into a funnel shape, see, e.g. FIGS. 2A-2B). In FIGS. 30A-30C, the inversion support catheter 3007 is shown positioned between the tractor tube (e.g., flexible tube 3003) and the puller 3001 so that the flexible tube can be pulled proximally by pulling on the puller and rolling the flexible tube into the elongate inversion support catheter so that it inverts. The portion of the flexible tube that is inverted over the distal end of the elongate inversion support catheter has an outer diameter that is greater than the outer diameter of the elongate inversion support catheter. The flexible tube may be biased so that it has a relaxed expanded configuration with a diameter that is greater than the outer diameter (OD) of the elongate inversion support catheter; in addition, the flexible tube may also be configured (e.g., by heat setting, etc.) so that when the flexible tube is everted and rolled over the distal end opening into the elongate inversion support catheter, the outer diameter of the flexible tube within the elongate inversion support catheter has an outer diameter that is about y times (y fold) the inner diameter of the elongate inversion support catheter (e.g., where y is greater than 0.1×, 0.5×, 0.6×, 0.7×, 0.75×, 0.8×, 0.9×, 1×, etc. the inner diameter, ID, of the elongate inversion support catheter. This combination of an un-inverted diameter of the flexible tube of greater than the diameter of the OD of the elongate inversion support catheter and an inverted diameter of the flexible tube of greater than, e.g., 0.7× the ID of the elongate inversion support catheter is surprisingly helpful for preventing jamming of the apparatus, both when deploying the apparatus and when rolling the flexible tube over the distal end opening of the elongate inversion support catheter to grab a clot. The flexible tube may be expandable and may be coupled to the puller as shown. In some examples the flexible tube and the puller may comprise the same material, but the flexible tube may be more flexible and/or expandable, or may be connected to elongate puller (e.g., a push/pull wire or catheter). As mentioned above, the puller may be optional (e.g., the flexible tube may itself be pulled proximally into the inversion support catheter).

In FIG. 30C the clot may be drawn into the elongate inversion support catheter by pulling the flexible tube proximally i inverting thrombectomy apparatus into the distal end of the elongate inversion support catheter, as indicated by the arrows 3013, 3013' showing pulling of the inner portion of the flexible tube, resulting in rolling the flexible tube over the end opening of the catheter and into the catheter distal end and inverting the expandable distal end region so that it is pulled into the catheter, shown by arrows. The end of the flexible tube outside of the catheter may be loose relative to the outer wall of the catheter.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one example, the features and elements so described or shown can apply to other examples. It will also be appreciated by those of skill in the art that references to a structure or feature that is disposed "adjacent" another feature may have portions that overlap or underlie the adjacent feature.

Terminology used herein is for the purpose of describing particular examples only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative examples are described above, any of a number of changes may be made to various examples without departing from the scope of the invention as described by the claims. For example, the order in which various described method steps are performed may often be changed in alternative examples, and in other alternative examples one or more method steps may be skipped altogether. Optional features of various device and system examples may be included in some examples and not in others. Therefore, the foregoing description is provided primarily for exemplary purposes and should not be interpreted to limit the scope of the invention as it is set forth in the claims.

The examples and illustrations included herein show, by way of illustration and not of limitation, specific examples in which the subject matter may be practiced. As mentioned, other examples may be utilized and derived there from, such that structural and logical substitutions and changes may be made without departing from the scope of this disclosure. Such examples of the inventive subject matter may be referred to herein individually or collectively by the term "invention" merely for convenience and without intending to voluntarily limit the scope of this application to any single invention or inventive concept, if more than one is, in fact, disclosed. Thus, although specific examples have been illustrated and described herein, any arrangement calculated to achieve the same purpose may be substituted for the specific examples shown. This disclosure is intended to cover any and all adaptations or variations of various examples. Combinations of the above examples, and other examples not specifically described herein, will be apparent to those of skill in the art upon reviewing the above description.

What is claimed is:

1. A method of removing clot, the method comprising:
positioning an expandable scraper device within a lumen of a vessel in an unexpanded configuration so that an expandable braided basket of the expandable scraper device is positioned distal to or within the clot;

expanding the expandable braided basket to an expanded configuration against a wall of the vessel lumen where the expandable braided basket is configured to apply a maximum scraping force against the wall of the vessel lumen of 1.5 pounds of force or less, wherein the expandable braided basket is loosely braided so that it deforms along the long axis to limit the maximum scraping force to 1.5 pounds or less; and pulling the expandable braided basket proximally while adjusting a pull force by operating a control on a handle of the expandable scraper device to expand or contract the expandable braided basket to maintain the pull force between about 0.2 and 1.5 pounds of force to scrape clot material from the wall of the vessel lumen without damaging the wall of the vessel lumen.

2. The method of claim 1, wherein expanding the expandable braided basket comprises expanding the expandable braided basket against a bias force configured to return the expandable braided basket to the unexpanded configuration in an unconstrained state.

3. The method of claim 1, wherein expanding the expandable braided basket comprises expanding the expandable braided basket from a length of between 3 and 10 cm in the unexpanded configuration.

4. The method of claim 1, wherein expanding the expandable braided basket comprises expanding a braid of between 20 and 60 nickel titanium wires each having a diameter of between 0.15 mm and 0.35 mm into the expanded configuration.

5. The method of claim 1, wherein expanding comprises expanding the expandable braided basket so that an inner elongate member which extends between a distal end of the expandable braided basket and a proximal end of the expandable braided basket is positioned within the expandable braided basket offset from a midline of the expandable braided basket.

6. The method of claim 1, wherein adjusting the pull force by operating the control on the handle of the expandable scraper device comprises operating a finger slider to manually adjust expansion of the expandable braided basket to maintain the pull force between about 0.2 and 1.5 pounds of force.

7. The method of claim 1, wherein adjusting the pull force by operating the control on the handle of the expandable scraper device comprises operating both a release button and a finger slider to manually adjust expansion of the expandable braided basket to maintain the pull force between about 0.2 and 1.5 pounds of force.

8. The method of claim 1, wherein adjusting the pull force by operating the control on the handle of the expandable scraper device comprises releasing a ratcheting lock on the handle to expand or contract the expandable braided basket.

9. The method of claim 1, further comprising providing feedback of the pull force applied.

10. The method of claim 1, further comprising applying suction to remove clot material from the vessel lumen.

11. The method of claim 1, wherein pulling the expandable braided basket proximally comprises maintaining the pull force at an approximately constant level.

12. The method of claim 1, wherein positioning the expandable scraper device within the lumen of the vessel comprises inserting the expandable scraper device through a catheter and pulling the expandable braided basket with clot to a distal tip of the catheter and aspirating clot through the catheter.

13. The method of claim 1, further comprising repeatedly positioning the expandable scraper device within the lumen of the vessel to scrape a same location of the vessel by advancing the expandable scraper over a guidewire in the collapsed configuration, expanding the expandable scraper, and pulling the expandable braided basket proximally while adjusting the pull force.

14. The method of claim 1, wherein pulling the expandable braided basket proximally comprises adjusting the pull force by operating a control on a handle of the expandable scraper device to expand or contract the expandable braided basket to maintain the pull force between about 0.2 and 1.5 pounds of force to scrape clot material from the wall of the vessel lumen without damaging the wall of the vessel lumen as a diameter of vessel walls change along a length of the vessel walls.

15. A method of removing clot, the method comprising:
positioning an expandable scraper device within a lumen of a vessel in an unexpanded configuration so that an expandable braided basket of the expandable scraper device is positioned distal to or within the clot;

expanding the expandable braided basket against a wall of the vessel lumen where the expandable braided basket is configured to apply a maximum scraping force against the wall of the vessel lumen of 1.5 pounds of force or less, further wherein the expandable braided basket is biased to return to the unexpanded configuration in an unconstrained state, and wherein the expandable braided basket has a length of between 3 and 10 cm in the unexpanded configuration, wherein the expandable braided basket is loosely braided so that it deforms along the long axis to limit the maximum scraping force to 1.5 pounds or less and is formed of between 20 and 60 nickel titanium wires each having a diameter of between 0.15 mm and 0.35 mm; and pulling the expandable braided basket proximally while adjusting a pull force by operating a control on a handle of the expandable scraper device to expand or contract the expandable braided basket to maintain the pull force between about 0.2 and 1.5 pounds of force to scrape clot material from the wall of the vessel lumen without damaging the wall of the vessel lumen.

16. The method of claim 15, wherein expanding comprises expanding the expandable braided basket so that an inner elongate member which extends between a distal end of the expandable braided basket and a proximal end of the expandable braided basket is positioned within the expandable braided basket offset from a midline of the expandable braided basket.

17. The method of claim 15, wherein adjusting the pull force by operating the control on the handle of the expandable scraper device comprises operating a finger slider to manually adjust expansion of the expandable braided basket to maintain the pull force between about 0.2 and 1.5 pounds of force.

18. The method of claim 15, wherein adjusting the pull force by operating the control on the handle of the expandable scraper device comprises operating both a release button and a finger slider to manually adjust expansion of the expandable braided basket to maintain the pull force between about 0.2 and 1.5 pounds of force.

19. The method of claim 15, wherein adjusting the pull force by operating the control on the handle of the expandable scraper device comprises releasing a ratcheting lock on the handle to expand or contract the expandable braided basket.

20. The method of claim 15, further comprising providing feedback of the pull force applied.

21. The method of claim 15, further comprising applying suction to remove clot material from the vessel lumen.

22. The method of claim 15, wherein pulling the expandable braided basket proximally comprises maintaining the pull force at an approximately constant level.

23. The method of claim 15, wherein positioning the expandable scraper device within the lumen of the vessel comprises inserting the expandable scraper device through a catheter and pulling the expandable braided basket with clot to a distal tip of the catheter and aspirating clot through the catheter.

24. The method of claim 15, further comprising repeatedly positioning the expandable scraper device within the lumen of the vessel to scrape a same location of the vessel by advancing the expandable scraper over a guidewire in the collapsed configuration, expanding the expandable scraper, and pulling the expandable braided basket proximally while adjusting the pull force.

25. The method of claim 15, wherein pulling the expandable braided basket proximally comprises adjusting the pull force by operating a control on a handle of the expandable scraper device to expand or contract the expandable braided basket to maintain the pull force between about 0.2 and 1.5 pounds of force to scrape clot material from the wall of the vessel lumen without damaging the wall of the vessel lumen as a diameter of vessel walls change along a length of the vessel walls.

26. A method of removing clot, the method comprising:
positioning an expandable scraper device within a lumen of a vessel in an unexpanded configuration so that an expandable braided basket of the expandable scraper device is positioned distal to or within the clot;
expanding the expandable braided basket against a wall of the vessel lumen where the expandable braided basket is configured to apply a maximum scraping force against the wall of the vessel lumen of 1.5 pounds of force or less, wherein the expandable braided basket is loosely braided so that it deforms along the long axis to limit the maximum scraping force to 1.5 pounds or less, further wherein the expandable braided basket expanded against a bias force configured to return the expandable braided basket to the unexpanded configuration in an unconstrained state; and
pulling the expandable braided basket proximally while adjusting a pull force by operating a control on a handle of the expandable scraper device to expand or contract the expandable braided basket to maintain the pull force between about 0.2 and 1.5 pounds of force to scrape clot material from the wall of the vessel lumen without damaging the wall of the vessel lumen,
wherein adjusting the pull force by operating the control on the handle of the expandable scraper device comprises releasing a ratcheting lock on the handle and sliding a slider to expand or contract the expandable braided basket.

27. The method of claim 1, wherein pulling the expandable braided basket proximally comprises at least partially inverting the basket.

28. The method of claim 15, wherein pulling the expandable braided basket proximally comprises at least partially inverting the basket.

29. The method of claim 26, wherein pulling the expandable braided basket proximally comprises at least partially inverting the basket.

* * * * *